(12) United States Patent
Wang

(10) Patent No.: US 11,915,347 B2
(45) Date of Patent: Feb. 27, 2024

(54) SYSTEMS AND METHODS FOR RECONSTRUCTING CARDIAC IMAGES

(71) Applicant: SHANGHAI UNITED IMAGING HEALTHCARE CO., LTD., Shanghai (CN)

(72) Inventor: Yi Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/933,469

(22) Filed: Sep. 19, 2022

(65) Prior Publication Data

US 2023/0019335 A1     Jan. 19, 2023

Related U.S. Application Data

(63) Continuation of application No. 17/202,308, filed on Mar. 15, 2021, now Pat. No. 11,450,038, which is a
(Continued)

(30) Foreign Application Priority Data

Jun. 11, 2018   (CN) .......................... 201810597965.1
Sep. 27, 2018   (CN) .......................... 201811133609.0
(Continued)

(51) Int. Cl.
*G06T 11/00*     (2006.01)
*G06T 7/90*      (2017.01)
(Continued)

(52) U.S. Cl.
CPC ............ *G06T 11/008* (2013.01); *A61B 5/489* (2013.01); *A61B 6/032* (2013.01); *A61B 6/503* (2013.01);
(Continued)

(58) Field of Classification Search
CPC ............ G06T 11/005; G06T 2211/412; G06T 11/008; G06T 2207/30048;
(Continued)

(56) References Cited

U.S. PATENT DOCUMENTS 5,764,813 A    6/1998   Murayama et al.
6,522,712 B1   2/2003   Yavuz et al.
(Continued)

FOREIGN PATENT DOCUMENTS

CN    101352352 A    1/2009
CN    101727666 A    6/2010
(Continued)

OTHER PUBLICATIONS

Thomas Köhler et al., Automatic No-Reference Quality Assessment for Retinal Rundus Images Using Vessel Segmentation, Proceedings of the 26th IEEE International Symposium on Computer-Based Medical Systems, 95-100, 2013.
(Continued)

*Primary Examiner* — Ajibola A Akinyemi
(74) *Attorney, Agent, or Firm* — METIS IP LLC

(57) ABSTRACT

A method for reconstructing target cardiac images is provided. The method may include: obtaining a plurality of projection data corresponding to a plurality of cardiac motion phases; determining a plurality of cardiac motion parameters corresponding to at least a portion of the plurality of cardiac motion phases based on the plurality of projection data; determining a phase of interest based on the plurality of cardiac motion parameters; and/or reconstructing the one or more target cardiac images of the phase of interest.

20 Claims, 23 Drawing Sheets

Related U.S. Application Data continuation of application No. 16/437,003, filed on Jun. 11, 2019, now Pat. No. 10,950,016.

(30) Foreign Application Priority Data

| Sep. 27, 2018 | (CN) | ........................ 201811133622.6 |
| Sep. 27, 2018 | (CN) | ........................ 201811134373.2 |
| Sep. 27, 2018 | (CN) | ........................ 201811134375.1 |

(51) Int. Cl.

| G06T 7/11 | (2017.01) |
| G06T 5/00 | (2006.01) |
| G06T 5/50 | (2006.01) |
| G06T 5/20 | (2006.01) |
| A61B 5/00 | (2006.01) |
| G06T 7/00 | (2017.01) |
| A61B 6/03 | (2006.01) |
| A61B 6/00 | (2006.01) |

(52) U.S. Cl.
CPC .............. *A61B 6/504* (2013.01); *G06T 5/003* (2013.01); *G06T 5/20* (2013.01); *G06T 5/50* (2013.01); *G06T 7/0014* (2013.01); *G06T 7/11* (2017.01); *G06T 7/90* (2017.01); *G06T 11/005* (2013.01); *A61B 6/481* (2013.01); *A61B 6/541* (2013.01); *G06T 2207/10072* (2013.01); *G06T 2207/20201* (2013.01); *G06T 2207/30048* (2013.01); *G06T 2207/30101* (2013.01); *G06T 2207/30168* (2013.01); *G06T 2211/404* (2013.01); *G06T 2211/412* (2013.01)

(58) Field of Classification Search
CPC . G06T 2207/10072; G06T 2207/20201; G06T 2207/30101; G06T 2207/30168; G06T 2211/404; G06T 5/003; G06T 5/20; G06T 5/50; G06T 7/0014; G06T 7/11; G06T 7/136; G06T 7/90; G06T 2207/10081; G06T 11/003; G06T 2200/04; G06T 2207/10028; G06T 2207/10104; G06T 2207/30061; G06T 7/0012; G06T 7/0016
USPC ....................................................... 382/131
See application file for complete search history.

(56) References Cited

U.S. PATENT DOCUMENTS

| 6,539,074 | B1 | 3/2003 | Yavuz et al. |
| 10,555,702 | B1 | 2/2020 | Couderc et al. |
| 11,024,062 | B2 | 6/2021 | Wang |
| 2003/0002616 | A1 | 1/2003 | Cesmeli |
| 2007/0073114 | A1 | 3/2007 | Gundel |
| 2007/0248253 | A1 | 10/2007 | Manzke et al. |
| 2008/0075343 | A1 | 3/2008 | John et al. |
| 2009/0003513 | A1 | 1/2009 | Grass et al. |
| 2009/0232379 | A1 | 9/2009 | Kohler et al. |
| 2010/0074485 | A1 | 3/2010 | Movassaghi et al. |
| 2012/0229829 | A1 | 9/2012 | Hara |
| 2012/0275673 | A1* | 11/2012 | Star-Lack ............. G06T 11/005 382/131 |
| 2014/0219524 | A1 | 8/2014 | Takeguchi et al. |
| 2014/0227682 | A1 | 8/2014 | Seth et al. |
| 2015/0022523 | A1 | 1/2015 | Murray et al. |
| 2015/0348277 | A1 | 12/2015 | Frinking |
| 2016/0035112 | A1 | 2/2016 | Lou et al. |
| 2016/0171716 | A1 | 6/2016 | Schafer et al. |
| 2017/0030990 | A1 | 2/2017 | Janich et al. |
| 2017/0069105 | A1 | 3/2017 | Kano et al. |
| 2017/0083742 | A1 | 3/2017 | Lamare et al. |
| 2017/0148157 | A1 | 5/2017 | Ninomiya |
| 2017/0178285 | A1 | 6/2017 | Jiang et al. |
| 2017/0196527 | A1 | 7/2017 | Kokubun |
| 2017/0249740 | A1* | 8/2017 | Brehm ................. A61B 6/5235 |
| 2017/0301066 | A1 | 10/2017 | Wang et al. |
| 2018/0315191 | A1 | 11/2018 | Meng et al. |
| 2018/0353098 | A1 | 12/2018 | Ye et al. |
| 2019/0378309 | A1 | 12/2019 | Wang |
| 2019/0378312 | A1 | 12/2019 | Wang |

FOREIGN PATENT DOCUMENTS

| CN | 102609939 A | 7/2012 |
| CN | 102622775 A | 8/2012 |
| CN | 102663747 A | 9/2012 |
| CN | 102800111 A | 11/2012 |
| CN | 102982542 A | 3/2013 |
| CN | 103337071 A | 10/2013 |
| CN | 103356241 A | 10/2013 |
| CN | 103390274 A | 11/2013 |
| CN | 104240180 A | 12/2014 |
| CN | 104331914 A | 2/2015 |
| CN | 104545973 A | 4/2015 |
| CN | 104657984 A | 5/2015 |
| CN | 104794714 A | 7/2015 |
| CN | 104867147 A | 8/2015 |
| CN | 105354835 A | 2/2016 |
| CN | 106296784 A | 1/2017 |
| CN | 106780651 A | 5/2017 |
| CN | 107049475 A | 8/2017 |
| CN | 107468267 A | 12/2017 |
| CN | 107483920 A | 12/2017 |
| CN | 108182720 A | 6/2018 |
| CN | 109345526 A | 2/2019 |
| CN | 109377481 A | 2/2019 |
| DE | 102006037601 A1 | 2/2008 |
| EP | 1008860 A2 | 6/2000 |
| WO | 03030101 A2 | 4/2003 |
| WO | 2009070300 A1 | 6/2009 |
| WO | 2013177779 A1 | 12/2013 |
| WO | 2015164761 A1 | 10/2015 |

OTHER PUBLICATIONS

First Office Action in Chinese Application No. 201811134375.1 dated Dec. 14, 2020, 17 pages.
First Office Action in Chinese Application No. 201811134373.2 dated Dec. 30, 2020, 21 pages.
First Office Action in Chinese Application No. 201810597965.1 dated Dec. 18, 2020, 12 pages.
M. Vembar et al., A Dynamic Approach to Identifying Desired Physiological Phases for Cardiac Imaging Using Multislice Spiral CT, Medical Physics, 30(7): 1683-1693, 2003.
Guo, Qi et al., Summarize of Evaluation Methods for Image Segmentation, Proceedings of the 9th Youth Academic Conference of China Instrument and Control Society, 2007, 6 pages.
Pratomo Adhi Nugroho et al., 3D Heart Image Reconstruction and Visualization with Marching Cubes Algorithm, 2016 International Conference on Knowledge Creation and Intelligent Computing (KCIC), 2016, 7 pages.
Jiang, Jun et al., Three Dimensional Reconstruction of Heart Based on Chinese Digitized Visible Human, Journal of Tissue Engineering and Reconstructive Surgery, 10(1): 8-10, 2014.

* cited by examiner

600

Obtaining a plurality of mean absolute differences (MADs) by determining an MAD between two cardiac images of each two adjacent sampled cardiac motion phases ~ 6202

Determining the plurality of cardiac motion parameters corresponding to the plurality of sampled cardiac motion phases based on the plurality of mean absolute differences ~ 6204

Determining a mean phase based on the plurality of cardiac motion parameters corresponding to the plurality of sampled cardiac motion phases ~ 6206

Determining a set of initial cardiac images of interest based on the one or more cardiac images of the sampled cardiac motion phase(s), an average cardiac rate, and/or a standard deviation of cardiac rates ~ 7302

Extracting one or more vascular images of interest from the set of initial cardiac images of interest ~ 7304

Determining the cardiac motion parameter corresponding to the each sampled cardiac motion phase based on the one or more vascular images of interest ~ 7306

| Performing weighting operation(s) on the motion rate(s) of the vascular center(s) of the sampled cardiac motion phase(s) and a ratio of the sampled cardiac motion phases to all the cardiac motion phases, to obtain weighted motion rate(s) between the sampled cardiac motion phase(s) | ∼ 12802 |

↓

| Obtaining the cardiac motion parameters of all the cardiac motion phases by performing an interpolation on the weighted motion rate(s) | ∼ 12804 |

↓

| Designating a cardiac motion phase corresponding to a maximum motion parameter as the mean phase | ∼ 12806 |

| Selecting one or more cardiac motion phases in a preset range including the mean phase in each cardiac cycle of a plurality of cardiac cycles; and reconstructing one or more cardiac images of the one or more cardiac motion phases based on one or more sub-sets of projection data corresponding to the one or more cardiac motion phases in the each cardiac cycle | ∼ 13902 |

↓

| Determining a phase of interest in the each cardiac cycle based on one or more cardiac images of the each cardiac cycle | ∼ 13904 |

↓

| Obtaining a set of target cardiac images by determining a target cardiac image of the phase of interest in the each cardiac cycle | ∼ 13906 |

- First Maximum Intensity Projection Sub-unit
  30131

- Second Maximum Intensity Projection Sub-unit
  30132

- Difference Determination Sub-unit
  30133

- Second Image Segmentation Unit
  31210

- Left Boundary Determination Unit
  31220

- Right Boundary Determination Unit
  31230

- Upper Boundary Determination Unit
  31240

FIG. 31

SYSTEMS AND METHODS FOR RECONSTRUCTING CARDIAC IMAGES

CROSS-REFERENCE TO RELATED APPLICATIONS

This application is a continuation of U.S. application Ser. No. 17/202,308, filed on Mar. 15, 2021, which is a continuation of U.S. application Ser. No. 16/437,003 (issued as U.S. Pat. No. 10,950,016), filed on Jun. 11, 2019, which claims priority to Chinese Patent Application No. 201811133622.6, filed on Sep. 27, 2018, Chinese Patent Application No. 201811133609.0, filed on Sep. 27, 2018, Chinese Patent Application No. 201810597965.1, filed on Jun. 11, 2018, Chinese Patent Application No. 201811134373.2, filed on Sep. 27, 2018, and Chinese Patent Application No. 201811134375.1, filed on Sep. 27, 2018, the contents of each of which are hereby incorporated by reference in its entirety.

TECHNICAL FIELD

The present disclosure generally relates to imaging technology, and more specifically relates to systems and methods for reconstructing cardiac images.

BACKGROUND

Cardiac image reconstruction is a routine process for clinical computed tomography (CT) application. The clarity of coronary angiography is critical to the quality of reconstructed cardiac images. Due to the physiological characteristics of the heart (especially the right coronary artery), motion artifacts related to heart beating are easily generated during scanning, resulting in a blurred coronary artery in images and low image quality, which can affect diagnosis.

In order to reduce artifacts, data of the diastolic period (75% phase) are used to reconstruct the cardiac images. In theory, the motion rate of the heart in the diastolic period is slower than that of other phases, and thus, the impact of data inconsistency may be attenuated to a certain degree. However, a reconstruction based on data of 75% phase is not suitable for all patients. The patients' heart rates are generally different, and respiratory movement can induce an impact, so that doctors may need to reconstruct a number (or count) of images of different phases offline, and determine an appropriate phase for further diagnosis through tedious comparisons.

With the development of medical device and technology, the use of CT scanners for detecting lesions of patients becomes mature. When using a CT scanner, the CT scanner collects data of multiple phases, and image reconstruction can be performed based on the data of multiple phases to obtain an image of a patient's lesion. It is necessary to use data of an optimal phase for image reconstruction due to the movement of the heart when the heart is scanned using the CT scanner.

In some situations, image reconstruction is performed for each of the multiple phases to obtain multiple reconstructed images corresponding to the multiple phases according to the data of the multiple phases, and an image of an optimal phase is obtained by comparing the multiple reconstructed images. A heart region may need to be identified in the reconstructed image of the optimal phase to obtain a cardiac image. In this way, the image reconstruction operation is generally performed on the data of all the multiple phases. Accordingly, the operation for a large amount of data can consume a large amount of time, and cause problems such as low operational efficiency.

Therefore, it is desirable to provide systems and methods for determining an optimal phase automatically; providing a relatively small field of view for reconstruction; reconstructing cardiac images that have relatively high image qualities and are affected by cardiac motion to a minimum extent, efficiently, cost-effectively, and without waste of time and/or resources.

SUMMARY

In one aspect of the present disclosure, a method for reconstructing one or more target cardiac images is provided. The method may include one or more of the following operations: obtaining a plurality of projection data corresponding to a plurality of cardiac motion phases; reconstructing, in an initial field of view (FOV), at least one preview image based on at least a portion of the plurality of projection data; obtaining a thoracic contour image based on the at least one preview image; determining one or more positions of a thoracic contour boundary in the thoracic contour image; determining a reconstruction center based on the one or more positions of the thoracic contour boundary; and reconstructing, according to the reconstruction center, the one or more target cardiac images based on at least a portion of the plurality of projection data.

In another aspect of the present disclosure, a system for reconstructing one or more target cardiac images is provided. The system may include at least one storage device storing a set of instructions; and at least one processor in communication with the storage device, wherein when executing the set of instructions, the at least one processor is configured to cause the system to perform operations of the method mentioned above.

In another aspect of the present disclosure, a non-transitory computer readable medium storing instructions is provided. The instructions, when executed by at least one processor, may cause the at least one processor to implement the method mentioned above.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6 is a flowchart illustrating an exemplary process for determining a mean phase according to some embodiments of the present disclosure;

FIG. 7 is a flowchart illustrating another exemplary process for determining a mean phase according to some embodiments of the present disclosure;

FIG. 12 is a flowchart illustrating an exemplary process for determining a mean phase based on motion rate(s) of vascular center(s) according to some embodiments of the present disclosure;

FIG. 13 is a flowchart illustrating an exemplary process for obtaining a set of target cardiac images according to some embodiments of the present disclosure;

FIG. 30 is a block diagram illustrating an exemplary maximum intensity projection unit according to some embodiments of the present disclosure;

FIG. 31 is a block diagram illustrating an exemplary boundary determination module according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that the term "object" and "subject" may be used interchangeably as a reference to a thing that undergoes a treatment and/or an imaging procedure in a radiation system of the present disclosure.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
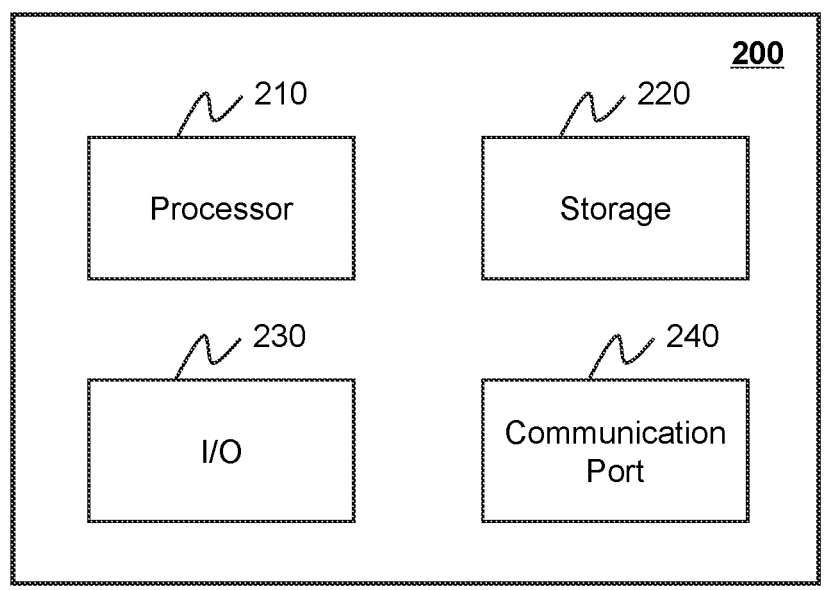
FIG. 2 is a schematic diagram illustrating exemplary hardware and software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

One aspect of the present disclosure relates to methods, systems, computing devices, and computer readable storage mediums for cardiac image reconstruction, which may select a plurality of sampled data at regular intervals in one or more cardiac cycles, obtain corresponding reconstructed image(s), and determine a mean phase according to the reconstructed image(s) of a plurality of phases. Image data corresponding to phases in a preset range near the mean phase may be selected in each cardiac cycle to determine a phase of interest in the each cardiac cycle, and accordingly, a sequence of cardiac images of phases of interest may be obtained. The methods can accurately determine an optimal phase of each cardiac cycle, reduce artifacts induced by cardiac motion, and improve the image quality of the reconstructed cardiac image(s).

Another aspect of the present disclosure relates to methods, systems, computing devices, and computer readable storage mediums for cardiac image reconstruction, which may obtain a plurality of preview images, obtain a thoracic contour image based on the plurality of preview images and a maximum intensity projection algorithm, and then determine a leftmost boundary position, a rightmost boundary position and an uppermost boundary position based on the thoracic contour image, and further determine a reconstruction center. A multi-phase reconstruction may be performed according to the reconstruction center and a preset field of view for reconstruction, to obtain the cardiac images. By determining the heart region first and performing multi-phase reconstruction according to the image data of heart region, the amount of data used for reconstruction and the time for importing the data can be reduced, and the operation efficiency can be improved.

According to a further aspect of the present disclosure, in cardiac image reconstruction, a phase of interest may be determined for a specific cardiac cycle, and accordingly, the reconstructed cardiac image(s) of the phase of interest may have relatively low artifact(s) and high image quality. According to a still further aspect of the present disclosure, a relatively small field of view (FOV) may be used in cardiac image reconstruction, and accordingly, the operation efficiency may be improved. Specifically, the relatively small FOV may be used in the reconstruction of the cardiac image(s) for the determination of the mean phase or phase of interest, or the relatively small FOV may be used in the reconstruction of cardiac image(s) of interest after the mean phase or phase of interest is determined. The system and method may reduce the artifacts induced by cardiac motion, reduce the amount of data used for reconstruction and the time for importing the data, improve the image quality of the reconstructed cardiac images, and improve the operation efficiency.

In order to make the objects, technical solutions and advantages of the present disclosure more clear, the present disclosure will be further described in detail below with reference to the accompanying drawings and embodiments. It is understood that the specific embodiments described herein are merely illustrative of the present disclosure and are not intended to limit the present disclosure.

A computed tomography (CT) device may include a gantry, a scanning bed, and a console for the physician to operate. A tube may be disposed on one side of the gantry, and detectors may be disposed on a side opposite to the tube. The console may include a computing device that controls CT scanning. The computing device may be also used to receive scan data collected by the detectors, process the scan data and reconstruct CT image(s). When scanning with CT, a patient may lie on the scanning bed, and the patient may be translated into the aperture of the gantry by the scanning bed. The tube disposed on the gantry may emit X-rays, and the X-rays may be received by the detectors to generate scan data. The scan data may be transmitted to the computing device, and the computing device may perform preliminary processing on the scan data and image reconstruction to obtain CT image(s).

It should be noted that a relative position, e.g., left, right, upper, lower or underneath, or the like in the present disclosure may refer to the relative positions in the image(s). For example, an upper position in an image may be closer to the upper boundary of the image than the lower position; a lower position in the image may be closer to the lower boundary of the image than the upper position. A left position in an image may be closer to the left boundary of the image than the right position; a right position in an image may be closer to the right boundary of the image than the left position. Furthermore, the sagittal axis (also referred to as the Y axis) may refer to the horizontal line in the anterior to posterior direction, the coronal (frontal) axis (also referred to as the X axis) may refer to the horizontal line in the left (of the object) to right (of the object) direction, and the vertical axis (also referred to as the Z axis) may refer to the perpendicular line in the superior to inferior direction, which is perpendicular to the horizontal line. And the sagittal plane may refer to the tangent plane along with the sagittal axis and vertical axis, which may segment the object into left and right sections; the coronal (frontal) plane may refer to the tangent plane along with the coronal (frontal) axis and vertical axis, which may segment the object into anterior and posterior sections; and the transverse plane may refer to the tangent plane along with the sagittal axis and coronal (frontal) axis, which may segment the object into superior and inferior sections.

Figure 1:
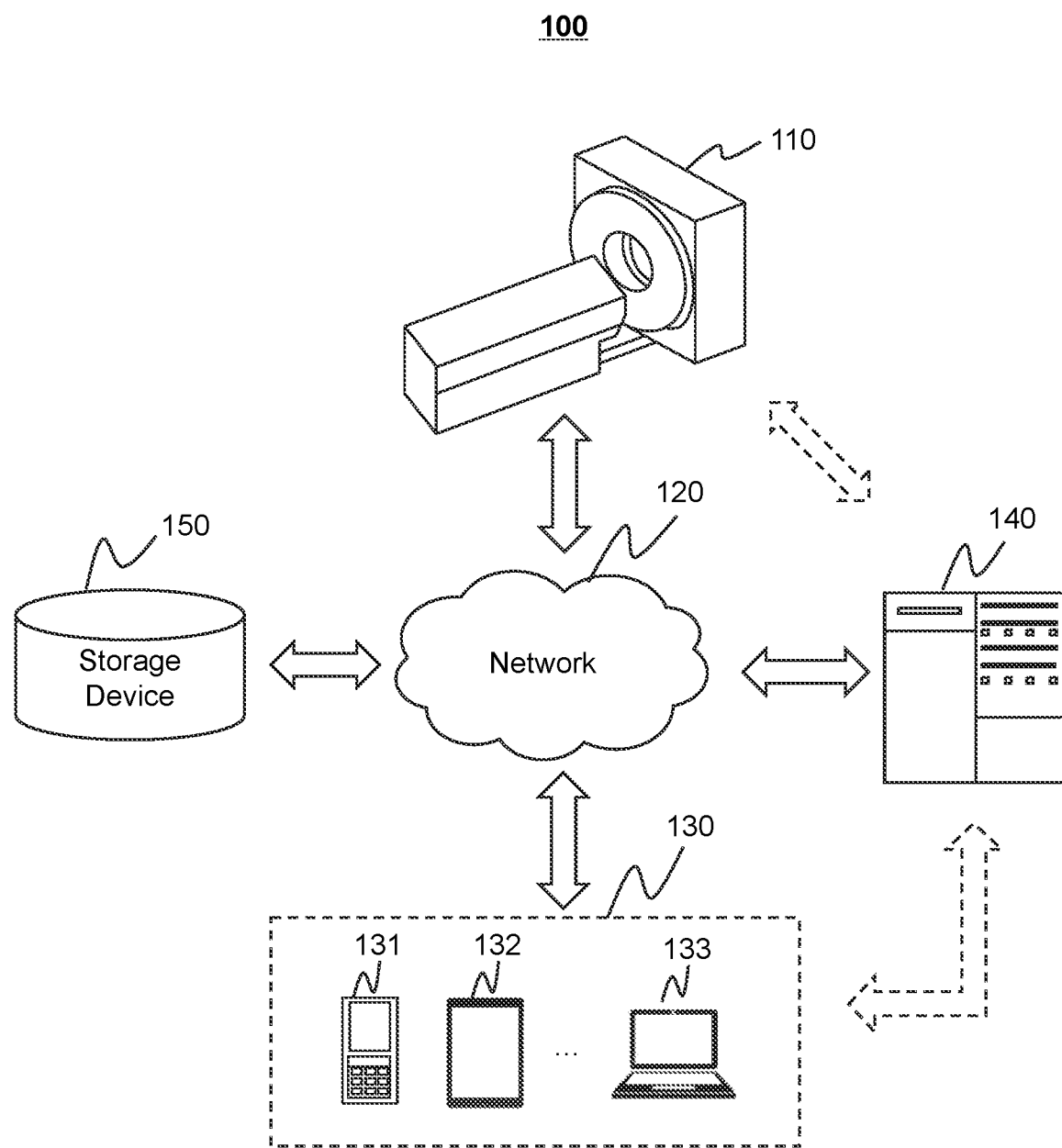
FIG. 1 is a schematic diagram illustrating an exemplary imaging system according to some embodiments of the present disclosure.

FIG. 1 is a schematic diagram illustrating an exemplary imaging system according to some embodiments of the present disclosure. As shown in FIG. 1, the imaging system 100 may include a scanner 110, a network 120, one or more terminals 130, a processing device 140, and a storage device 150. The components in the imaging system 100 may be connected in one or more of various ways. Merely by way of example, the scanner 110 may be connected to the processing device 140 through the network 120. As another example, the scanner 110 may be connected to the processing device 140 directly as indicated by the bi-directional arrow in dotted lines linking the scanner 110 and the processing device 140. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120.

The scanner 110 may scan an object and/or generate scan data relating to the object. In some embodiments, the scanner 110 may be a single-modality medical imaging device (e.g., a magnetic resonance imaging (MRI) device, a positron emission tomography (PET) device, a single-photon emission computed tomography (SPECT) device, a computed tomography (CT) device, or the like) or a multi-modality medical imaging device (e.g., a PET-MRI device, a SPECT-MRI device, or a PET-CT device). In some embodiments, the scanner 110 may include a gantry configured to imaging the object, a detection region configure to accommodate the object, and/or a scanning bed configured to support the object during an imaging process. The scanning bed may support the object during scanning. For example, the object may be supported and/or delivered to the detection region of the gantry by the scanning bed. In some embodiments, the scanner 110 may transmit image(s) via the network 120 to the processing device 140, the storage device 150, and/or the terminal(s) 130. For example, the image(s) may be sent to the processing device 140 for further processing or may be stored in the storage device 150.

In some embodiments, the object may be biological or non-biological. Merely by way of example, the object may include a patient, an organ, a tissue, a specimen, a man-made object, a phantom, etc. In some embodiments, the object to be scanned (also referred to as imaged) may include a body, substance, or the like, or any combination thereof. In some embodiments, the object may include a specific portion of a body, such as a head, a thorax, an abdomen, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc. In the present disclosure, "object" and "subject" are used interchangeably.

The network 120 may include any suitable network that can facilitate the exchange of information and/or data for the imaging system 100. In some embodiments, one or more components of the imaging system 100 (e.g., the scanner 110, the terminal 130, the processing device 140, the storage device 150, etc.) may communicate information and/or data with one or more other components of the imaging system 100 via the network 120. For example, the processing device 140 may obtain image data from the scanner 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the scanner 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information and/or data stored in the scanner 110, the terminal 130, and/or the storage device 150 via the network 120. As another example, the processing device 140 may be directly connected to the scanner 110, the terminal 130 and/or the storage device 150 to access stored information and/or data. As a further example, the processing device 140 may process the data obtained from the scanner 110, and reconstruct cardiac images. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2. In some embodiments, the processing device 140, or a portion of the processing device 140 may be integrated into the scanner 110.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include mass storage, removable storage, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the imaging system 100 (e.g., the processing device 140, the terminal 130, etc.). One or more components of the imaging system 100 may access the data or instructions stored in the storage device 150 via the network 120. In some embodiments, the storage device 150 may be directly connected to or communicate with one or more other components of the imaging system 100 (e.g., the processing device 140, the terminal 130, etc.). In some embodiments, the storage device 150 may be part of the processing device 140.

FIG. 2 is a schematic diagram illustrating exemplary hardware and software components of a computing device according to some embodiments of the present disclosure. The computing device 200 may be a general purpose computer or a special purpose computer; both may be used to implement an imaging system 100 of the present disclosure. In some embodiments, the processing device 140 may be implemented on the computing device 200, via its hardware, software program, firmware, or a combination thereof. Although only one such computer is shown, for convenience, the computer functions as described herein may be implemented in a distributed manner on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processor in accordance with techniques described herein. The computer instructions may include, for example, routines, programs, objects, components, data structures, procedures, modules, and functions, which perform particular functions described herein. For example, the processor 210 may obtain a plurality of projection data generated by an imaging device (e.g., the scanner 110). In some embodiments, the processor 210 may reconstruct, in an initial field of view (FOV), at least one preview image based on at least a portion of the plurality of projection data. In some embodiments, the processor 210 may determine a reconstruction center based on one or more positions of a thoracic contour boundary associated with the at least one preview image. In some embodiments, the processor 210 may select a plurality of cardiac motion phases. In some embodiments, the processor 210 may reconstruct, in a preset FOV smaller than the initial FOV and at the reconstruction center, one or more cardiac images of the each selected cardiac motion phase based on the one or more sub-sets of projection data corresponding to the each selected cardiac motion phase. In some embodiments, the processor 210 may determine a phase of interest based on a plurality of cardiac motion parameters corresponding to the plurality of selected cardiac motion phases. In some embodiments, the processor 210 may reconstruct a target cardiac image of the phase of interest.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the scanner 110, the terminal 130, the storage device 150, and/or any other component of the imaging system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for scanning the heart of the object and/or a program for reconstructing cardiac images.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the scanner 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
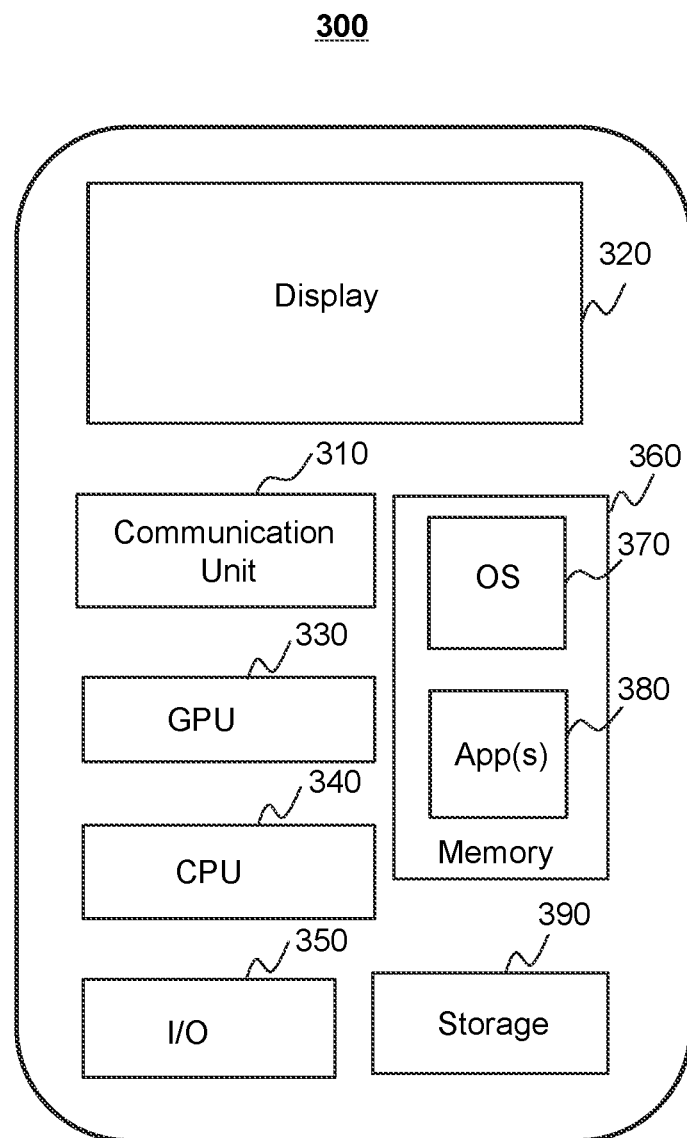
FIG. 3 is a schematic diagram illustrating exemplary hardware and/or software components of an exemplary mobile device that is configured to implement a specific system disclosed in the present disclosure.

FIG. 3 is a schematic diagram illustrating exemplary hardware and/or software components of an exemplary mobile device that is configured to implement a specific system disclosed in the present disclosure. As illustrated in FIG. 3, the mobile device 300 may include a communication unit 310, a display 320, a graphics processing unit (GPU) 330, a CPU 340, an I/O 350, a storage 390, and a memory 360. In some embodiments, any other suitable component, including but not limited to a system bus or a controller (not shown), may also be included in the mobile device 300. In some embodiments, a mobile operating system 370 (e.g., IOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120. In some embodiments, a user may input parameters to the imaging system 100, via the mobile device 300.

In order to implement various modules, units and their functions described above, a computer hardware platform may be used as hardware platforms of one or more elements (e.g., the processing device 140 and/or other components of the imaging system 100 described in FIG. 1). Since these hardware elements, operating systems and program languages are common; it may be assumed that persons skilled in the art may be familiar with these techniques and they may be able to provide information needed in the imaging according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computing device.

Figure 4:
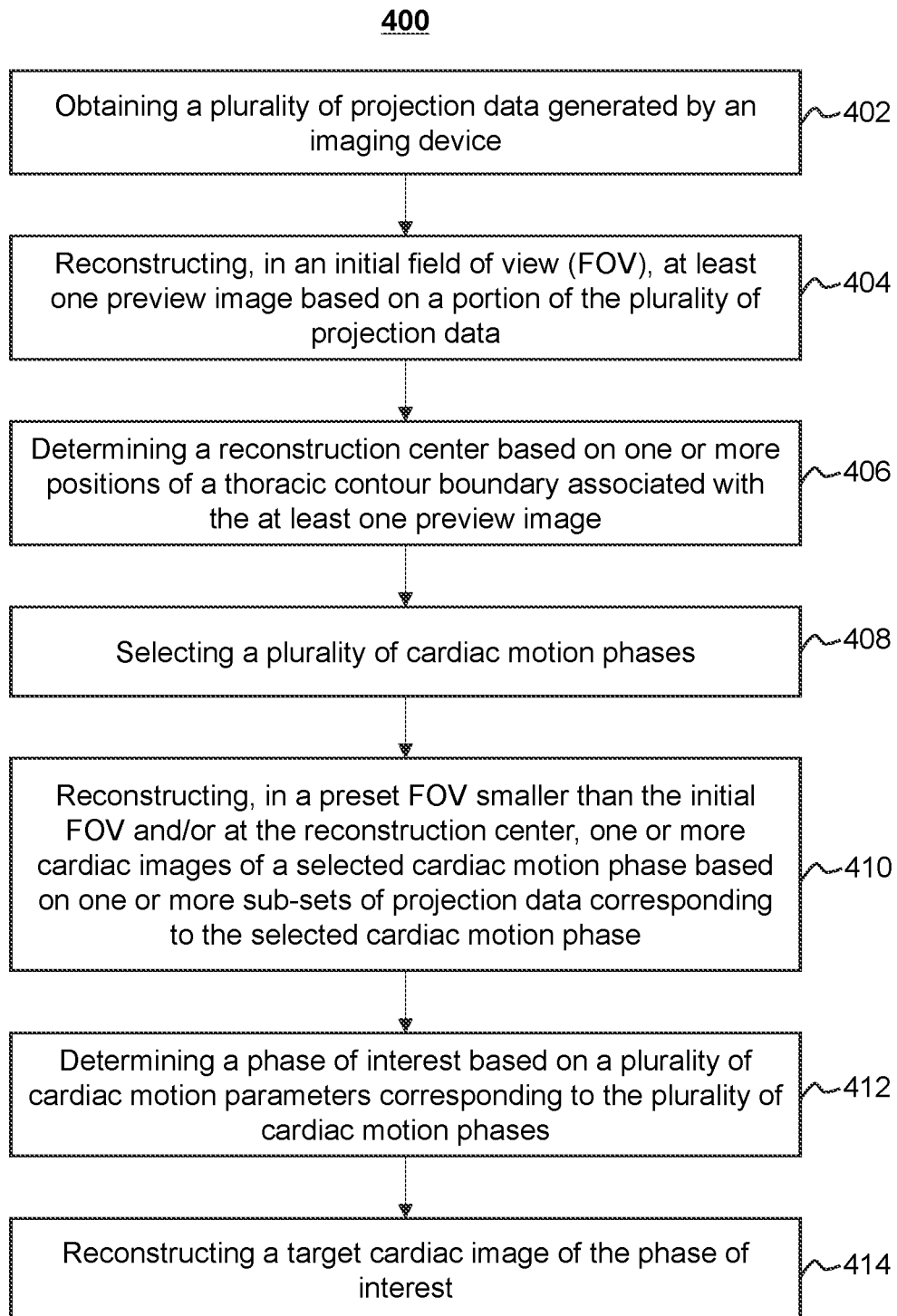
FIG. 4 is a flowchart illustrating an exemplary process for reconstructing one or more target cardiac images according to some embodiments of the present disclosure.

FIG. 4 is a flowchart illustrating an exemplary process for reconstructing one or more target cardiac images according to some embodiments of the present disclosure. Each image of the one or more target cardiac images may include a plurality of elements, each element of the plurality of elements may be a pixel or voxel. In some embodiments, the one or more target cardiac images may correspond to volume data of the heart of an object.

In some embodiments, the process 400 may be executed by the imaging system 100. For example, the process 400 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 400 presented below are intended to be illustrative. In some embodiments, the process may be accomplished with one or more additional operations not described, and/or without one or more of the operations discussed. Additionally, the order in which the operations of the process 400 as illustrated in FIG. 4 and described below is not intended to be limiting.

In 402, a plurality of projection data may be obtained. The projection data may be generated by an imaging device. The processing device 140 (e.g., the first reconstruction module 17200) may perform operation 402. The projection data may be obtained from the scanner 110, the storage device 150, an external data source, etc. More descriptions of the projection data may be found elsewhere in the present disclosure (e.g., FIG. 5 and descriptions thereof).

In 404, at least one preview image may be reconstructed, in an initial field of view (FOV), based on a portion of the plurality of projection data. The processing device 140 (e.g., the first reconstruction module 17200) may perform operation 404. The initial FOV may be a relatively large FOV (e.g., an FOV with a diameter of at least 500 mm). In some embodiments, the initial FOV may be set according to a default setting of the imaging system 100 or preset by a user or operator via the terminal(s) 130. The preview image(s) may be reconstructed based on one or more reconstruction algorithms illustrated elsewhere in the present disclosure. More descriptions of the preview image(s) may be found elsewhere in the present disclosure (e.g., FIGS. 18, 19 and 21 and descriptions thereof).

In 406, a reconstruction center may be determined based on one or more positions of a thoracic contour boundary associated with the at least one preview image. The processing device 140 (e.g., the center reconstruction module 28300) may perform operation 406. More descriptions of the determination of the position(s) of the thoracic contour boundary and the determination of the reconstruction center may be found elsewhere in the present disclosure (e.g., FIGS. 18, 20 and 21 and descriptions thereof).

In 408, a plurality of cardiac motion phases may be selected. The processing device 140 (e.g., the phase selection module 17100) may perform operation 408. More descriptions of the selection of the cardiac motion phase(s) may be found elsewhere in the present disclosure (e.g., FIG. 5 and descriptions thereof).

In 410, one or more cardiac images of a (e.g., each) selected cardiac motion phase (or sampled cardiac motion phase illustrated elsewhere in the present disclosure) may be reconstructed, in a preset FOV smaller than the initial FOV and/or at the reconstruction center, based on one or more sub-sets of projection data corresponding to the selected cardiac motion phase. The processing device 140 (e.g., the image reconstruction module 28400) may perform operation 410. The reconstruction of the cardiac image(s) of the selected cardiac motion phase(s) may be similar to the reconstruction of the target cardiac image(s) illustrated in operations 18108 (see FIG. 18) and 21418 (see FIG. 21). More descriptions of the preset FOV may be found elsewhere in the present disclosure (e.g., FIGS. 18 and 21 and descriptions thereof). More descriptions of the image reconstruction in the preset FOV smaller than the initial FOV and/or at the reconstruction center may be found elsewhere in the present disclosure (e.g., FIG. 21 and descriptions thereof).

In 412, a phase of interest may be determined based on a plurality of cardiac motion parameters corresponding to the plurality of cardiac motion phases. The processing device 140 (e.g., the second reconstruction module 17500) may perform operation 412. More descriptions of the determination of the phase of interest may be found elsewhere in the present disclosure (e.g., FIGS. 5 and 13 and descriptions thereof).

In 414, a target cardiac image of the phase of interest may be reconstructed or determined. The processing device 140 (e.g., the second reconstruction module 17500) may perform operation 414. More descriptions of the reconstruction or determination of the target cardiac image of the phase of interest may be found elsewhere in the present disclosure (e.g., FIG. 13 and descriptions thereof).

According to the process 400, in cardiac image reconstruction, a phase of interest may be determined for a specific cardiac cycle, and accordingly, the reconstructed cardiac image(s) of the phase of interest may have relatively low artifact(s) and high image quality. Besides, a relatively small field of view (FOV) may be used in cardiac image reconstruction, and accordingly, the operation efficiency may be improved. It should be noted that the relatively small FOV may be used in the reconstruction of the cardiac image(s) for the determination of the mean phase or phase of interest, or the relatively small FOV may be used in the reconstruction of cardiac image(s) of interest after the mean phase or phase of interest is determined. That is, in some embodiments, cardiac images of sampled cardiac motion phase(s) may be reconstructed based on the initial FOV, the phase of interest (or mean phase alternatively) may be determined based on the cardiac motion parameters of the cardiac images, and then the target cardiac image of the phase of interest (or mean phase alternatively) may be determined based on the preset FOV and/or the reconstruction center. The operations may reduce the artifacts induced by cardiac motion, reduce the amount of data used for reconstruction and the time for importing the data, improve the image quality of the reconstructed cardiac images, and improve the operation efficiency.

It should be noted that the description of the following processes is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more of the operations in FIG. 5 (or any one of FIGS. 6-16) may be performed based on images reconstructed based on the initial FOV. As another example, one or more of the operations in FIG. 5 (or any one of FIGS. 6-16) may be performed based on images reconstructed based on the preset FOV and/or reconstruction center.

Figure 5A:
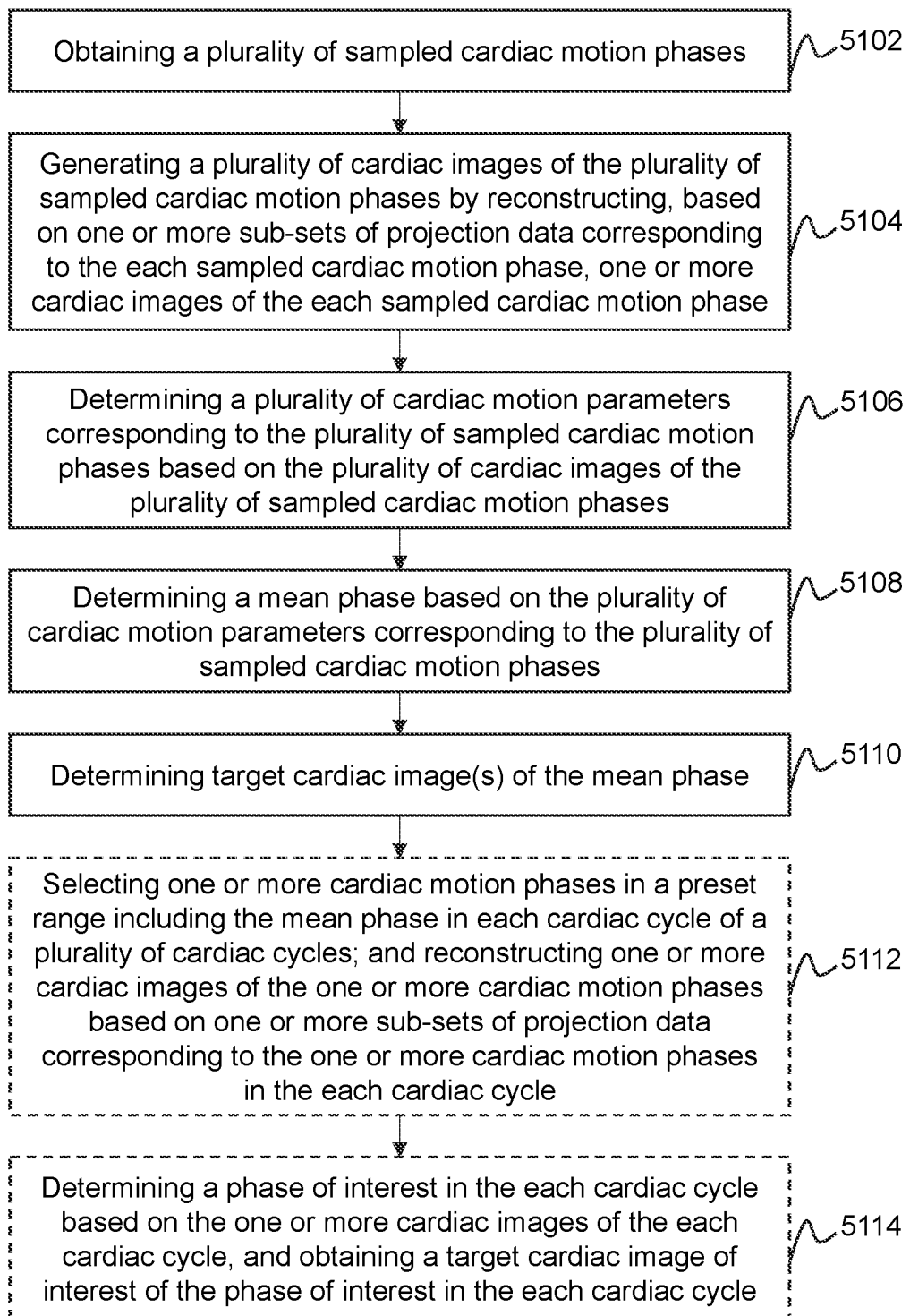
FIG. 5A is a flowchart illustrating an exemplary process for reconstructing cardiac images according to some embodiments of the present disclosure.

FIG. 5A is a flowchart illustrating an exemplary process for reconstructing cardiac images according to some embodiments of the present disclosure. In some embodiments, the process 500 may be executed by the imaging system 100. For example, the process 500 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 500 presented below are intended to be illustrative. In some embodiments, the process may be accomplished with one or more additional operations not described, and/or without one or more of the operations discussed. Additionally, the order in which the operations of the process 500 as illustrated in FIG. 5 and described below is not intended to be limiting.

In an embodiment, as shown in FIG. 5, an exemplary cardiac image reconstruction process is provided. The process 500 may include the following operations:

In 5102, a plurality of sampled cardiac motion phases may be obtained (e.g., at regular intervals).

Figure 5B:
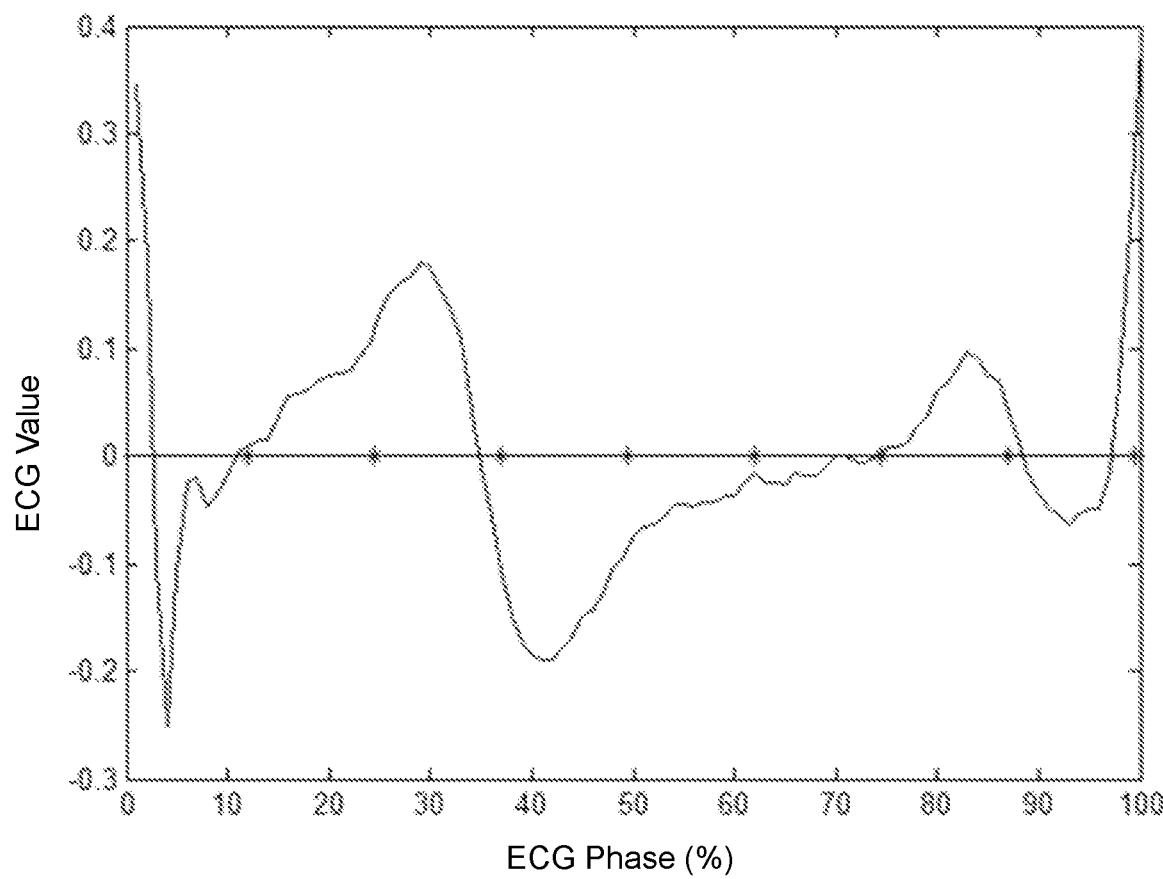
FIG. 5B is a schematic diagram illustrating an exemplary ECG signal and corresponding phases according to some embodiments of the present disclosure.

In some embodiments, the processing device 140 (e.g., the phase selection module 17100) may perform operation 5102. In some embodiments, cardiac motion phases may be denoted by phase angles (e.g., phase angles from 0° to 360°). In some embodiments, cardiac motion phases may be denoted by percentage values (e.g., percentage values between 0%-100% as illustrated in FIG. 5B). A phase x % may correspond to a phase angle x %*360°. In some embodiments, the plurality of sampled cardiac motion phases may be obtained at regular intervals (e.g., an interval of 1%, 2%, 5%, 10%, 15%, 20%, 25%, etc.). For example, regular intervals may be intervals of 3%, 6%, 9%, 12%, 15%, 18%, 21%, etc. In some embodiments, the plurality of sampled cardiac motion phases may be obtained at random intervals, irregular intervals, or by a certain preset rule which may be determined by a user or the imaging system 100. For example, the plurality of sampled cardiac motion phases may be obtained at the random intervals from 1% to 100%. As another example, the plurality of sampled cardiac motion phases may be obtained at different intervals for different cardiac cycles.

Specifically, the electrocardiogram (ECG) may refer to a graph of voltage versus time. The voltage may be detected from a body surface of the object by an electrocardiograph. The ECG may reflect changes in bioelectricity caused by the excitement of the pacemaker, the atria, and the ventricle of the heart of the object in each cardiac cycle. Phases of the ECG may indicate the state of the heart in the current cardiac cycle. The heart's ECG may be divided into a plurality of cycles (i.e., the cardiac cycles) based on an R wave of the ECG. If a current phase is around 45% of the current cardiac cycle, the heart is usually in systole. If the phase is around 75% of the current cardiac cycle, the heart is usually in diastole. The R wave may correspond to the ventricular end-diastole.

FIG. 5B is a schematic diagram illustrating an exemplary ECG signal and corresponding phases according to some embodiments of the present disclosure. As illustrated in FIG. 5B, a cardiac cycle may include a period from the beginning of a first Rtag (which represents the position of the R wave) to the end of a second Rtag next to the first Rtag. In some embodiments, a cardiac cycle may be divided into 100 phases from 1% to 100%. As illustrated in FIG. 5B, a exemplary regular interval of the sampled cardiac motion phases may be 12.5%, and 8 sampled cardiac motion phases including 12.5%, 25%, 37.5%, 50%, 62.5%, 75%, 87.5%, and 100% may be obtained. Then imaging data of the 8 sampled cardiac motion phases may be reconstructed. In FIG. 5B, the abscissa axis coordinates denote the ECG phases with the unit of percentage, and the vertical axis coordinates denote the ECG values with the unit of millivolt. The first Rtag and the second Rtag correspond to points with abscissas of 0% and 100%, respectively. The points labelled by asterisks on the abscissa axis correspond to the 8 sampled cardiac motion phases.

A CT scanner may scan the object continuously for a period of time and obtain scan data. That is, in a cardiac cycle, each phase may correspond to a data set collected by the CT scanner, and 100 phases in a phase range of 1%-100% may have corresponding data sets in each cardiac cycle. A plurality of cardiac motion phases may be selected at regular intervals. For example, ten phases including 10%, 20%, 30%, 40%, 50%, 60%, 70%, 80%, 90%, and 100% may be selected.

In some embodiments, the plurality of sampled cardiac motion phases may refer to the plurality of selected cardiac motion phases.

In 5104, a plurality of cardiac images of the plurality of sampled cardiac motion phases may be generated.

In some embodiments, the processing device 140 (e.g., the first reconstruction module 17200) may perform operation 5104. In some embodiments, the cardiac images of the plurality of sampled cardiac motion phases may be generated by reconstructing one or more cardiac images of the each sampled cardiac motion phase. In some embodiments, a plurality of projection data may be generated by an imaging device (e.g., the scanner 110). The plurality of projection data may include a plurality of sub-sets of projection data. In some embodiments, each sub-set of projection data may correspond to a cardiac motion phase. In some embodiments, the cardiac images of the each sampled cardiac motion phase may be reconstructed based on one or more sub-sets of projection data corresponding to the each sampled cardiac motion phase. In some embodiments, the plurality of cardiac images may include cardiac images in a transverse section. In some embodiments, a first portion of the plurality of cardiac images may illustrate a first portion of the object, while a second portion of the plurality of cardiac images may illustrate a second portion of the object. For example, one or more images may show a first layer of the heart (or chest); one or more images may show a second layer of the heart (or chest); one or more images may show a third layer of the heart (or chest); one or more images may show a fourth layer of the heart (or chest), etc. The thickness of a layer of the heart (or chest) may be 1 cm, 2 cm, 3 cm, etc. In some embodiments, the thickness may be adjusted according to the needs or the default setting of the imaging system 100. In some embodiments, the cardiac images may be reconstructed using one or more reconstruction algorithms including, for example, Filtered Back-Projection (FBP), Algebraic Reconstruction Technique (ART), Local Reconstruction Algorithm (Local RA), and ordered-subset expectation maximization (OSEM), etc.

Specifically, in some embodiments, the images of the plurality of phases may be reconstructed according to the scan data of the selected cardiac motion phases. For example, images of ten phases including 10%, 20%, 30%, 40%, 50%, 60%, 70%, 80%, 90%, and 100% may be reconstructed. Generally, multiple tomographic images of multiple positions of the heart may be generated by cardiac CT scanning. Therefore, the image(s) corresponding to each phase may refer to an image of a specific position of the heart corresponding to the each phase, or a sequence of images including multiple images of multiple positions corresponding to the each phase.

In 5106, a cardiac motion parameter corresponding to the each sampled cardiac motion phase may be determined.

In some embodiments, the processing device 140 (e.g., the cardiac motion parameter determination module 17300)

may perform operation 5106. In some embodiments, a plurality of cardiac motion parameters may be determined based on the plurality of cardiac images of the plurality of sampled cardiac motion phases. In some embodiments, a sampled cardiac motion phase may correspond to one or more cardiac images (i.e., the one or more cardiac images may have a same sampled cardiac motion phase), and a cardiac motion parameter may be determined based on each cardiac image of the one or more cardiac images, and thus, one or more cardiac motion parameters corresponding to the sampled cardiac motion phase may be determined. In some embodiments, a mean cardiac motion parameter corresponding to the sampled cardiac motion phase may be determined based on the one or more cardiac motion parameters.

In some embodiments, a cardiac motion parameter may refer to a parameter describing the cardiac motion. Exemplary cardiac motion parameters may include a cardiac motion rate, a cardiac motion intensity, etc. The cardiac motion rate may include a blood flow rate in a blood vessel of the heart, a muscle contraction rate of a cardiac muscle, etc. The cardiac motion intensity may include a magnitude of vasoconstriction, a magnitude of vasodilation, a heartbeat amplitude, etc. In some embodiments, the cardiac motion parameter may refer to a parameter associated with the cardiac motion rate or the cardiac motion intensity. For example, the parameter may be the cardiac motion rate (or the cardiac motion intensity) multiplied by a coefficient. As another example, the parameter may relate to a reciprocal of the cardiac motion rate (or the cardiac motion intensity). In some embodiments, if the cardiac motion parameter is relatively large, the cardiac motion may be relatively pronounced. In some embodiments, if the cardiac motion parameter is relatively small, the cardiac motion may be relatively pronounced. More descriptions of the determination of the cardiac motion parameters may be found elsewhere in the present disclosure (e.g., FIG. 11 and descriptions thereof).

Specifically, in some embodiments, mean absolute difference(s) (MAD(s)) between the images of two adjacent sampled cardiac motion phases may be determined according to the images of the two adjacent phases and the sizes of the image matrices corresponding to the images. The cardiac motion parameters of the plurality of sampled cardiac motion phases may be determined based on the MAD(s) between the images of two adjacent phases. In some embodiments, a set of initial cardiac images of interest may be determined according to the images corresponding to the plurality of sampled cardiac motion phases, an average cardiac rate, and/or a standard deviation of cardiac rates; vascular images of interest may be extracted from the set of initial cardiac images of interest; motion rates of a vascular center of a blood vessel (in the vascular images of interest) between the plurality of sampled cardiac motion phases may be determined according to the vascular images of interest; and the motion rates of the vascular center of the blood vessel may be designated as the cardiac motion parameter.

In some embodiments, two adjacent sampled cardiac motion phases may refer to two sampled cardiac motion phases next to each other without another sampled cardiac motion phase in between in a phase set. For example, as illustrated in FIG. 5B, the sampled cardiac motion phase 12.5% and the sampled cardiac motion phase 25% are two adjacent sampled cardiac motion phases, i.e., the sampled cardiac motion phase 12.5% and the sampled cardiac motion phase 25% are adjacent to each other. As another example, the sampled cardiac motion phase 25% and the sampled cardiac motion phase 37.5% in FIG. 5B are two adjacent sampled cardiac motion phases, i.e., the sampled cardiac motion phase 25% and the sampled cardiac motion phase 37.5% are adjacent to each other.

In 5108, a mean phase may be determined based on the plurality of cardiac motion parameters corresponding to the plurality of sampled cardiac motion phases.

In some embodiments, the processing device 140 (e.g., the mean phase determination module 17400) may perform operation 5108. In some embodiments, the mean phase may refer to a relatively optimal phase (in which the cardiac motion is relatively slight) for the plurality of cardiac cycles (in which the projection data of the object are generated). In some embodiments, cardiac images of the mean phase may have a relatively low level of motion artifacts, a relatively high quality, and/or a relatively high clarity. In some embodiments, the mean phase may be the same as one of the plurality of sampled cardiac motion phases. Alternatively, the mean phase may be different from all the plurality of sampled cardiac motion phases.

For example, if the plurality of sampled cardiac motion phases include eight phases (see FIG. 5B): $p_1$ (e.g., 12.5%), $p_2$ (e.g., 25%), $p_3$ (e.g., 37.5%), $p_4$ (e.g., 50%), $p_5$ (e.g., 62.5%), $p_6$ (e.g., 75%), $p_7$ (e.g., 87.5%), and $p_8$ (e.g., 100%), and each of the plurality of cardiac cycles has the eight sampled cardiac motion phases, then eight cardiac motion parameters corresponding to the eight sampled cardiac motion phases may be determined for the cardiac cycles. Furthermore, the mean phase (e.g., 45%, 50%, 75%, etc.) may be determined based on the eight cardiac motion parameters corresponding to the eight sampled cardiac motion phases for the cardiac cycles. More descriptions of the determination of the mean phase may be found elsewhere in the present disclosure (e.g., FIGS. 6 and 12 and descriptions thereof).

Specifically, in some embodiments, the mean phase may be determined according to the cardiac motion parameters of the plurality of sampled cardiac motion phases. In some embodiments, the mean phase may be determined based on the motion rates of the vascular center of the blood vessel between the plurality of sampled cardiac motion phases.

In 5110, target cardiac image(s) of the mean phase may be determined.

In some embodiments, the processing device 140 (e.g., the second reconstruction module 17500) may perform operation 5110. In some embodiments, the target cardiac image(s) of the mean phase may have a relatively low level of motion artifacts, a relatively high quality, and/or a relatively high clarity.

Specifically, in some embodiments, according to the mean phase, the target cardiac image(s) may be selected from the plurality of cardiac images corresponding to the plurality of sampled cardiac motion phases that have been reconstructed. In some embodiments, the scan data corresponding to the mean phase may be selected from the plurality of projection data, and the target cardiac image(s) corresponding to the mean phase may be reconstructed according to the scan data. The target cardiac image(s) may refer to a cardiac image of a specific position of the heart corresponding to the mean phase, or a sequence of images including multiple cardiac images of multiple positions of the heart corresponding to the mean phase.

In comparison with a process in which a preset phase is selected and an image of the preset phase is reconstructed, the process 500 provided in this embodiment may determine a mean phase according to a specific situation of each scan of a patient, and the mean phase may be suitable for reconstructing an image for the each scan. The reconstructed image corresponding to the mean phase may have a relatively high quality with a relatively low level of motion artifacts of the heart.

Alternatively or additionally, in order to further reduce motion artifacts and improve image quality, the following operations may be added to the process 500:

In 5112, one or more cardiac motion phases may be selected in a preset range in each cardiac cycle of the plurality of cardiac cycles. The preset range may include the mean phase. One or more cardiac images of the one or more cardiac motion phases may be reconstructed based on one or more sub-sets of projection data corresponding to the one or more cardiac motion phases in the each cardiac cycle.

In some embodiments, the processing device 140 (e.g., the second reconstruction module 17500) may perform operation 5112. In some embodiments, the cardiac motion phases selected in the preset range may include part or all of the phases in the preset range. For example, if the mean phase is 45%, and the preset range is 40%-50%, then the cardiac motion phase(s) in the preset range 40%-50% may be selected (e.g., 41%, 42%, 43%, 44%, 45%, 46%, 47%, 48%, 49%, 50%).

In some embodiments, the preset range may be 5%, 10%, 20% (or the like) around the mean phase. For example, in each cardiac cycle, phases within 10% around the mean phase may be selected, and images corresponding to the phases within 10% around the mean phase in each cardiac cycle may be reconstructed.

Merely by way of example, if the mean phase is M %, and the preset range is 2N %, then the cardiac motion phases from (M−N) % to (M+N) % (i.e., phases within 2N % around the mean phase) may be selected.

In 5114, a phase of interest may be determined in the each cardiac cycle based on the one or more cardiac images of the each cardiac cycle, and a target cardiac image of interest of the phase of interest may be obtained in the each cardiac cycle. Therefore, a sequence of target cardiac images of interest of the phases of interest may be obtained for the plurality of cardiac cycles.

In some embodiments, the processing device 140 (e.g., the second reconstruction module 17500) may perform operation 5114. The phase of interest may refer to a relatively optimal phase (in which the cardiac motion is relatively slight) for the each cardiac cycle. The phases of interest for different cardiac cycles may be the same or different. The phase of interest may be the same as or different from the mean phase. For example, a phase of interest in a first cardiac cycle may be the same as the mean phase. As another example, a phase of interest in a second cardiac cycle may be less than the mean phase. As a further example, a phase of interest in a third cardiac cycle may be larger than the mean phase. In some embodiments, a first cardiac motion phase in a first cardiac cycle of the plurality of cardiac cycles may be determined according to the process 500. In some embodiments, a second cardiac motion phase in a second cardiac cycle of the plurality of cardiac cycles may be determined according to the process 500. In some embodiments, the second cardiac motion phase may be different from the first cardiac motion phase. In some embodiments, a first cardiac image of the first cardiac motion phase in the first cardiac cycle of the plurality of cardiac cycles may be reconstructed. In some embodiments, a second cardiac image of the second cardiac motion phase in the second cardiac cycle of the plurality of cardiac cycles may be reconstructed. More descriptions of the determination of the phase of interest may be found elsewhere in the present disclosure (e.g., FIG. 14 and descriptions thereof).

According to the embodiment, the phase of interest for each cardiac cycle may be determined on the basis of the mean phase, and a target cardiac image of interest corresponding to the phase of interest may be obtained in each cardiac cycle, and thus, a sequence of target cardiac images of interest may be obtained. Each image in the sequence of target cardiac images of interest may have a relatively low level of motion artifacts and a relatively high quality.

For example, projection data of a plurality cardiac cycles may be obtained. For each cardiac cycle, the processing device 140 may obtain eight sampled cardiac motion phases (see FIG. 5B): $p_1$ (e.g., 12.5%), $p_2$ (e.g., 25%), $p_3$ (e.g., 37.5%), $p_4$ (e.g., 50%), $p_5$ (e.g., 62.5%), $p_6$ (e.g., 75%), $p_7$ (e.g., 87.5%), and $p_8$ (e.g., 100%). And the processing device 140 may generate cardiac images corresponding to the eight sampled cardiac motion phases by reconstructing the eight cardiac images in each cardiac cycle. The processing device 140 may determine a cardiac motion parameter corresponding to each of the eight sampled cardiac motion phases based on the cardiac images. Then the processing device 140 may determine a mean phase based on the eight cardiac motion parameters, and determine target cardiac images of the mean phase. Furthermore, in some embodiments, the processing device 140 may select one or more cardiac motion phases in a preset range around the mean phase in each cardiac cycle, and reconstruct the cardiac image(s) corresponding to the selected cardiac motion phases. The processing device 140 may determine a phase of interest in each cardiac cycle based on the cardiac images and obtain a target cardiac image of interest of the phase of interest.

In some embodiments, a heart may be further reconstructed based on the sequence of target cardiac images of interest. Because each image in the sequence of target cardiac images of interest may have a relatively low level of motion artifacts and a relatively high quality, the reconstructed heart may have a relatively high quality, which can facilitate further diagnoses.

It should be noted that, additionally or alternatively, in some embodiments, the mean phase or the phase of interest may also be determined based on the image qualities of the cardiac images. In some embodiments, the image qualities of the cardiac images may be determined according to a vessel assessment of the vessel(s) in the cardiac images. More descriptions of the vessel assessment and the determination of the mean phase or the phase of interest may be found in, e.g., Chinese Patent Application No. 201811134373.2 entitled "METHODS, APPARATUS, COMPUTING DEVICES AND STORAGE MEDIUMS FOR IMAGE QUALITY ASSESSMENT," filed Sep. 27, 2018, Chinese Patent Application No. 201811134375.1 entitled "METHODS, APPARATUS, COMPUTING DEVICES AND STORAGE MEDIUMS FOR IMAGE RECONSTRUCTION," filed Sep. 27, 2018, and U.S. application Ser. No. 16/437,006 20618-0391 US00), entitled "SYSTEMS AND METHODS FOR EVALUATING IMAGE QUALITY," filed Jun. 11, 2019, the contents of which are hereby incorporated by reference.

FIG. 6 is a flowchart illustrating an exemplary process for determining a mean phase according to some embodiments of the present disclosure. In some embodiments, operation 5106 illustrated in FIG. 5 may be performed according to operations 6202 and 6204 in the process 600. In some embodiments, the process 600 may be executed by the imaging system 100. For example, the process 600 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 600 presented below are intended to be illustrative. In some embodiments, the process may be accomplished with one or more additional operations not described, and/or without one or more of the operations discussed. Additionally, the order in which the operations of the process 600 as illustrated in FIG. 6 and described below is not intended to be limiting.

In an embodiment, as shown in FIG. 6, an exemplary process for determining a mean phase is provided. The process 600 may include the following operations:

In 6202, a plurality of mean absolute differences (MADs) may be obtained by determining an MAD between two cardiac images of each two adjacent sampled cardiac motion phases.

In some embodiments, the processing device 140 (e.g., cardiac motion parameter determination module 17300) may perform operation 6202. In some embodiments, the number or count of the plurality of MADs may be equal to or less than the number or count of the plurality of sampled cardiac motion phases. For example, if the plurality of sampled cardiac motion phases include eight phases (see FIG. 5B): $p_1$ (e.g., 12.5%), $p_2$ (e.g., 25%), $p_3$ (e.g., 37.5%), $p_4$ (e.g., 50%), $p_5$ (e.g., 62.5%), $p_6$ (e.g., 75%), $p_7$ (e.g., 87.5%), and $p_8$ (e.g., 100%), then a first MAD may be determined between two cardiac images of two adjacent sampled cardiac motion phases $p_1$ and $p_2$, a second MAD may be determined between two cardiac images of two adjacent sampled cardiac motion phases $p_2$ and $p_3$, a third MAD may be determined between two cardiac images of two adjacent sampled cardiac motion phases $p_3$ and $p_4$, a fourth MAD may be determined between two cardiac images of two adjacent sampled cardiac motion phases $p_4$ and $p_5$, a fifth MAD may be determined between two cardiac images of two adjacent sampled cardiac motion phases $p_5$ and $p_6$, a sixth MAD may be determined between two cardiac images of two adjacent sampled cardiac motion phases $p_6$ and $p_7$, and a seventh MAD may be determined between two cardiac images of two adjacent sampled cardiac motion phases $p_7$ and ix In some embodiments, an eighth MAD may be determined between two cardiac images of two adjacent sampled cardiac motion phases $p_8$ and $p_1$.

Specifically, in some embodiments, before the MAD between the two cardiac images of the each two adjacent sampled cardiac motion phases is determined, the cardiac images corresponding to the plurality of sampled cardiac motion phases may be preprocessed. In some embodiments, the preprocessing may include: performing image segmentation on the cardiac images of the plurality of sampled cardiac motion phases according to one or more thresholds; and removing one or more regions that are unrelated to cardiac motion to obtain images of one or more regions relating to cardiac motion.

In some embodiments, the threshold(s) may relate to gray levels of pixels or voxels of the cardiac images. In some embodiments, the threshold(s) may be determined by the imaging system 100, or may be preset by a user or operator via the terminal(s) 130.

In an embodiment, the image segmentation of the cardiac images of the plurality of sampled cardiac motion phases based on the threshold(s) may be represented as:

$$A(i, j) = \begin{cases} A & \text{if } A(i, j) > ConThre \\ 0 & \text{if } A(i, j) \le ConThre \end{cases} \quad \text{Equation (1)}$$

where A is a matrix of the gray level(s) of the pixels in a cardiac image of a sampled cardiac motion phase; ConThre is the threshold; $A(i,j)$ is the gray level of a pixel with a coordinate $(i,j)$ in the cardiac image.

In an embodiment, the MAD between the two cardiac images of the each two adjacent sampled cardiac motion phases may be determined as:

$$MAD(A, B) = \frac{1}{Mm.^2 2} \sum_{i}^{Mm} \sum_{j}^{Mm} |A(i, j) - B(i, j)|, \quad \text{Equation (2)}$$

where A and B represent the cardiac images of the each two adjacent sampled cardiac motion phases, respectively; $A(i, j)$ is the gray level of a pixel with a coordinate $(i, j)$ in the image A; $B(i, j)$ is the gray level of a pixel with a coordinate $(i, j)$ in the image B; Mm is the size of the image matrix A and/or B; MAD(A, B) is the mean absolute difference between images A and B.

In 6204, the plurality of cardiac motion parameters corresponding to the plurality of sampled cardiac motion phases may be determined based on the plurality of MADs.

In some embodiments, the processing device 140 (e.g., the cardiac motion parameter determination module 17300) may perform operation 6204.

Specifically, in some embodiments, an MAD between a cardiac image of a sampled cardiac motion phase and a cardiac image of a previous sampled cardiac motion phase may be obtained as a first parameter. In some embodiments, an MAD between a cardiac image of a sampled cardiac motion phase and a cardiac image of a next sampled cardiac motion phase may be obtained as a second parameter. In some embodiments, the first parameter and the second parameter of the same cardiac image may be added to obtain a cardiac motion parameter of the sampled cardiac motion phase.

In some embodiments, the processing device 140 may determine a first MAD between a first cardiac image of a first sampled cardiac motion phase that occurs before the sampled cardiac motion phase and a cardiac image of the sampled cardiac motion phase. In some embodiments, the processing device 140 may determine a second MAD between a second cardiac image of a second sampled cardiac motion phase that occurs after the sampled cardiac motion phase and the cardiac image of the sampled cardiac motion phase. In some embodiments, the processing device 140 may further designate a sum of the first MAD and the second MAD as the cardiac motion parameter corresponding to the sampled cardiac motion phase. In some embodiments, the first sampled cardiac motion phase may be adjacent to the sampled cardiac motion phase. In some embodiments, the second sampled cardiac motion phase may be adjacent to the sampled cardiac motion phase. In some embodiments, the sampled cardiac motion phases (in a same cycle or different cycles) may be arranged based on their respective sequence numbers, e.g., in an ascending order. The sequence number of a sampled cardiac motion phase may be determined based on the timing of the sampled cardiac motion phase in the cycle in which the sampled cardiac motion phase occurs relative to a reference time point of the cycle. Exemplary reference time points of a cycle of the cardiac motion may include the beginning of the cardiac cycle (e.g., the time of contraction of the atria), the end of the cardiac cycle (e.g., the time of ventricular relaxation), or a midpoint of the cardiac cycle (e.g., the beginning of the ventricular systole). Sampled cardiac motion phases that occur in different cycles of cardiac motion may have a same sequence number. If a sequence number of a sampled cardiac motion phase A is lower than a sequence number of a sampled cardiac motion phase B, then the sampled cardiac motion phase A may be considered "occur before" the sampled cardiac motion phase B, and accordingly, the sampled cardiac motion phase B may "occur after" the sampled cardiac motion phase A. If the absolute value of a difference between sequence numbers of two sampled cardiac motion phases C and D is 1, then the sampled cardiac motion phase C and the sampled cardiac motion phase D are considered "adjacent to" each other.

In an embodiment, the determination of the cardiac motion parameter of a sampled cardiac motion phase may be represented as:

$$\Delta M(P_l,k)=MAD(V_k(P_l,i,j),(V_k(P_{l-1},i,j))+MAD(V_k(P_l,i,j),V_k(P_{l+1},i,j)),\quad\text{Equation (3)}$$

where $MAD(V_k(P_l, i, j), V_k(P_{l-1}, i, j))$ is the mean absolute difference between a cardiac image $V_k(P_l, i, j)$ of a current sampled cardiac motion phase and a cardiac image $V_k(P_{l-1}, i, j)$ of a sampled cardiac motion phase that occurs before the current sampled cardiac motion phase; $MAD(V_k(P_l, i, j), V_k(P_{l+1}, i, j))$ is the mean absolute difference between the cardiac image $V_k(P_l, i, j)$ of the current sampled cardiac motion phase and a cardiac image $V_k(P_{l+1}, i, j)$ of a sampled cardiac motion phase that occurs after the current sampled cardiac motion phase; $\Delta M(P_l, k)$ is the cardiac motion parameter corresponding to the cardiac image of the current sampled cardiac motion phase.

In Equation (3), $P_l$ is the current sampled cardiac motion phase, l is a sequence number of the current sampled cardiac motion phase in the plurality of sampled cardiac motion phases, k is a sequence number of a slice of the object, i and j represent the element locations in a corresponding cardiac image. In some embodiments, the number (or count) of the cardiac motion parameters (e.g., the $\Delta M(P_l, k)$ in Equation (3)) may be less than the number (or count) of the sampled cardiac motion phases.

In 6206, a mean phase may be determined based on the plurality of cardiac motion parameters corresponding to the plurality of sampled cardiac motion phases.

In some embodiments, the processing device 140 (e.g., the mean phase determination module 17400) may perform operation 6206.

Specifically, in some embodiments, in a systolic period of cardiac motion, a cardiac motion phase corresponding to a minimum cardiac motion parameter in the systolic period may be designated as the mean phase in the systolic period. In a diastolic period of cardiac motion, a cardiac motion phase corresponding to a minimum cardiac motion parameter in the diastolic period may be designated as the mean phase in the diastolic period.

In some embodiments, the cardiac motion parameter(s) determined based on MAD(s) may represent the difference(s) between cardiac images. A relatively small cardiac motion parameter may represent a relatively small motion amplitude, indicating that the cardiac motion is relatively smooth. Accordingly, the phase corresponding to a minimum motion parameter may be determined as the mean phase, and the cardiac image reconstructed under the mean phase may have less artifact(s).

In some embodiments, in a systolic period of cardiac motion, a cardiac motion phase corresponding to a maximum cardiac motion parameter in the systolic period may be designated as the mean phase in the systolic period. In a diastolic period of cardiac motion, a cardiac motion phase corresponding to a maximum cardiac motion parameter in the diastolic period may be designated as the mean phase in the diastolic period. For example, as illustrated in FIG. 12, a relatively large motion parameter may represent a relatively stable motion state, indicating that the cardiac motion is relatively smooth. Accordingly, the phase corresponding to a maximum motion parameter may be determined as the mean phase, and the cardiac image reconstructed under the mean phase may have less artifact(s). In some embodiments, one or more mean phases may be determined based on the plurality of cardiac motion parameters corresponding to the plurality of sampled cardiac motion phases. For example, a first mean phase may be determined in the systolic period, and a second mean phase may be determined in the diastolic period. In some embodiments, the one or more mean phases may be provided to a user or an operator, and the user or operator may choose a mean phase for cardiac image reconstruction. If two or more mean phases are determined, then two or more preset ranges may be selected, and accordingly, two or more phases of interest may be determined. Specifically, in some embodiments, a preset range may be selected for each mean phase, and a phase of interest may be determined in each preset range. In some embodiments, the phase(s) of interest may be provided to the user or operator, and the user or operator may determine a phase of interest in each cardiac cycle for cardiac image reconstruction.

In some embodiments, the determination of the mean phase in the systolic period may be represented as:

$$P_{Basic}1=\arg_l\min(\Sigma_k^N\Delta M(P_l,k)/N),\text{ for all }P_l\text{ where }P_{1S}\leq P_l\leq P_{1E},\quad\text{Equation (4)}$$

where $P_{Basic}1$ is the mean phase in the systolic period; N is the number (or count) of cardiac images of the sampled cardiac motion phases in the systolic period; $(P_{1S}\leq P_l\leq P_{1E})$ is the range of the sampled cardiac motion phases in the systolic period.

In Equation (4), $P_{1E}$ is the end phase in the systolic period, and $P_{1S}$ is the start phase in the systolic period.

In an embodiment, the determination of the mean phase in the diastolic period may be represented as:

$$P_{Basic}2=\arg_l\min(\Sigma_k^N\Delta M(P_l,k)/N),\text{ for all }P_l\text{ where }P_{2S}\leq P_l\leq P_{2E},\quad\text{Equation (5)}$$

where $P_{Basic}2$ is the mean phase in the diastolic period; N is the number (or count) of cardiac images of the sampled cardiac motion phases in the diastolic period; $(P_{2S}\leq P_l\leq P_{2E})$ is the range of sampled cardiac motion phases in the diastolic period.

In Equation (5), $P_{2E}$ is the end phase in the diastolic period, $P_{2S}$ is the start phase in the diastolic period.

According to the process for determining the mean phase described above, the cardiac motion parameters of the corresponding sampled cardiac motion phases may be determined based on the mean absolute differences between each two cardiac images of each two adjacent sampled cardiac motion phases, and the cardiac motion phase with the minimum (or maximum) cardiac motion parameter may be designated as the mean phase. Therefore, the mean phase may be determined accurately, and the accuracy of the determination of the optimal phase in the cardiac motion may be ensured.

In some embodiments, the cardiac motion parameter described in FIG. 6 may be regarded as a first motion parameter.

FIG. 7 is a flowchart illustrating another exemplary process for determining a mean phase according to some embodiments of the present disclosure. In some embodiments, operation 5106 illustrated in FIG. 5 may be performed according to the process 700. In some embodiments, the process 700 may be executed by the imaging system 100. For example, the process 700 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 700 presented below are intended to be illustrative. In some embodiments, the process may be accomplished with one or more additional operations not described, and/or without one or more of the operations discussed. Additionally, the order in which the operations of the process 700 as illustrated in FIG. 7 and described below is not intended to be limiting.

In an embodiment, as shown in FIG. 7, another exemplary process for determining the mean phase is provided. The process 700 may include the following operations:

In 7302, a set of initial cardiac images of interest may be determined based on the one or more cardiac images of the sampled cardiac motion phase(s), an average cardiac rate, and/or a cardiac rate fluctuation.

In some embodiments, the processing device 140 (e.g., the cardiac motion parameter determination module 17300) may perform operation 7302. In some embodiments, cardiac image(s) with a relatively high quality may be selected from the plurality of cardiac images of the plurality of sampled cardiac motion phases. In some embodiments, the cardiac image(s) with the relatively high quality may be determined as the set of initial cardiac images of interest. In some embodiments, the qualities of the cardiac images may relate to the cardiac motion phases, the average cardiac rate, and/or the cardiac rate fluctuation. In some embodiments, the cardiac rate fluctuation may be represented by a standard deviation of cardiac rates.

Specifically, in some embodiments, if the phase is in the vicinity of 45%, the heart may usually be in the systolic period; if the phase is in the vicinity of 75%, the heart may usually be in the diastolic period. Therefore, the two phases may be often used clinically as the phase(s) for cardiac image reconstruction. If the average cardiac rate is relatively stable, the quality of the cardiac image(s) of the phase in the vicinity of 75% may be relatively high. If the average cardiac rate is relatively rapid, the quality of the cardiac image(s) of the phase in the vicinity of 45% may be relatively high.

In some embodiments, if the mean cardiac rate is relatively stable, the cardiac rate fluctuation may be relatively low. In some embodiments, if the average cardiac rate is relatively rapid, the average cardiac rate may be relatively high. Merely by way of example, if the average cardiac rate is larger than 70, and/or the standard deviation of cardiac rates is larger than 1, cardiac image(s) of a sampled cardiac motion phase (e.g., 50%) may be determined as the set of initial cardiac images of interest; otherwise, cardiac image(s) of a sampled cardiac motion phase (e.g., 75%) may be determined as the set of initial cardiac images of interest. In some embodiments, the cardiac motion phase(s) corresponding to the set of initial cardiac images of interest may be regarded as initial optimal phase(s).

In 7304, one or more vascular images of interest may be extracted from the set of initial cardiac images of interest.

In some embodiments, the processing device 140 (e.g., the cardiac motion parameter determination module 17300) may perform operation 7304.

Specifically, in some embodiments, according to the set of initial cardiac images of interest, ventricular image(s) may be extracted from the set of initial cardiac images of interest, a threshold associated with gray level(s) of a contrast agent may be determined according to the ventricular image(s). The ventricular image(s) may be segmented based on the threshold associated with the gray level(s) of the contrast agent to obtain contrast agent image(s). Then, the vascular image(s) of interest may be extracted from the contrast agent image(s). In the field of medical imaging technology, in order to enhance the imaging effect of a target site of a patient, a contrast agent may be usually injected or administered to the target site. Accordingly, the set of initial cardiac images of interest may be image(s) generated after the injection or administration of the contrast agent.

In some embodiments, the vascular image(s) of interest may be extracted from the plurality of cardiac images of the plurality of sampled cardiac motion phases. Merely by way of example, ventricular image(s) may be extracted from the set of initial cardiac images of interest; a threshold associated with gray level(s) of a contrast agent may be determined according to the ventricular image(s); the ventricular image(s) may be segmented based on the threshold associated with the gray level(s) of the contrast agent to obtain contrast agent image(s); then, the ventricular image(s), contrast agent image(s), and/or the threshold may be applied to the plurality of cardiac images of the plurality of sampled cardiac motion phases to obtain vascular image(s) of interest. As another example, ventricular image(s) may be extracted from the plurality of cardiac images of the plurality of sampled cardiac motion phases; a threshold associated with gray level(s) of a contrast agent may be determined according to the ventricular image(s); the ventricular image(s) may be segmented based on the threshold associated with the gray level(s) of the contrast agent to obtain contrast agent image(s); then, vascular image(s) of interest may be extracted from the contrast agent image(s). More descriptions of the extraction of the vascular image(s) of interest may be found elsewhere in the present disclosure (e.g., FIGS. 8-10 and descriptions thereof).

In 7306, the cardiac motion parameter corresponding to the each sampled cardiac motion phase may be determined based on the one or more vascular images of interest.

In some embodiments, the processing device 140 (e.g., the cardiac motion parameter determination module 17300) may perform operation 7306.

Specifically, in some embodiments, the vascular center(s) in the vascular image(s) of interest may be determined; positions of the vascular centers of two adjacent sampled cardiac motion phases may be compared to obtain a displacement between the positions of the vascular centers of the two adjacent sampled cardiac motion phases in the plurality of sampled cardiac motion phases; and then a sampling interval (or a time interval) between the two adjacent sampled cardiac motion phases in the plurality of sampled cardiac motion phases may be obtained. The displacement between the vascular centers of the two adjacent sampled phases may be divided by the corresponding sampling interval to obtain a motion rate of the vascular center.

Similarly, motion rates of vascular center(s) for one or more sampled cardiac motion phases may be determined. In some embodiments, the motion rate(s) may be determined as the cardiac motion parameter(s) corresponding to the sampled cardiac motion phase(s). More descriptions of the determination of the cardiac motion parameter(s) may be found elsewhere in the present disclosure (e.g., FIG. 11 and descriptions thereof).

According to the process of determining the mean phase described above, initial optimal phase(s) may be determined according to the average cardiac rate and the cardiac rate fluctuation; region(s) of interest may be extracted from the set of initial cardiac images of interest; motion rate(s) of vascular center(s) between the sampled cardiac motion phase(s) may be determined according to the vascular image(s) of interest; and the mean phase may be determined according to the motion rate(s) of the vascular center(s) between the sampled cardiac motion phase(s). Therefore, the mean phase may be accurately determined, and the accuracy of the determination of the optimal phase in the cardiac motion may be ensured.

Figure 8:
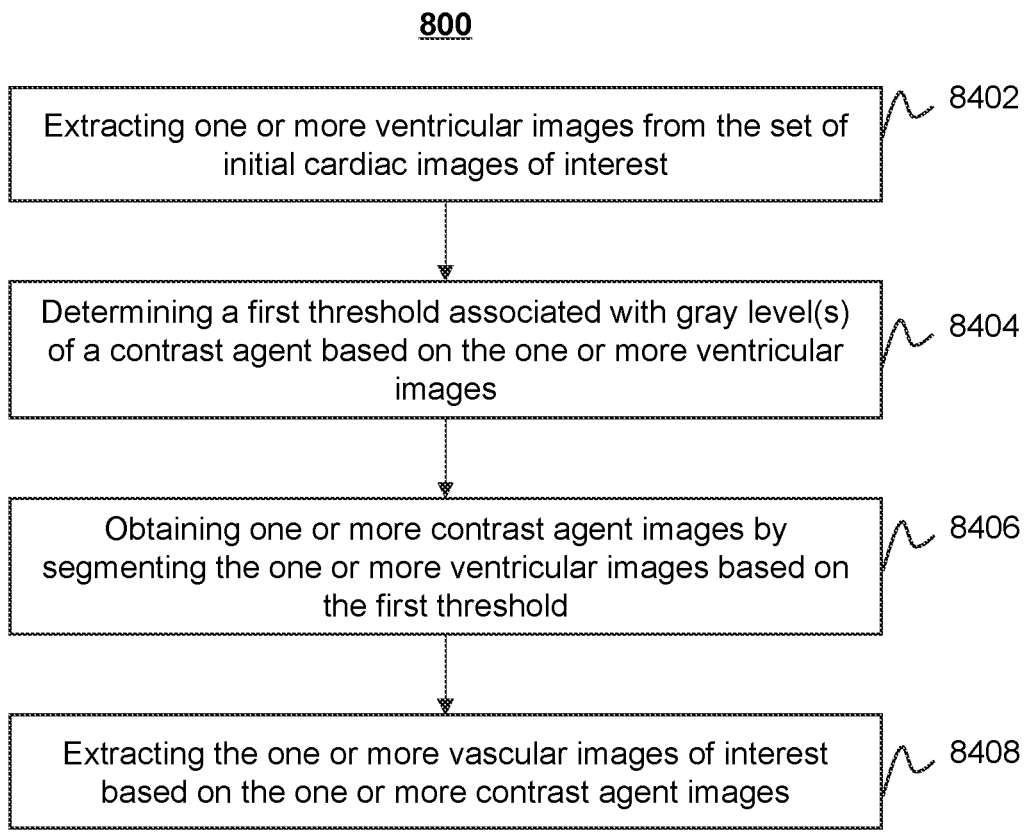
FIG. 8 is a flowchart illustrating an exemplary process for extracting vascular image(s) of interest according to some embodiments of the present disclosure.

FIG. 8 is a flowchart illustrating an exemplary process for extracting vascular image(s) of interest according to some embodiments of the present disclosure. In some embodiments, operation 7304 illustrated in FIG. 7 may be performed according to the process 800. In some embodiments, the process 800 may be executed by the imaging system 100. For example, the process 800 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 800 presented below are intended to be illustrative. In some embodiments, the process may be accomplished with one or more additional operations not described, and/or without one or more of the operations discussed. Additionally, the order in which the operations of the process 800 as illustrated in FIG. 8 and described below is not intended to be limiting.

In an embodiment, as shown in FIG. 8, an exemplary process for extracting vascular image(s) of interest is provided. The process 800 may include the following operations:

In 8402, one or more ventricular images may be extracted from the set of initial cardiac images of interest.

In some embodiments, the processing device 140 (e.g., the cardiac motion parameter determination module 17300) may perform operation 8402. In some embodiments, the ventricular image(s) may be extracted from the plurality of cardiac images of the plurality of sampled cardiac motion phases. The process of the extraction of the ventricular image(s) from the plurality of cardiac images of the plurality of sampled cardiac motion phases may be similar to the process illustrated below (e.g., the operations 8402-8408).

Specifically, in some embodiments, according to the average cardiac rate and the cardiac rate fluctuation, the set of initial cardiac images of interest may be selected from the cardiac image(s) of the sampled cardiac motion phase(s); according to a threshold associated with gray level(s) of bone(s), bone image(s) that have elements (e.g., pixels or voxels) with gray level(s) larger than the threshold may be extracted. A maximum intensity projection may be performed on the bone image(s) in an axial direction of a thoracic cavity, and a maximum intensity projection image of the bone image(s) may be obtained. The maximum intensity projection(s) may be generated based on element(s) having a maximum intensity (or density) along each projection ray directed to the patient's target site. That is, if the projection ray passes through the set of initial cardiac images of interest, the element(s) with the highest intensity (or density) in the image(s) may be retained and projected onto a two-dimensional plane, thereby forming a maximum intensity projection image of the bone image(s). According to the maximum intensity projection image of the bone image(s), the maximum intensity projection image (e.g., elements of the maximum intensity projection image) of the bone image(s) may correspond to different Boolean values. A thoracic contour boundary may be determined according to boundaries of the different Boolean values. Elements within the thoracic contour boundary may be extracted from the set of initial cardiac images of interest to obtain a pleural image (or thoracic contour image). Then, connected domain(s) may be determined based on a pleural image; a target connected domain with a maximum number of elements among the connected domain(s) may be extracted as a ventricular image. A connected domain may correspond to a region in a complex plane. If a simple closed curve is used in the complex plane, and the internal of the closed curve always belongs to the region, then the region is a connected domain.

In some embodiments, each element of an image may have a value (e.g., a gray level, a CT value, etc.). More descriptions of the extraction of the ventricular image(s) may be found elsewhere in the present disclosure (e.g., FIG. 9 and descriptions thereof).

In 8404, a first threshold associated with gray level(s) of a contrast agent may be determined based on the one or more ventricular images.

In some embodiments, the processing device 140 (e.g., the cardiac motion parameter determination module 17300) may perform operation 8404.

Specifically, in some embodiments, gradient image(s) corresponding to the ventricular image(s) may be determined based on the ventricular image(s). In image processing, modulus (or moduli) of gradient(s) may be simply referred as gradient(s), and an image using the gradient(s) as elements may be referred as a gradient image. If an image (e.g., a ventricular image) includes an edge (e.g., of different portions of an object), a corresponding gradient image may include relatively large gradient value(s). If the image includes a relatively smooth part, and difference(s) between gray level(s) are relatively low, then the corresponding gradient value(s) are relatively low. The gray level(s) of the element(s) in the gradient image may be analyzed statistically, and a target ventricular image whose corresponding gradient image has elements with values larger than a proportional threshold may be determined as a marker image. The threshold associated with the gray level(s) of the contrast agent may be determined based on the value(s) of the element(s) of the marker image using the OTSU algorithm. The OTSU algorithm is an efficient algorithm for the binarization of image(s), using a threshold to segment an original image into a foreground image and a background image. An optimal segment threshold may be taken as the threshold associated with the gray level(s) of the contrast agent.

In some embodiments, the proportional threshold may be a predetermined value which is an empirical value or an appropriate value determined by the system. More descriptions of the determination of the threshold associated with the gray level(s) of the contrast agent may be found elsewhere in the present disclosure (e.g., FIG. 10 and descriptions thereof).

In 8406, one or more contrast agent images may be obtained by segmenting the one or more ventricular images based on the first threshold.

In some embodiments, the processing device 140 (e.g., the cardiac motion parameter determination module 17300) may perform operation 8406.

Specifically, in some embodiments, the image segmentation may be performed based on the threshold associated with the contrast agent (e.g., the first threshold). Element(s) with gray level(s) greater than the threshold associated with the contrast agent may be extracted from the ventricular image(s) to obtain the contrast agent image(s).

In 8408, the one or more vascular images of interest may be extracted based on the one or more contrast agent images.

In some embodiments, the processing device 140 (e.g., the cardiac motion parameter determination module 17300) may perform operation 8408.

Specifically, in some embodiments, the right coronary artery is an arterial blood vessel that is clinically more visible than other blood vessels, the motion of the right coronary artery may reflect the motion of the heart, and then the motion of the heart in different phases may be determined by detecting the motion of the right coronary artery in the corresponding phases. In some embodiments, in the contrast agent image(s), image(s) having a relatively low amount of elements associated with the contrast agent and having elements with relatively low extravascular CT values may be extracted from portion(s) of the contrast agent image(s) corresponding to the upper left half of the ventricle to obtain the vascular image(s) of interest.

According to the process for extracting the vascular image(s) of interest described above, ventricular image(s) may be extracted from the set of initial cardiac images of interest; the threshold associated with gray level(s) of the contrast agent may be determined according to the ventricular image(s); the ventricular image(s) may be segmented based on the threshold associated with the contrast agent to obtain the contrast agent image(s); and the vascular image(s) of interest may be extracted from the contrast agent image(s). Therefore, right coronary vascular image(s) may be determined accurately in the set of initial cardiac images of interest, thereby improving the accuracy of the determination of the motion rate(s) of the vascular center(s), and improving the accuracy of the determination of the optimal phase in the cardiac motion.

It should be noted that, in some embodiments, the vascular image(s) of interest may be extracted from the plurality of cardiac images of the plurality of sampled cardiac motion phases. For example, the ventricular image(s) extracted in 8402, the first threshold determined in 8404, and/or the contrast agent image(s) obtained in 8406 may be applied to the plurality of cardiac images of the plurality of sampled cardiac motion phases to obtain the vascular image(s) of interest.

Figure 9:
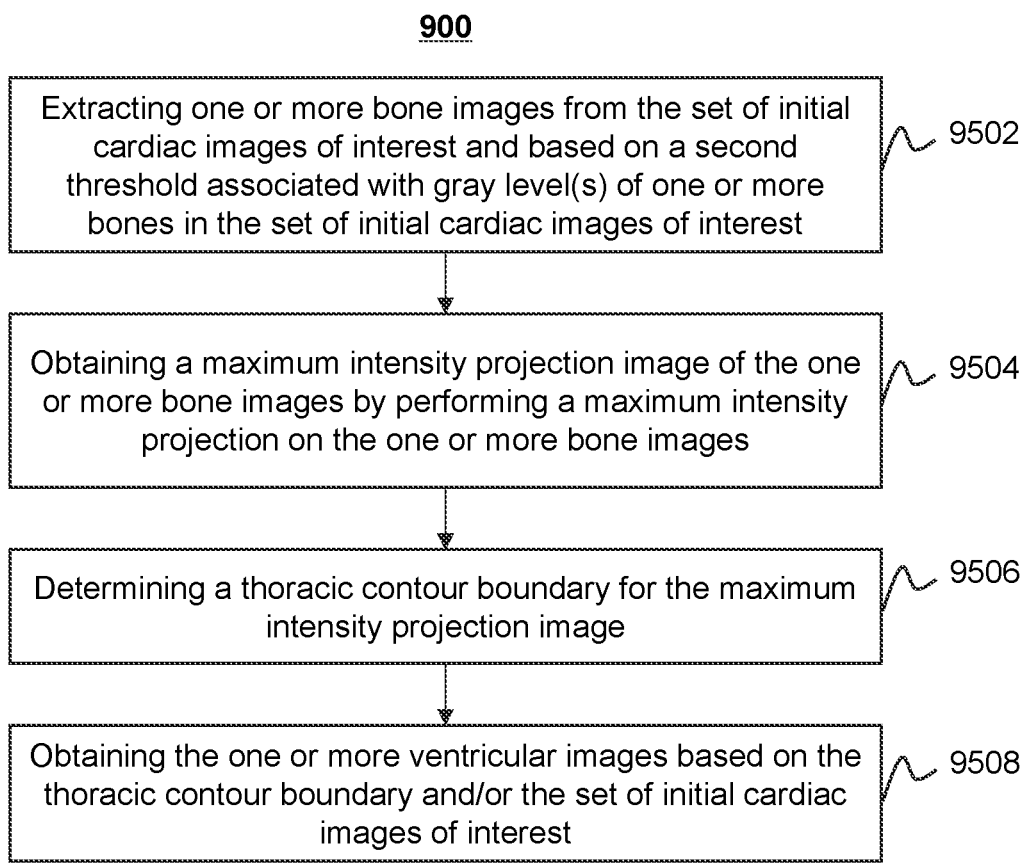
FIG. 9 is a flowchart illustrating an exemplary process for obtaining ventricular image(s) according to some embodiments of the present disclosure.

FIG. 9 is a flowchart illustrating an exemplary process for obtaining ventricular image(s) according to some embodiments of the present disclosure. In some embodiments, operation 8402 illustrated in FIG. 8 may be performed according to the process 900. In some embodiments, the process 900 may be executed by the imaging system 100. For example, the process 900 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 900 presented below are intended to be illustrative. In some embodiments, the process may be accomplished with one or more additional operations not described, and/or without one or more of the operations discussed. Additionally, the order in which the operations of the process 900 as illustrated in FIG. 9 and described below is not intended to be limiting.

In an embodiment, as shown in FIG. 9, an exemplary process for extracting ventricular image(s) is provided. The process 900 may include the following operations:

In 9502, one or more bone images may be extracted from the set of initial cardiac images of interest and based on a second threshold associated with gray level(s) of one or more bones in the set of initial cardiac images of interest.

In some embodiments, the processing device 140 (e.g., the cardiac motion parameter determination module 17300) may perform operation 9502. In some embodiments, the bone image(s) may be extracted from the plurality of cardiac images of the plurality of sampled cardiac motion phases similarly.

Specifically, in some embodiments, according to the average cardiac rate and the cardiac rate fluctuation, the set of initial cardiac images of interest may be selected from the cardiac image(s) of the sampled cardiac motion phase(s); according to the threshold associated with the bone(s) (e.g., the second threshold), bone image(s) that have elements with gray level(s) larger than the threshold associated with the bone(s) may be extracted. The threshold associated with the bone(s) in the thoracic cavity may be generally 1500 HU according to the clinical experience. That is, region(s) including elements with gray level(s) greater than 1500 HU may be extracted from the set of initial cardiac images of interest and may be regarded as the bone image(s).

In an embodiment, the bone image(s) may be determined according to the following equations:

$$BoneImg = \begin{cases} OriImg, & \text{if } OriImg > BoneThre \\ 0 & \text{else} \end{cases}, \quad \text{Equation (6)}$$

$$BoneImgSet = BoneImg_i \; i = 1,2, \ldots, ImgNum, \quad \text{Equation (7)}$$

where BoneImg is a bone image, BoneThre is the threshold associated with bone(s), OriImg represents the set of initial cardiac images of interest, and BoneImgSet is a set of bone images.

In Equation (7), ImgNum is the number of the bone images.

In 9504, a maximum intensity projection image of the one or more bone images may be obtained by performing a maximum intensity projection on the one or more bone images.

In some embodiments, the processing device 140 (e.g., the cardiac motion parameter determination module 17300) may perform operation 9504.

Specifically, in some embodiments, the maximum intensity projection image may be generated based on element(s) having a maximum intensity (or density) along each projection ray directed to the target site of the patient. That is, if the projection ray passes through the set of initial cardiac images of interest, the element(s) with the highest intensity (or density) in the image(s) may be retained and projected onto a two-dimensional plane, thereby forming a maximum intensity projection image of the bone image(s).

In an embodiment, the maximum intensity projection image of the bone image(s) may be determined according to the following equations:

$$BoneMIP_{axial} = MIP(BoneImgSet), \quad \text{Equation (8)}$$

where BoneImgSet is a set of bone image(s), MIP is a maximum intensity projection operation, and $BoneMIP_{axial}$ is a maximum intensity projection image of the set of bone images.

In Equation (8), axial refers that the maximum intensity projection is performed on the bone image(s) in an axial direction of a thoracic cavity.

In 9506, a thoracic contour boundary may be determined for the maximum intensity projection (MIP) image.

In some embodiments, the processing device 140 (e.g., the cardiac motion parameter determination module 17300) may perform operation 9506.

Specifically, in some embodiments, according to the maximum intensity projection image of the bone image(s), the Boolean value of elements in a ventricular region of the maximum intensity projection image of the bone image(s) may be set as 1, and the Boolean value of elements in the non-ventricular region of the maximum intensity projection image of the bone image(s) may be set as 0. A boundary of elements with Boolean value 1 and elements with Boolean value 0 may be taken as a thoracic contour boundary.

In some embodiments, a thoracic contour boundary may correspond to a binary image, wherein elements inside the thoracic contour boundary may have the Boolean value 1, while elements outside the thoracic contour boundary may have the Boolean value 0. In some embodiments, the thoracic contour boundary may include one or more elements representing one or more positions of a thoracic contour boundary of an object. More descriptions of the position(s) of the thoracic contour boundary may be found elsewhere in the present disclosure (e.g., FIGS. 18 and 20 and descriptions thereof).

In an embodiment, the thoracic contour boundary may be determined as:

$$\text{Boundary} = \text{CalBoundary}(\text{BoneMIP}_{axial}), \quad \text{Equation (9)}$$

where Boundary represents elements with Boolean values, $BoneMIP_{axial}$ is the maximum intensity projection image of the bone image(s), and CalBoundary is an operation that sets the Boolean value as 1 or 0 according to whether it is a ventricular region.

In 9508, the one or more ventricular images may be obtained based on the thoracic contour boundary and/or the set of initial cardiac images of interest.

In some embodiments, the processing device 140 (e.g., the cardiac motion parameter determination module 17300) may perform operation 9508.

Specifically, in some embodiments, a pleural image may be obtained according to the set of initial cardiac images of interest and the thoracic contour boundary. Connected domain(s) may be determined according to the pleural image, and a target connected domain with a maximum number of elements among the connected domain(s) may be identified as a ventricular mask image.

According to the set of initial cardiac images of interest and the thoracic contour boundary, a pleural image may be obtained. A region within a thoracic contour boundary may be extracted as a pleural image in one of the set of initial cardiac images of interest. That is, a region that has specific elements may be extracted as a pleural image in the set of initial cardiac images of interest. The specific elements may have value(s) larger than a threshold associated with soft tissue(s) and may have a Boolean value 1.

In some embodiments, a pleural image may be a binary image associated with the thoracic contour boundary. In some embodiments, the specific elements may have value(s) larger than the threshold associated with soft tissue(s) and may correspond to elements having a Boolean value 1 in the thoracic contour boundary. In some embodiments, the threshold associated with soft tissue(s) may be a default value determined by the imaging system 100 or preset by a user or operator via the terminal(s) 130.

In an embodiment, the pleural image may be extracted according to the following equation:

$$MaskImg = \begin{cases} 1 & OriImg > SoftTisThre \text{ and Boundary} = 1 \\ 0 & \text{else} \end{cases}, \quad \text{Equation (10)}$$

where MaskImg is a pleural image, Boundary represents elements with Boolean values, and SoftTisThre is a threshold associated with soft tissue(s).

Connected domain(s) may be determined according to the pleural image, and a target connected domain with a maximum number of elements among the connected domain(s) may be designated as a ventricular mask image. Based on the pleural image, the target connected domain with the maximum number of elements may be designated as the ventricular mask image. A connected domain may correspond to a region in a complex plane. If a simple closed curve is used in the complex plane, and the internal of the closed curve always belongs to the region, then the region is a connected domain.

In some embodiments, the ventricular mask image may be a binary image associated with the ventricular region of the object. In some embodiments, the ventricular image(s) may be obtained based on the ventricular mask image and the set of initial cardiac images of interest. In some embodiments, the ventricular image(s) may be obtained directly from the set of initial cardiac images of interest.

According to the process for extracting the ventricular image(s), image segmentation may be performed on the initial cardiac image(s) of interest based on a threshold associated with bone(s) to obtain bone image(s); a maximum intensity projection may be performed on the bone image(s) to obtain a maximum intensity projection image. The process may further include determining a thoracic contour boundary according to the maximum intensity projection image, extracting a region within the thoracic contour boundary as a pleural image, determining connected domain(s) of the pleural image, and designating a target connected domain with the maximum number of elements as the ventricular mask image. Therefore, the thoracic contour boundary may be accurately determined, thereby improving the accuracy of the determination of the ventricular image(s), and improving the accuracy of the determination of the heart region.

Figure 10:
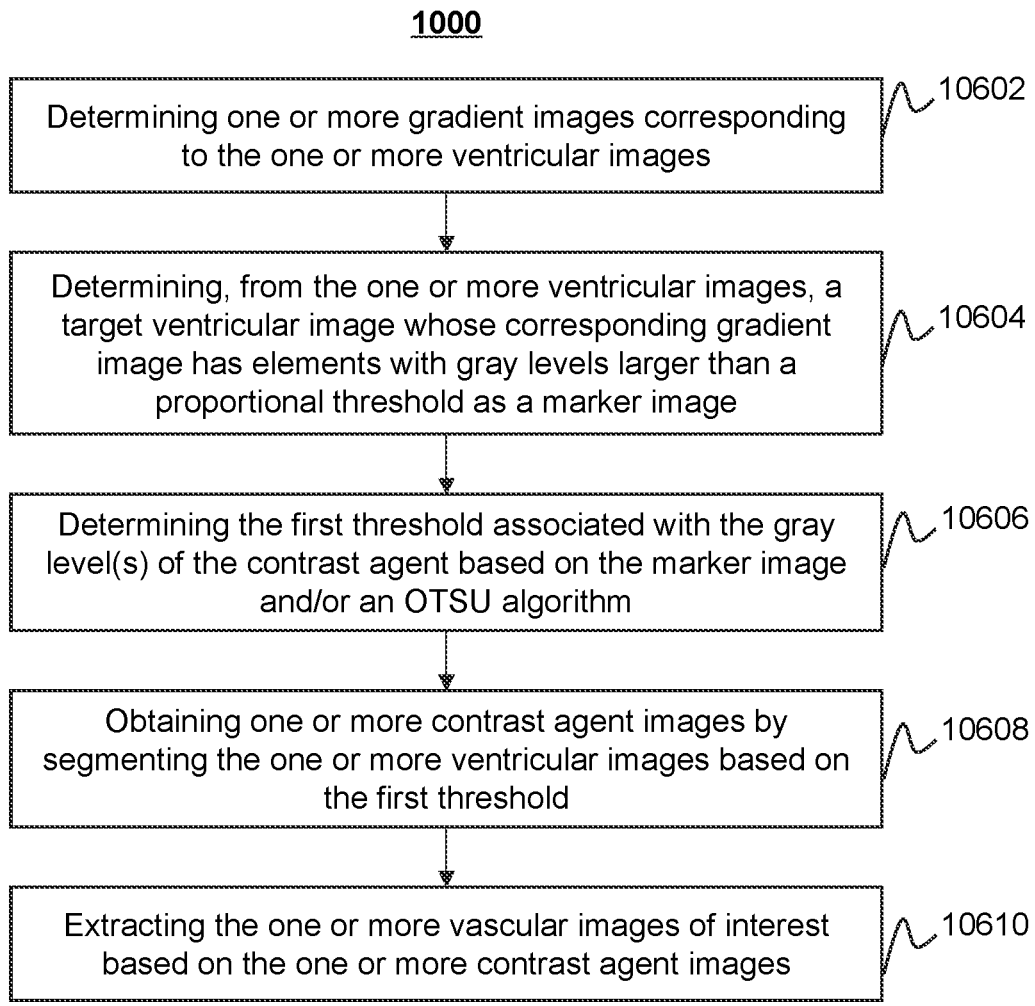
FIG. 10 is a flowchart illustrating an exemplary process for extracting vascular image(s) of interest according to some embodiments of the present disclosure.

FIG. 10 is a flowchart illustrating an exemplary process for extracting vascular image(s) of interest according to some embodiments of the present disclosure. In some embodiments, operation 8404 illustrated in FIG. 8 may be performed according to the operations 10602-10606 in process 1000. In some embodiments, the process 1000 may be executed by the imaging system 100. For example, the process 1000 may be implemented as a set of instructions (e.g., an application) stored in one or more storage devices (e.g., the storage device 150, the storage 220, and/or the storage 390) and invoked and/or executed by the processing device 140 (implemented on, for example, the processor 210 of the computing device 200, and the CPU 340 of the mobile device 300). The operations of the process 1000 presented below are intended to be illustrative. In some embodiments, the process may be accomplished with one or more additional operations not described, and/or without one or more of the operations discussed. Additionally, the order in which the operations of the process 1000 as illustrated in FIG. 10 and described below is not intended to be limiting.

In an embodiment, as shown in FIG. 10, an exemplary process for determining a threshold associated with gray level(s) of a contrast agent is provided. The process 1000 may include the following operations:

In 10602, one or more gradient images corresponding to the one or more ventricular images may be determined.

In some embodiments, the processing device 140 (e.g., the cardiac motion parameter determination module 17300) may perform operation 10602.

Specifically, in some embodiments, gradient image(s) of the ventricular image(s) may be determined based on the ventricular image(s). In image processing, modulus (or moduli) of gradient(s) may be simply referred as gradient(s), and an image using the gradient(s) as elements may be referred as a gradient image. If an image (e.g., a ventricular image) includes an edge (e.g., of different portions of an object), a corresponding gradient image may include relatively large gradient value(s). If the image includes a relatively smooth part, and difference(s) between gray level(s) are relatively low, then the corresponding gradient value(s) are relatively low. In some embodiments, the determination of the gradient image(s) may be performed using the Sobel operator. The Sobel operator is a discrete first-order difference operator used to determine an approximation of a first-order gradient of an image brightness function. A gradient vector corresponding to an element of an image may be generated by applying the Sobel operator to the element in the image.

In an embodiment, the gradient image(s) may be determined as:

$$HeartImg = \begin{cases} OriImg & \text{if } MaskImg = 1 \\ 0 & \text{esle} \end{cases}, \quad \text{Equation (11)}$$

$$GradImg = \frac{\partial HeartImg}{\partial(x, y)}, \quad \text{Equation (12)}$$

where GradImg refers to the gray levels of elements of a gradient image, HeartImg is a ventricular image, and (x, y) is a gray level of an element with an abscissa value x and an ordinate value y.

In Equations (11) and (12), MaskImg refers to the pleural image, OriImg refers to the set of initial cardiac images of interest.

In 10604, a target ventricular image whose corresponding gradient image has elements with gray levels larger than a proportional threshold may be determined from the one or more ventricular images as a marker image.

In some embodiments, the processing device 140 (e.g., the cardiac motion parameter determination module 17300) may perform operation 10604.

Specifically, in some embodiments, the gray level(s) of the element(s) in the gradient image may be analyzed statistically, and a target ventricular image whose corresponding gradient image has elements with values larger than a proportional threshold may be determined as a marker image. In some embodiments, the gray level(s) of the element(s) in the gradient image may be analyzed statistically to obtain a histogram of the element(s); an appropriate proportion of gray level(s) may be selected as a proportional threshold; and the element(s) with gray level(s) greater than the proportional threshold may be extracted to obtain a marker image.

In an embodiment, the marker image may be determined as:

$$MarkerImg = \begin{cases} HeartImg & GradImg > Q \\ 0 & GradImg \le Q \end{cases}, \quad \text{Equation (13)}$$

where MarkerImg is a marker image, GradImg refers to gray levels of a gradient image, and HeartImg is a ventricular image.

In Equation (13), Q is the proportional threshold. In some embodiments, Q may be in a range from 0 to 1.

In 10606, the first threshold associated with the gray level(s) of the contrast agent may be determined based on the marker image and/or an OTSU algorithm.

In some embodiments, the processing device 140 (e.g., the cardiac motion parameter determination module 17300) may perform operation 10606. In some embodiments, the first threshold may refer to a threshold associated with the contrast agent.

Specifically, in some embodiments, the threshold associated with the contrast agent may be determined based on the value(s) of the element(s) of the marker image using the OTSU algorithm. The OTSU algorithm is an efficient algorithm for the binarization of image(s), using a threshold to segment an original image into a foreground image and a background image. An optimal segment threshold may be taken as the threshold associated with the gray level(s) of the contrast agent.

In an embodiment, the threshold associated with the contrast agent may be determined as:

ContrastThre=Otsuthresh(MarkerImg), Equation (14)

where ContrastThre is threshold associated with the contrast agent, MarkerImg is a marker image, and Otsuthresh refers to the OTSU algorithm.

According to the process for determining the threshold associated with the contrast agent, the gradient image(s) of the ventricular image(s) may be determined; a target ventricular image whose corresponding gradient image has elements with gray levels larger than the proportional threshold may be determined as a marker image; and the threshold associated with the contrast agent may be determined based on the values of the elements of the marker image using the OTSU algorithm. Therefore, threshold(s) associated with contrast agent(s) at different concentrations may be determined, thereby improving the accuracy of the determination of the contrast agent image(s) by segmenting the ventricular image(s) based on the determined threshold associated with the contrast agent.

In an embodiment, a process for obtaining vascular image(s) of interest based on ventricular image(s) and the threshold associated with the contrast agent is provided. The process may include the following operations:

In 10608, one or more contrast agent images may be obtained by segmenting the one or more ventricular images based on the first threshold.

In some embodiments, the processing device 140 (e.g., the cardiac motion parameter determination module 17300) may perform operation 10608.

In an embodiment, the obtaining of the contrast agent image(s) by segmenting the ventricular image(s) based on the threshold associated with the contrast agent may be represented as:

$$ContrastImg = \begin{cases} OriImg & HeartImg > ContrstThre \\ 0 & HeartImg \leq ContrstThre \end{cases}, \quad \text{Equation (15)}$$

where ContrastImg refers to the contrast agent image(s), HeartImg refers to ventricular image(s), and ContrstThre refers to the threshold associated with the contrast agent.

In Equation (15), OriImg refers to the set of initial cardiac images of interest.

In 10610, one or more vascular images of interest may be extracted based on the one or more contrast agent images.

In some embodiments, the processing device 140 (e.g., the cardiac motion parameter determination module 17300) may perform operation 10610.

In an embodiment, an image of the right coronary artery of the heart may be extracted as a vascular image of interest. The right coronary artery is an arterial blood vessel that is clinically more visible than other blood vessels, the motion of the right coronary artery may reflect the motion of the heart, and then the motion of the heart in different phases may be determined by detecting the motion of the right coronary artery in the corresponding phases. The right coronary artery may generally have the following characteristics: the position of the right coronary artery may be located in the upper left part of the ventricle; the number (or count) of elements associated with the contrast agent may be relatively low; the CT value(s) of extravascular element(s) may be relatively low. Connected domain(s) associated with the contrast agent that have the characteristics mentioned above may be extracted as vascular image(s) of interest.

Figure 11:
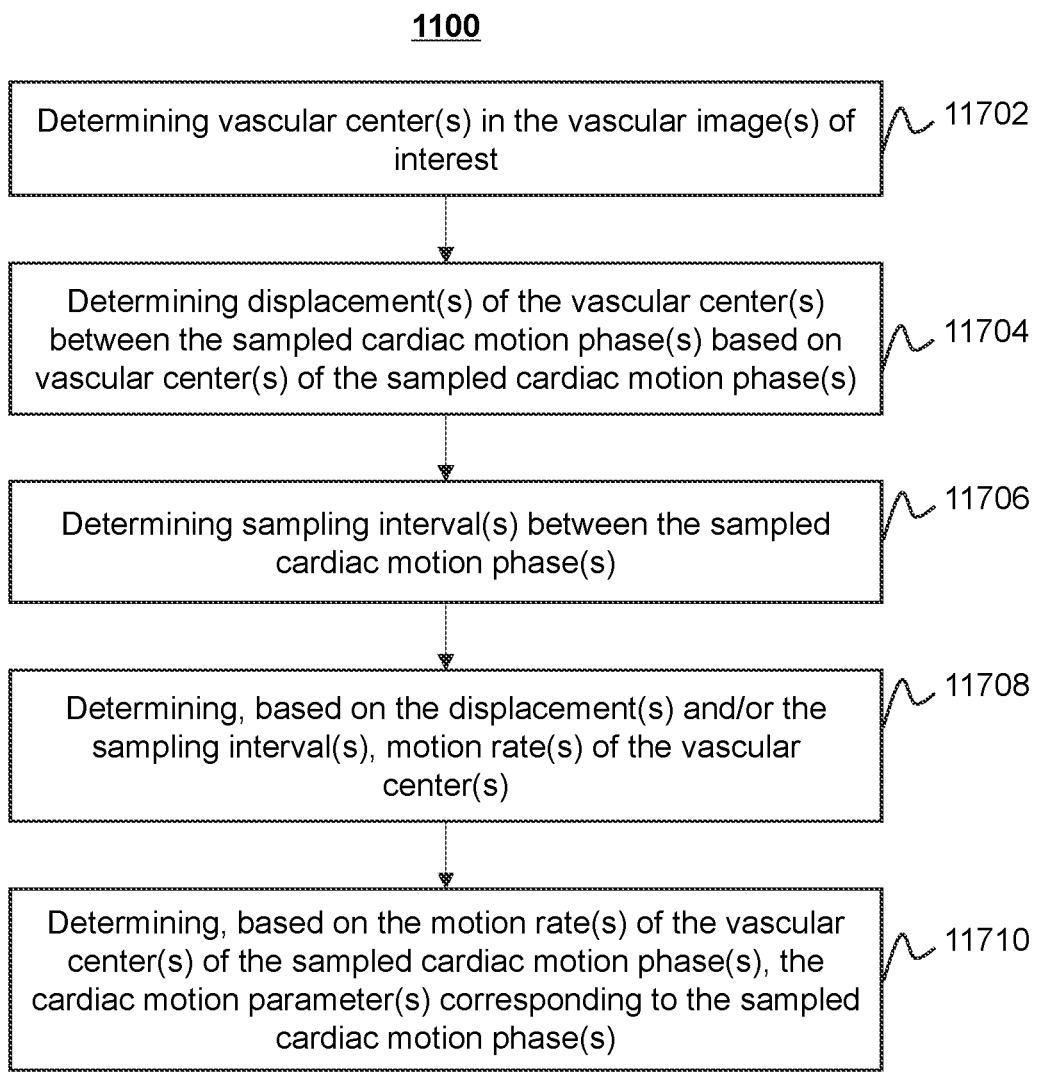
FIG. 11 is a flowchart illustrating an exemplary process for determining cardiac motion parameter(s) according to some embodiments of the present disclosure.

FIG. 11 is a flowchart illustrating an exemplary process for determining cardiac motion parameter(s) according to some embodiments of the present disclosure. In some embodiments, operation 7306 illustrated in FIG. 7 may be performed according to the process 1100.

In an embodiment, as shown in FIG. 11, an exemplary process for determining motion rate(s) of vascular center(s) is provided. The process 1100 may include the following operations:

In 11702, vascular centers may be determined in the vascular image(s) of interest.

In some embodiments, the processing device 140 (e.g., the cardiac motion parameter determination module 17300) may perform operation 11702. In some embodiments, a first vascular center may be determined in each vascular image of interest of each sampled cardiac motion phase.

Specifically, in some embodiments, vascular center(s) may be selected in the vascular image(s) of interest.

In some embodiments, a vascular center may be determined in each vascular image of interest of each sampled cardiac motion phase.

In an embodiment, the vascular center(s) may be determined as:

$$(x_{p^n}, y_{p^n}) = \text{Center}(\text{VessalImg}_{p^n}), \quad \text{Equation (16)}$$

where VessalImg refers to a vascular image of interest, $x_{p^n}$ refers to an abscissa value of a vascular center, $y_{p^n}$ refers to an ordinate value of the vascular center, p refers to a sampled cardiac motion phase, and n refers to the sequence number of the sampled cardiac motion phase. In some embodiments, n may be 1, 2, . . . , or 10. Correspondingly, in some embodiments, p may be 10%, 20%, . . . , or 100%.

In 11704, the displacement(s) of the vascular center(s) between multiple sampled cardiac motion phases may be determined based on vascular center(s) of the sampled cardiac motion phase(s).

In some embodiments, the processing device 140 (e.g., the cardiac motion parameter determination module 17300) may perform operation 11704. In some embodiments, a displacement of the first vascular center may be determined based on a first position of the first vascular center in the each vascular image of interest and/or a second position of a second vascular center in a vascular image of interest of another sampled cardiac motion phase adjacent to the each sampled cardiac motion phase.

Specifically, in some embodiments, the displacement(s) of the vascular center(s) between multiple sampled cardiac motion phases may be determined based on vascular center(s) of adjacent sampled cardiac motion phases.

In an embodiment, the displacement(s) of the vascular center(s) may be determined as:

$$\text{Displacement}_{p^n} = \sqrt{(x_{p^n} - x_{p^{n-1}})^2 + (y_{p^n} - y_{p^{n-1}})^2}, \quad \text{Equation (17)}$$

where Displacement refers to a displacement of a vascular center, $x_{p^n}$ refers to an abscissa value of a vascular center, $y_{p^n}$ refers to an ordinate value of the vascular center, p refers to a sampled cardiac motion phase, and n refers to the sequence number of the sampled cardiac motion phase. In some embodiments, n may be 1, 2, . . . , or 10. Correspondingly, in some embodiments, p may be 10%, 20%, . . . , or 100%.

In 11706, sampling interval(s) between the multiple sampled cardiac motion phases.

In some embodiments, the processing device 140 (e.g., the cardiac motion parameter determination module 17300) may perform operation 11706. In some embodiments, a sampling interval between the each sampled cardiac motion phase and the another sampled cardiac motion phase adjacent to the each sampled cardiac motion phase may be determined.

Specifically, in some embodiments, the beat frequency of the heart may be variable. An equal sampling interval may refer that sampling intervals in each cardiac cycle are equal. The sampling interval(s) between different sampled cardiac motion phases may be different. Therefore, it is desirable to determine the sampling interval(s) based on instantaneous time points in each cardiac cycle and a reference cardiac cycle time.

In an embodiment, the sampling interval(s) may be determined as:

$$RR_{frac} = \text{delay}(RR_{inst}, p^n) - \text{delay}(RR_{inst}, p^{n-1}), \quad \text{Equation (18)}$$

$$\text{delay}(RR_{inst}, p^n) = RR_{inst} \times \frac{PD(p^n)}{100} + DO(P_p), \quad \text{Equation (19)}$$

$$PD = \text{round}(p^n \times C(p^n)), \quad \text{Equation (20)}$$

$$DO = \text{round}[RR_{ref} \times (p^n/100) \times (1 - C(p^n))], \quad \text{Equation (21)}$$

$$C(p^n) = 1 - (1 - p^n/100)^2, \quad \text{Equation (22)}$$

where $RR_{frac}$ refers to a sampling interval, $RR_{inst}$ refers to an instantaneous time in a cardiac cycle, $RR_{ref}$ refers to a reference cardiac cycle time, and p refers to a sampled cardiac motion phase.

In Equations (18)-(22), n refers to the sequence number of the sampled cardiac motion phase, delay refers to a time delay of a phase p relative to the instantaneous time in a cardiac cycle (in ms), PD refers to the percentage of the R-R interval, DO refers to a fixed delay offset (in ms) from the percentage location within the R-R interval, round refers to the round function, C refers to the compliance curve function.

In 11708, quotient(s) of the displacement(s) of the vascular center(s) between the sampled cardiac motion phase(s) divided by corresponding sampling interval(s) may be determined, and the quotient(s) may be determined as motion rate(s) of the vascular center(s).

In some embodiments, the processing device 140 (e.g., the cardiac motion parameter determination module 17300) may perform operation 11708. In some embodiments, a motion rate of a vascular center may be determined based on a displacement of the vascular center between two sampled cardiac motion phases and the corresponding sampling interval between the two sampled cardiac motion phases.

In an embodiment, the motion rate(s) of the vascular center(s) may be determined as:

$$\text{Velocity}_n = \text{Displacement}_n / RR_{frac}, \qquad \text{Equation (23)}$$

where Displacement refers to a displacement of a vascular center, $RR_{frac}$ refers to a corresponding sampling interval, Velocity refers to a motion rate of the vascular center, and n refers to the sequence number of the sampled cardiac motion phase(s).

In 11710, cardiac motion parameter(s) corresponding to the sampled cardiac motion phase(s) may be determined based on the motion rate(s) of the vascular center(s) of the sampled cardiac motion phase(s).

In some embodiments, the processing device 140 (e.g., the cardiac motion parameter determination module 17300) may perform operation 11710. In some embodiments, a motion rate of the first vascular center may be determined based on the displacement and the corresponding sampling interval. In some embodiments, the motion rate of the first vascular center may be designated as a cardiac motion parameter.

Specifically, in some embodiments, a mean phase may be selected from the plurality of (sampled) cardiac motion phases according to the cardiac motion parameter(s) of the plurality of (sampled) cardiac motion phases. Alternatively or additionally, other cardiac motion parameter(s) of other phase(s) excluding the plurality of (sampled) cardiac motion phases may be obtained by performing an interpolation operation on the cardiac motion parameter(s) of the plurality of (sampled) cardiac motion phases, and a mean phase may be selected from the other phase(s).

According to the process for determining motion rate(s) of the vascular center(s), the vascular center(s) may be determined in the vascular image(s) of interest; displacement(s) of the vascular center(s) between the sampled cardiac motion phases may be determined according to the vascular center(s) of the sampled cardiac motion phases; sampling interval(s) between the sampled cardiac motion phases may be determined; and quotient(s) of the displacement(s) of the vascular center(s) between the sampled cardiac motion phases divided by corresponding sampling interval(s) may be determined to obtain the motion rate(s) of the vascular center(s). Therefore, the accuracy of the determination of motion parameter(s) of the vascular center(s) between adjacent sampled cardiac motion phase(s) may be improved, and accordingly, a sampled cardiac motion phase with a minimum motion amplitude or intensity may be selected accurately.

FIG. 12 is a flowchart illustrating an exemplary process for determining a mean phase based on motion rate(s) of vascular center(s) according to some embodiments of the present disclosure. In some embodiments, operation 5108 illustrated in FIG. 5 may be performed according to the process 1200.

In an embodiment, as shown in FIG. 12, an exemplary process for determining a mean phase based on the motion rate(s) of the vascular center(s) is provided. The process 1200 may include the following operations:

In 12802, weighting operation(s) may be performed on the motion rate(s) of the vascular center(s) of the sampled cardiac motion phase(s) and a ratio of the sampled cardiac motion phases to all the cardiac motion phases, to obtain weighted motion rate(s) between the sampled cardiac motion phase(s).

In some embodiments, the processing device 140 (e.g., the mean phase determination module 17400) may perform operation 12802.

Specifically, in some embodiments, if the weighted motion rate(s) are relatively large, the motion during the corresponding sampling interval(s) may be relatively stable.

In an embodiment, the weighted motion rate(s) may be determined as:

$$\text{Velocity}_n^w = \text{weight}_n * \left( \frac{\max(\text{Velocity}_n) - \text{Velocity}_n}{\max(\text{Velocity}_n) - \min(\text{Velocity}_n)} \right), \qquad \text{Equation (24)}$$

where $\text{Velocity}_n^w$ refers to a weighted motion rate, weight refers to the ratio of the sampled cardiac motion phases to all the cardiac motion phases, and Velocity refers to a motion rate of a vascular center.

In Equation (24), n refers to the sequence number of the sampled cardiac motion phase.

In 12804, the cardiac motion parameters of all the cardiac motion phases may be obtained by performing an interpolation on the weighted motion rate(s).

In some embodiments, the processing device 140 (e.g., the mean phase determination module 17400) may perform operation 12804.

Specifically, in some embodiments, the "interpolation operation" may use known function values of one or more points in a certain section to determine an appropriate specific function. Function values of other points between the certain section may be used as an approximation of the specific function. This operation may be regarded as interpolation.

In an embodiment, the cardiac motion parameter(s) may be determined as:

$$V = \text{interp1}(\text{Velocity}_n^w, x, xi, \text{'spline'}), \qquad \text{Equation (25)}$$

$$x = (p^n - p^{n-1})/2, xi = [x(1): 1: x(\text{end})], \qquad \text{Equation (26)}$$

where V refers to the motion parameter(s) after interpolation, interp1 refers to a one-dimensional interpolation operation, n refers to the sequence number of the sampled cardiac motion phase(s), w refers to weight(s), x refers to sampled cardiac motion phase(s), xi refers to sampled cardiac motion phase(s) after interpolation, and 'spline' refers that the interpolation operation is a spline interpolation.

In Equations (25)-(26), $p^n$ refers to the nth sampled cardiac motion phase, x(1) refers to the first sampled cardiac motion phase before interpolation, and x(end) refers to the last sampled cardiac motion phase before interpolation. In some embodiments, x(1) may be $(p^2-p^1)/2$, and x(end) may be $(p^{LN}-p^{LN-1})/2$, wherein LN refers to the last sampled cardiac motion phase before interpolation.

In 12806, a cardiac motion phase corresponding to a maximum motion parameter may be designated as the mean phase.

In some embodiments, the processing device 140 (e.g., the mean phase determination module 17400) may perform operation 12806. In some embodiments, the motion parameter herein may be regarded as a second motion parameter, which may be different from the first motion parameter described in FIG. 6. For example, if the second motion parameter is relatively large, or the first cardiac motion parameter is relatively small, the cardiac motion may be relatively smooth.

Specifically, in some embodiments, according to the determined cardiac motion parameters of all the cardiac motion phases, a cardiac motion phase with a maximum motion parameter may be selected from the cardiac motion parameters of all the cardiac motion phases as the mean phase.

According to the process for determining the mean phase, weighted motion rate(s) between the sampled cardiac motion phase(s) may be obtained; cardiac motion parameters of all the cardiac motion phases may be obtained by performing an interpolation (e.g., a second-order derivable spline interpolation) on the weighted motion rate(s); and a cardiac motion phase with a maximum motion parameter may be selected as the mean phase. Therefore, a phase corresponding to a mild cardiac motion may be selected, according to the motion of the heart, as the mean phase.

In some embodiments, if the phase corresponding to the maximum cardiac motion parameter is selected as the mean phase, the cardiac motion corresponding to the mean phase may be relatively smooth (or mild), which can reduce the artifact(s) in the reconstructed cardiac image(s) and accordingly improve the quality of the reconstructed cardiac image(s).

FIG. 13 is a flowchart illustrating an exemplary process for obtaining a set of target cardiac images according to some embodiments of the present disclosure. In some embodiments, operation 5114 illustrated in FIG. 5 may be performed according to operations 13904 and 13906 of the process 1300.

In an embodiment, as shown in FIG. 13, an exemplary process for obtaining a set of cardiac images corresponding to optimal phase(s) is provided. The process 1300 may include the following operations:

In 13902, one or more cardiac motion phases in a preset range including the mean phase may be selected in each cardiac cycle of a plurality of cardiac cycles; and one or more cardiac images of the one or more cardiac motion phases may be reconstructed.

In some embodiments, the processing device 140 (e.g., the second reconstruction module 17500) may perform operation 13902. In some embodiments, the cardiac image(s) of the cardiac motion phase(s) may be reconstructed based on one or more sub-sets of projection data corresponding to the one or more cardiac motion phases in the each cardiac cycle.

Specifically, in some embodiments, heart motions of different patients may be different (or heart motion of a same patient in different cardiac cycles may be different), and the mean phase of a patient for different cardiac cycles within a period of time may be inconsistent. Therefore, it may be desirable to further obtain a phase of interest in each cardiac cycle for the patient based on the mean phase. On the basis of the mean phase, projection data of cardiac motion phase(s) within a preset range including the mean phase in each cardiac cycle may be selected, and corresponding cardiac image(s) may be reconstructed according to the projection data. In some embodiments, the preset range may be 2%, 5%, 10%, or the like. That is, phases in a range of 10% around the mean phase may be selected in each cardiac cycle, and cardiac image(s) corresponding to the selected phases may be reconstructed.

In 13904, a phase of interest may be determined in the each cardiac cycle based on one or more cardiac images of the each cardiac cycle.

In some embodiments, the processing device 140 (e.g., the second reconstruction module 17500) may perform operation 13904. In some embodiments, the optimal phase in the each cardiac cycle may refer to the phase of interest in the each cardiac cycle. In some embodiments, the cardiac image(s) corresponding to the optimal phase(s) may be referred to as the set of target cardiac images. In some embodiments, a target cardiac image may be referred to as a cardiac image of interest.

Specifically, in some embodiments, image(s) of a region of interest may be determined according to the cardiac image(s) corresponding to the phase within the preset range. A top-hat transformation may be performed on the image(s) of the region of interest to obtain a transformed image of the region of interest. A maximum gray level of the transformed image of the region of interest may be selected. The maximum gray level multiplied by one or more preset values may be designated as segment threshold(s). Elements that have gray levels greater than a segment threshold may be extracted from the transformed image of interest as a segmentation image corresponding to the segment threshold. Thus one or more segmentation images associated with each image of the region of interest may be obtained based on the one or more segment thresholds. A perimeter and an area of a blood vessel in each segmentation image of the segmentation images may be further determined. A compactness degree of the each segmentation image may be determined according to the perimeter and the area of a target object (e.g., the blood vessel) in the each segmentation image. A regularity degree of an image of the region of interest may be determined based on the compactness degree(s) of the segmentation image(s) associated with the image of the region of interest. A cardiac motion phase corresponding to an image of the region of interest that has a maximum regularity degree may be designated as the optimal phase of the each cardiac cycle.

In 13906, a set of target cardiac images may be obtained by determining a target cardiac image of the phase of interest in the each cardiac cycle.

In some embodiments, the processing device 140 (e.g., the second reconstruction module 17500) may perform operation 13906.

Specifically, in some embodiments, the obtaining of the set of target cardiac images may include: reconstructing based on projection data of a phase of interest in the each cardiac cycle to obtain the set of target cardiac images; or selecting a target cardiac image of the each cardiac cycle from a plurality of reconstructed cardiac images based on the phase of interest in the each cardiac cycle to obtain the set of target cardiac images.

According to the process for obtaining a set of target cardiac images, cardiac motion phases in a preset range including the mean phase in each cardiac cycle may be selected; a phase of interest may be determined in the each cardiac cycle based on the cardiac image(s) of the each cardiac cycle; and a set of target cardiac images may be obtained. Therefore, an optimal phase of each cardiac cycle may be accurately determined, thereby reducing the artifacts caused by cardiac motion, and further improving the image quality of the target cardiac image(s).

Figure 14:
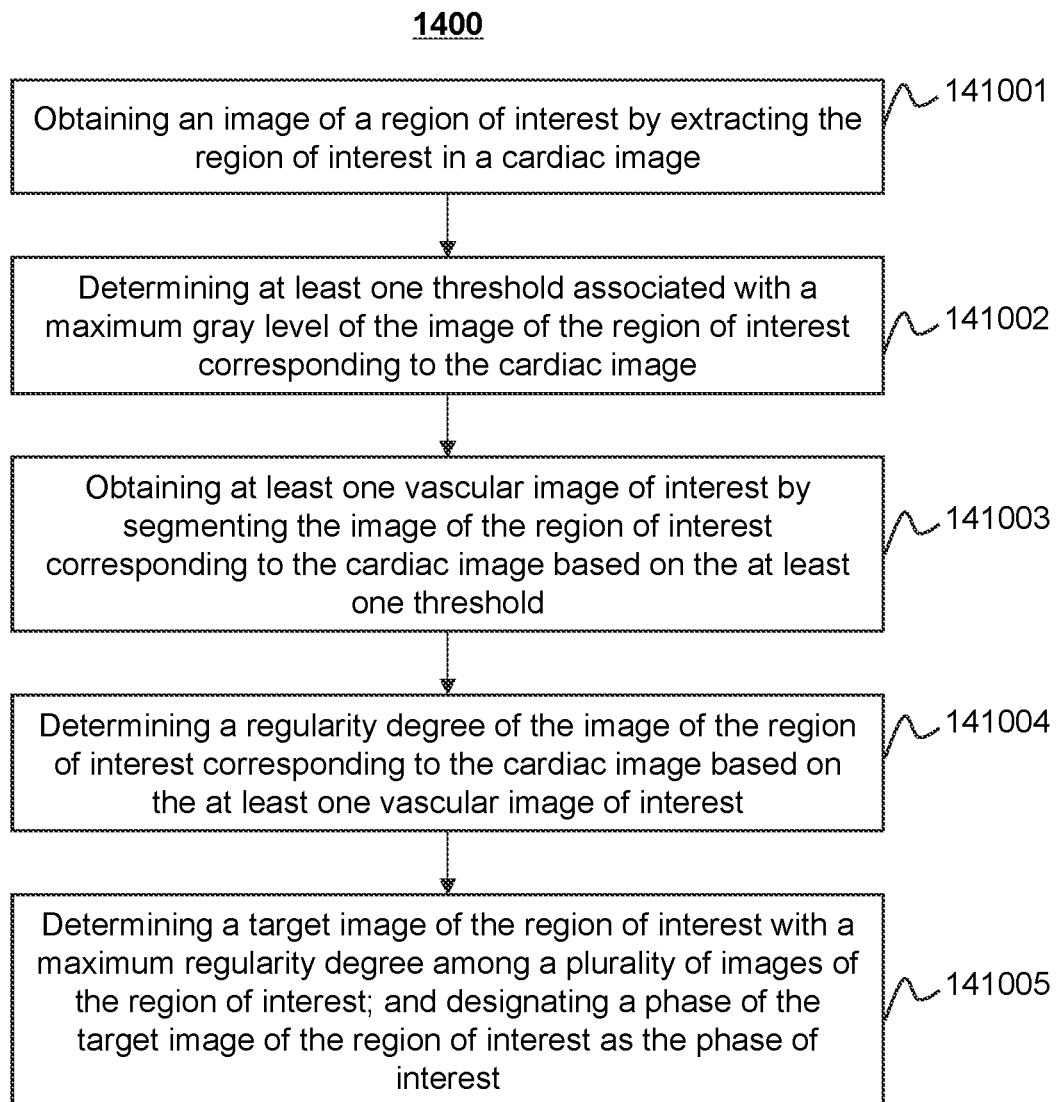
FIG. 14 is a flowchart illustrating an exemplary process for determining a phase of interest in a cardiac cycle according to some embodiments of the present disclosure.

FIG. 14 is a flowchart illustrating an exemplary process for determining a phase of interest in a cardiac cycle according to some embodiments of the present disclosure. In some embodiments, operations 5112 and/or 5114 illustrated in FIG. 5 may be performed according to the process 1400.

In an embodiment, as shown in FIG. 14, an exemplary process for determining an optimal phase for each cardiac cycle is provided. The process 1400 may include the following operations:

In 141001, one or more images of a region of interest may be determined based on cardiac images of the cardiac motion phases in the preset range including the mean phase.

In some embodiments, the processing device 140 (e.g., the second reconstruction module 17500) may perform operation 141001. In some embodiments, an image of a region of interest may be obtained by extracting the region of interest in one (e.g., each) of the cardiac images of the cardiac motion phases in the preset range in a cardiac cycle.

Specifically, in some embodiments, for the cardiac images of the cardiac motion phases within the preset range, the backgrounds of the cardiac images may be mostly the same, and thus redundant information in the cardiac images of the cardiac motion phases within the preset range may be excessive. Therefore, it is desirable to extract a specific region of interest (e.g., a blood vessel) in the cardiac images for further analysis. In one (e.g., each) of the cardiac images of the cardiac motion phases within the preset range, a center of the blood vessel may be selected as a center point, and then a neighborhood matrix R×R around the center point may be selected as elements of an image of the region of interest.

In an embodiment, the image of the region of interest may be determined as:

$$Iroi = Iori\left(\frac{(R-1)}{2} - X^{cen} : X^{cen} + \frac{(R-1)}{2},\right.$$
$$\left.\frac{(R-1)}{2} - Y^{cen} : Y^{cen} + \frac{(R-1)}{2}\right),$$

Equation (27)

where Iroi refers to the image(s) of the region of interest, $X^{cen}$ refers to the abscissa value(s) of point(s) in a centerline of the blood vessel in the cardiac images (or centers of the blood vessel in the cardiac images), $Y^{cen}$ refers to the ordinate value of point(s) in the centerline of the blood vessel in the cardiac images (or centers of the blood vessel in the cardiac images), and R refers to a size of the neighborhood matrix.

In some embodiments, R may be a default value determined by the imaging system 100 or preset by a user or operator via the terminal(s) 130. In some embodiments, the centerline of the blood vessel may include the vascular center(s) illustrated in operation 11702 of FIG. 11.

In 141002, a maximum gray level (of an image of the region of interest) multiplied by one or more preset values may be determined as segment threshold(s).

In some embodiments, the processing device 140 (e.g., the second reconstruction module 17500) may perform operation 141002. In some embodiments, at least one threshold associated with a maximum gray level of the image of the region of interest corresponding to the cardiac image may be determined. The at least one threshold may be referred to as the segment threshold(s).

Specifically, in some embodiments, a top-hat transformation may be performed on the image of the region of interest to obtain a transformed image of the region of interest. The maximum gray level of the transformed image of the region of interest may be selected. The maximum gray level multiplied by the one or more preset values may be designated as the segment threshold(s).

In some embodiments, the transformed image of the region of interest may mainly include information of a target object (e.g., a blood vessel). More descriptions of the determination of the segment threshold(s) may be found elsewhere in the present disclosure (e.g., FIG. 15 and descriptions thereof).

In 141003, at least one vascular image of interest may be obtained based on the image of the region of interest corresponding to the cardiac image and the segment threshold(s).

In some embodiments, the processing device 140 (e.g., the second reconstruction module 17500) may perform operation 141003. In some embodiments, the vascular image(s) of interest may be obtained by segmenting the image of the region of interest corresponding to the cardiac image based on the at least one threshold (i.e., the segment threshold(s)). In some embodiments, the vascular image of interest may include a vascular vessle (e.g., the right coronary artery). More descriptions of the at least one vascular image of interest may be found elsewhere in the present disclosure (e.g., FIGS. 7, 8, and 10, and descriptions thereof). In some embodiments, two or more segmentation operations may be performed based on two or more different thresholds to obtain two or more vascular images of interest. The vascular vessels in the two or more vascular images of interest may have different morphologies. For example, a vascular vessel in a vascular image of interest obtained based on a relatively large threshold may have a regular morphology. As another example, a vascular vessel in a vascular image of interest obtained based on a relatively low threshold may have more details and/or artifacts near the edge of the vascular vessel, and a relatively low regularity. Therefore, the two or more vascular images of interest may include comprehensive information relating to the vascular vessels.

Specifically, in some embodiments, elements of the transformed image of the region of interest that have gray levels greater than a segment threshold may be extracted as a segmentation image corresponding to the segment threshold. A segmentation operation may be performed on the transformed image of the region of interest generated by the top-hat transformation based on a segment threshold, and a segmentation image corresponding to the segment threshold may be obtained. Multiple segmentation images may be obtained by using multiple segment thresholds in segmentation operation(s). Merely by way of example, the transformed image of the region of interest may be segmented based on a first segment threshold, and elements of the transformed image of the region of interest that have gray levels greater than the first segment threshold may be extracted as a first segmentation image; the transformed image of the region of interest may be segmented based on a second segment threshold, and elements of the transformed image of the region of interest that have gray levels greater than the second segment threshold may be extracted as a second segmentation image; the transformed image of the region of interest may be segmented based on a third segment threshold, and elements of the transformed image of the region of interest that have gray levels greater than the third segment threshold may be extracted as a third segmentation image; the transformed image of the region of interest may be segmented based on a fourth segment threshold, and elements of the transformed image of the region of interest that have gray levels greater than the fourth segment threshold may be extracted as a fourth segmentation image.

In some embodiments, a segmentation image may also be referred to as a vascular image of interest.

In 141004, a regularity degree of the image of the region of interest corresponding to the cardiac image may be determined based on the at least one vascular image of interest.

In some embodiments, the processing device 140 (e.g., the second reconstruction module 17500) may perform operation 141004. In some embodiments, a regularity degree of the image of the region of interest corresponding to each cardiac image may be determined based on the at least one vascular image of interest.

Specifically, in some embodiments, a perimeter and an area of a target object may be determined in each segmentation image according to a plurality of segmentation images; a compactness degree of the each segmentation image may be determined according to the perimeter and the area of the target object in the each segmentation image; and a regularity degree of the image of the region of interest may be determined according to the compactness degree of each segmentation image corresponding to the image of the region of interest.

Figure 16:
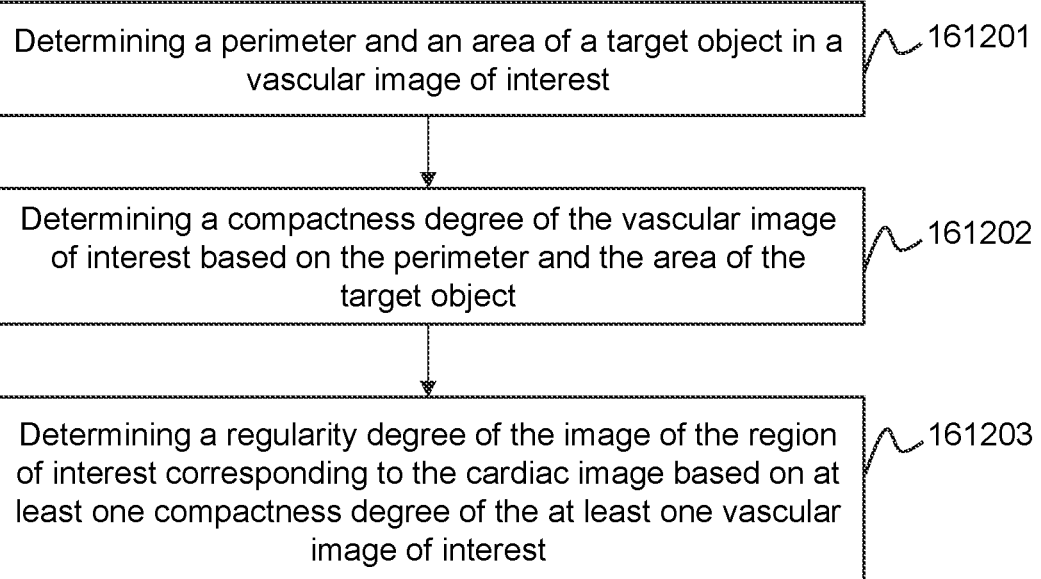
FIG. 16 is a flowchart illustrating an exemplary process for determining regularity degree(s) according to some embodiments of the present disclosure.

More descriptions of the determination of the regularity degree(s) may be found elsewhere in the present disclosure (e.g., FIG. 16 and descriptions thereof).

In 141005, a target image of the region of interest with a maximum regularity degree may be determined among a plurality of images of the region of interest; and a phase of the target image of the region of interest may be designated as the phase of interest.

In some embodiments, the processing device 140 (e.g., the second reconstruction module 17500) may perform operation 141005. In some embodiments, the phase of interest may refer to an optimal phase in a specific cardiac cycle.

Specifically, in some embodiments, a regularity degree may be determined for each image of the region of interest in the preset range of a cardiac cycle; and all regularity degrees of the images of the region of interest in the preset range may be compared to determine a maximum regularity degree. A phase of the target image of the region of interest with the maximum regularity degree may be designated as an optimal phase of the cardiac cycle. Then projection data corresponding to the optimal phase for the cardiac cycle may be selected.

According to the process for determining an optimal phase data of a cardiac cycle, image(s) of a region of interest may be determined based on cardiac image(s) of the cardiac motion phases within the preset range; a top-hat transformation may be performed to obtain a transformed image of the region of interest; a maximum gray level of the elements in an image of the region of interest may be determined; one or more segment thresholds may be determined according to the maximum gray level; the image of the region of interest may be segmented according to the segment threshold(s) to obtain one or more segmentation images; a perimeter and an area of a target object in each segmentation image may be determined; and a compactness degree of the segmentation image may be determined based on the perimeter and the area of the segmentation image. A regularity degree of an image of the region of interest may be determined based on one or more compactness degrees of the one or more segmentation images of the image of the region of interest; and a phase of a target image of the region of interest that has a maximum regularity degree may be designated as an optimal phase of a cardiac cycle. According to the regularity degree(s), the optimal phase of cardiac motion may be determined more efficiently, and the cardiac image of the optimal phase may be determined based on the optimal phase conveniently.

Figure 15:
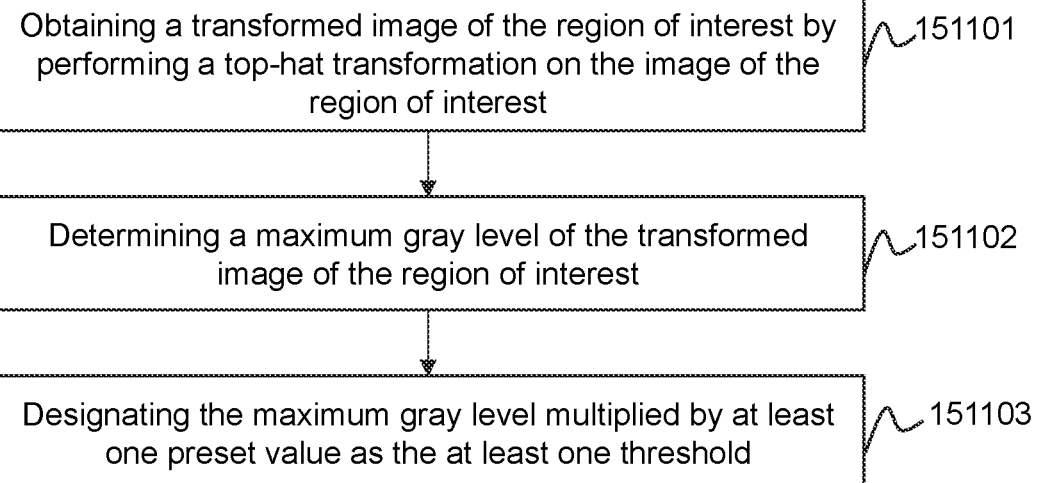
FIG. 15 is a flowchart illustrating an exemplary process for determining segment threshold(s) according to some embodiments of the present disclosure.

FIG. 15 is a flowchart illustrating an exemplary process for determining segment threshold(s) according to some embodiments of the present disclosure. In some embodiments, operation 141002 illustrated in FIG. 14 may be performed according to the process 1500.

In an embodiment, as shown in FIG. 15, an exemplary process for determining segment threshold(s) is provided. The process 1500 may include the following operations:

In 151101, a transformed image of the region of interest may be obtained by performing a top-hat transformation on the image of the region of interest.

In some embodiments, the processing device 140 (e.g., the second reconstruction module 17500) may perform operation 151101. In some embodiments, the top-hat transformation may be performed to enchance the image contrast of the image of the region of interest, facilitating the further processing of the image of the region of interest (e.g., making the threshold(s) more suitable for the segmentation of the images of the region of interest).

Specifically, in some embodiments, the top-hat transformation is an image processing algorithm that may weaken a background in an image and make a target object more prominent. That is, the top-hat transformation of the image of the region of interest may make a target object in the image of the region of interest more prominent. In some embodiments, the target object may include a blood vessel. After the top-hat transformation of the image of the region of interest, the background (in the image of the region of interest) may be weakened and the blood vessel(s) (in the image of the region of interest) may be shown more clearly.

In 151102, a maximum gray level of the transformed image of the region of interest may be determined.

In some embodiments, the processing device 140 (e.g., the second reconstruction module 17500) may perform operation 151102.

Specifically, in some embodiments, the gray levels of all the elements of the transformed image of the region of interest may be extracted, and the gray levels of all the elements may be compared to obtain a maximum gray level of the gray levels.

In 151103, the maximum gray level multiplied by at least one preset value may be designated as the at least one threshold.

In some embodiments, the processing device 140 (e.g., the second reconstruction module 17500) may perform operation 151103.

Specifically, in some embodiments, the maximum gray level multiplied by a preset value may be designated as a segment threshold, and a plurality of segment thresholds may be obtained based on a plurality of preset values. The preset value(s) may be a number between 0 and 1. In some embodiments, multiple segment thresholds may be determined based on multiple preset values, which can facilitate the segmentation of blood vessel(s) that affect (or induce) motion artifacts.

According to the process for determining the segment threshold(s), segment threshold(s) may be determined according to the maximum gray level of the (transformed) image of the region of interest and the preset value(s); and segmentation image(s) may be determined by segmenting the (transformed) image of the region of interest according to the segment threshold(s). Therefore, the maximum gray level may be accurately determined, and the (transformed) image of the region of interest may be segmented more precisely.

FIG. 16 is a flowchart illustrating an exemplary process for determining regularity degree(s) according to some embodiments of the present disclosure. In some embodiments, operation 141004 illustrated in FIG. 14 may be performed according to the process 1600.

In an embodiment, as shown in FIG. 16, an exemplary process for determining regularity degree(s) is provided. The process 1600 may include the following operations:

In 161201, a perimeter and an area of a target object in a vascular image of interest may be determined.

In some embodiments, the processing device 140 (e.g., the second reconstruction module 17500) may perform operation 161201. In some embodiments, a perimeter and an area of a target object in each vascular image of interest may be determined.

Specifically, in some embodiments, according to the obtained segmentation image(s), a perimeter and an area of a target object (e.g., a blood vessel) in one or more (e.g., each) segmentation images may be respectively determined. In some embodiments, the perimeter and the area of the blood vessel in each segmentation image are respectively determined.

In some embodiments, a segmentation image may also be referred to as a vascular image of interest.

In 161202, a compactness degree of the vascular image of interest may be determined based on the perimeter and the area of the target object.

In some embodiments, the processing device 140 (e.g., the second reconstruction module 17500) may perform operation 161202. In some embodiments, the compactness degree may reflect a closeness degree of the element(s) in the vascular image of interest or a region of interest thereof (e.g., the elements corresponding to the target object). The compactness degree may relate to a perimeter and/or an area of a region (e.g., the target object) including a portion or all elements in the vascular image of interest or a region of interest thereof. In some embodiments, the compactness degree may be in direct proportion to the perimeter and/or inversely proportional to the area. For example, the compactness degree of a circle may be 1. In some embodiments, the compactness degree of the vascular image of interest may be determined based on the perimeter and the area of the target object.

Specifically, in some embodiments, the compactness degree may be determined as:

$$Compatness_i = Li/(2\pi \times \sqrt{\frac{Si}{\pi}}),  \quad \text{Equation (28)}$$

where Compatness refers to the compactness degree, Li refers to the perimeter of the target object in an i-th segmentation image, Si refers to the area of the target object in the i-th segmentation image.

In 161203, a regularity degree of the image of the region of interest corresponding to the cardiac image may be determined based on at least one compactness degree of the at least one vascular image of interest.

In some embodiments, the processing device 140 (e.g., the second reconstruction module 17500) may perform operation 161203. In some embodiments, the regularity degree may reflect an orderliness of the element(s) in the image of the region of interest. For example, the orderliness of a polygon may be lower than a circle, and accordingly, the regularity degree of the polygon may be lower than the circle. As another example, if an image has a relatively high level of artifact(s), i.e., the clarity of the boundary (or boundaries) of different regions in the image is relatively low, then the regularity degree of the image may be relatively low. In some embodiments, if an image has a relatively large regularity degree, the image may have a relatively high clarity (or quality) and/or a low level of artifacts. In some embodiments, a regularity degree of the image of the region of interest corresponding to the cardiac image may be determined based on the compactness degree(s) of the vascular image(s) of interest (e.g., the at least one vascular image of interest described in operations 141003 and 141004).

Specifically, in some embodiment, the regularity degree may be determined as:

$$ConIndex = \Sigma_i^N N \times (2 - \min(Compatness_i, 2))/\Sigma N,  \quad \text{Equation (29)}$$

where ConIndex refers to the regularity degree, Compatness refers to the compactness degree, i refers to an ith segmentation image, and N refers to the number of preset values.

In some embodiments, the number of preset values may equal to the number of the segmentation images corresponding to the image of the region of interest.

According to the process for determining the regularity degree, the regularity degree of the image of the region of interest may be determined accurately, the optimal phase of cardiac motion may be determined accurately, and thus, a cardiac image of the optimal phase may be obtained based on the optimal phase.

According to the process for determining the optimal phase, image(s) of a region of interest may be determined based on cardiac image(s) of the cardiac motion phases within the preset range; a top-hat transformation may be performed to obtain a transformed image of the region of interest; a maximum gray level of the elements in an image of the region of interest may be determined; one or more segment thresholds may be determined according to the maximum gray level; the image of the region of interest may be segmented according to the segment threshold(s) to obtain one or more segmentation images; a perimeter and an area of a target object in each segmentation image may be determined; and a compactness degree of the segmentation image may be determined based on the perimeter and the area of the segmentation image. A regularity degree of an image of the region of interest may be determined based on one or more compactness degrees of the one or more segmentation images of the image of the region of interest; and a phase of a target image of the region of interest that has a maximum regularity degree may be designated as an optimal phase of a cardiac cycle. According to the regularity degree(s), the optimal phase of cardiac motion may be determined more efficiently, and the cardiac image of the optimal phase may be determined based on the optimal phase conveniently.

Compared with traditional process(es) for determining the optimal phase, the cardiac image reconstruction process(es) illustrated above may have a higher accuracy, be independent of artificial selection of the region of interest, and may actively identify the vascular image of interest. And in the traditional process(es) for determining the optimal phase, a same optimal phase may be selected for all cardiac cycles. The optimal phase may not be most accurate for each cardiac cycle. Using the process(es) illustrated above, the optimal phase of each cardiac cycle may be determined separately. For patient(s) with unstable heart rate(s), the optimal phase of each cardiac cycle can be obtained. Moreover, in the process(es), requirement(s) for acquisition device(s) may be relatively low, and optimal phase(s) can be selected based on data acquired under unsatisfactory scanning condition(s) and/or acquisition condition(s), thereby improving image quality, and compensating (or reducing) the effects of poorly equipped equipment, poor scanning conditions, and the patient's motion.

It should be understood that although the various operations in the flowcharts of FIGS. 5-16 are displayed as indicated by the arrows, these operations are not necessarily performed in the order indicated by the arrows. Except as explicitly stated herein, there is no strict ordering of the execution of these operations, and these operations may be performed in other orders. Moreover, at least a part of the operations in FIGS. 5-16 may include a plurality of sub-operations or a plurality of stages, and these sub-operations or stages are not necessarily performed at the same time, but may be performed at different times. The operations or stages are also not necessarily executed in sequence, but may be performed alternately with other operations or at least a portion of sub-operations or stages of other operations.

Figure 17:
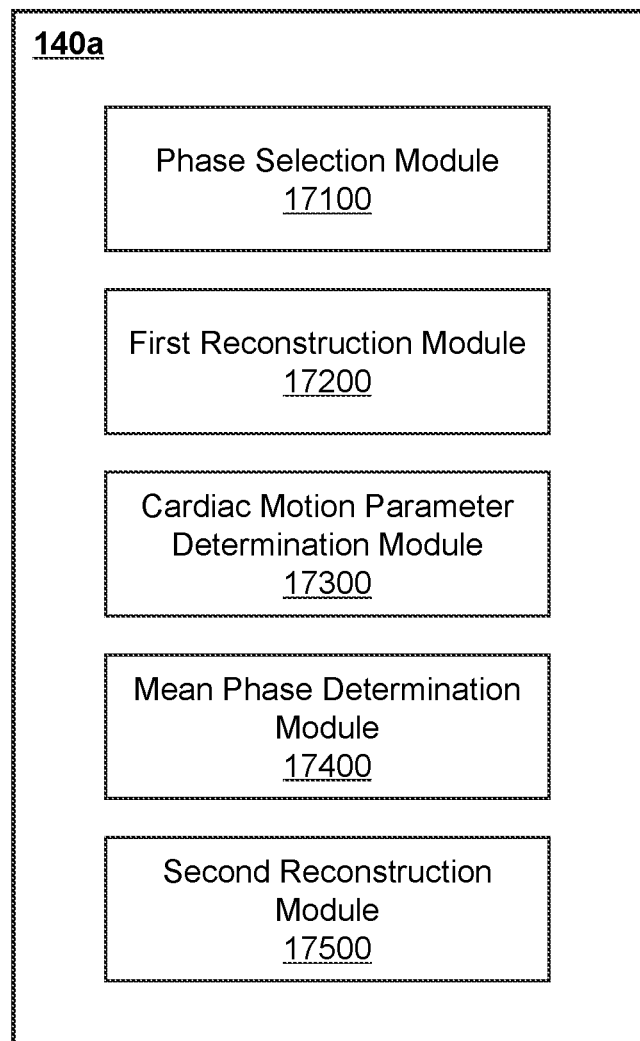
FIG. 17 is a block diagram illustrating an exemplary processing device according to some embodiments of the present disclosure.

FIG. 17 is a block diagram illustrating an exemplary processing device according to some embodiments of the present disclosure.

In some embodiments, as shown in FIG. 17, a block diagram illustrating an exemplary processing device for cardiac image reconstruction is provided. The processing device 140a may include a phase selection module 17100, a first reconstruction module 17200, a cardiac motion parameter determination module 17300, a mean phase determination module 17400, and a second reconstruction module 17500.

The phase selection module 17100 may be configured to select a plurality of cardiac motion phases (e.g., at regular intervals).

The first reconstruction module 17200 may be configured to perform reconstruction operation(s) according to scan data of the plurality of cardiac motion phases, to obtain cardiac image(s) corresponding to the plurality of cardiac motion phases.

The cardiac motion parameter determination module 17300 may be configured to determine cardiac motion parameter(s) of the plurality of cardiac motion phases according to the cardiac image(s) corresponding to the plurality of cardiac motion phases.

A mean phase determination module 17400 may be configured to determine a mean phase according to the cardiac motion parameters of the plurality of cardiac motion phases.

The second reconstruction module 17500 may be configured to designate cardiac image(s) corresponding to the mean phase or the phase of interest as target cardiac image(s).

More descriptions of the processing device 140a may be found in the above descriptions of the cardiac image reconstruction process(es), and the details are not repeated herein. Partial or all of the various modules in the processing device 140a can be implemented as software, hardware, and combinations thereof. The modules may be embedded in or independent of the processing device 140 in a computing device, or may be stored as instructions in the memory of the computing device, so that the processing device 140 may call to perform corresponding operations of the above modules.

In some embodiments, process(es) for determining a mean phase or a phase of interest, and/or generating cardiac image(s) of interest are provided as illustrated above. The information regarding the mean phase or phase of interest may be used to reconstruct target cardiac image(s). Process(es) for reconstructing cardiac image(s) may be described below. More descriptions of the phase selection module 17100 may be found elsewhere in the present disclosure (e.g., FIG. 5 and descriptions thereof). More descriptions of the first reconstruction module 17200 may be found elsewhere in the present disclosure (e.g., FIG. 5 and descriptions thereof). More descriptions of the cardiac motion parameter determination module 17300 may be found elsewhere in the present disclosure (e.g., FIGS. 5-11 and descriptions thereof). More descriptions of the mean phase determination module 17400 may be found elsewhere in the present disclosure (e.g., FIGS. 5, 6, 12 and descriptions thereof). More descriptions of the second reconstruction module 17500 may be found elsewhere in the present disclosure (e.g., FIGS. 5, 13-16 and descriptions thereof).

It should be noted that the determination of the mean phase or the phase of interest may be performed according to a machine learning algorithm (e.g., a deep learning algorithm). In some embodiments, the mean phase or the phase of interest may be determined based on one or more deep neural networks. Merely by way of example, the mean phase or the phase of interest may be determined based on a first deep neural network configured to extract one or more images of a region of interest (e.g., vascular images of interest), and/or a second deep neural network configured to select the mean phase or the phase of interest. In some embodiments, the first deep neural network may be trained using projection data (or raw data) and corresponding images of the region of interest. In some embodiments, images may be reconstructed based on the projection data, and the region of interest (e.g., blood vessel(s)) may be extracted from or labelled in the reconstructed image to obtain the images of the region of interest. In some embodiments, projection data associated with the images of the region of interest may be generated by performing a forward projection on the images of the region of interest. In some embodiments, in the training process of the first deep neural network, the raw data may be used as the input of the first deep neural network, and the projection data associated with the images of the region of interest may be used as the output of the first deep neural network, and accordingly, the parameters (e.g., weight(s), bias(es), etc.) of hidden layer(s) in the first deep neural network may be adjusted. In some embodiments, the second deep neural network may be trained using the projection data associated with the images of the region of interest corresponding to various cardiac motion phases. In some embodiments, cardiac images of the various cardiac motion phases may be reconstructed based on the projection data associated with the images of the region of interest corresponding to the various cardiac motion phases. In some embodiments, the cardiac images may be labeled by a user (e.g., a doctor, an engineer, etc.). In some embodiments, the label(s) of cardiac images of the mean phase or the phase of interest may be set as 1, while the label(s) of other cardiac images may be set as 0. In some embodiments, in the training process of the second deep neural network, the projection data associated with the images of the region of interest corresponding to various cardiac motion phases may be used as the input of the second deep neural network, and the label(s) of the cardiac images of the various cardiac motion phases may be used as the output of the second deep neural network, and accordingly, the parameters (e.g., weight(s), bias(es), etc.) of hidden layer(s) in the second deep neural network may be adjusted. In some embodiments, the first trained deep neural network and the second trained deep neural network may be used to determine the mean phase or the phase of interest based on the raw data.

Figure 18:
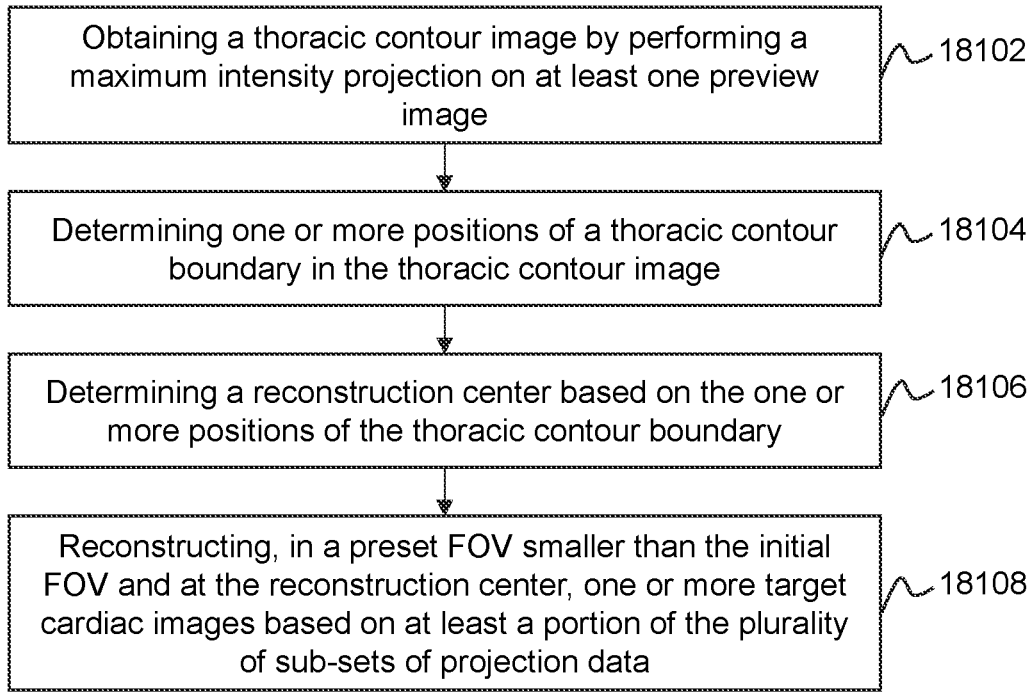
FIG. 18 is a flowchart illustrating an exemplary process for reconstructing cardiac image(s) according to some embodiments of the present disclosure.

FIG. 18 is a flowchart illustrating an exemplary process for reconstructing cardiac image(s) according to some embodiments of the present disclosure.

In an embodiment, as shown in FIG. 18, an exemplary process for cardiac image reconstruction is provided. The process 1800 may include the following operations:

In 18102, a thoracic contour image may be obtained based on a maximum intensity projection of at least one preview image.

In some embodiments, the processing device 140 (e.g., the maximum intensity projection module 28100) may perform operation 18102. In some embodiments, a plurality of projection data in a plurality of cardiac cycles may be obtained. The plurality of projection data may be generated by an imaging device (e.g., the scanner 110). The plurality of projection data may include a plurality of sub-sets of projection data. In some embodiments, a sub-set of projection data may correspond to a cardiac motion phase of a cardiac cycle. In some embodiments, the preview image(s) may be reconstructed in an initial field of view (FOV) based on at least a portion of the plurality of projection data. In some embodiments, the thoracic contour image may be obtained by performing a maximum intensity projection on the at least one preview image. In some embodiments, the preview image(s) may include image(s) in the transverse plane.

Specifically, in some embodiments, a preview image may be an original image generated by a computing device (e.g., the computing device 200) after a preliminary processing of the received data. In some embodiments, the preview image may be an original image reconstructed in a relatively large field of view (FOV) (or the initial FOV) (e.g., an FOV with a diameter of at least 500 mm). The original image may reflect (or illustrate) a structure of the entire thoracic cavity of an object (e.g., a patient). In the field of medical imaging technology, in order to enhance (or improve) the imaging effect of a target site of a patient, a contrast agent may be usually injected or administered to the target site. The preview image(s) may be original image(s) of the thoracic cavity obtained based on image data collected after an injection or administration of the contrast agent. In some embodiments, one or more preview images may be selected, and the preview image(s) may be segmented respectively to obtain a first set of images reflecting position(s) of thoracic bone(s) and location(s) of the contrast agent. In some embodiments, an opening operation may be performed on the first set of images respectively to obtain a second set of images. The opening operation may smooth contour(s) of the object or a portion thereof (e.g., the thoracic cavity), break narrow gap(s) (e.g., between different regions of the object), and/or eliminate fine protrusion(s) (e.g., fine protrusion region(s) generated after segmentation). In some embodiments, relatively thin edge(s) (e.g., thin edge region(s) generated after segmentation) may be removed by performing an opening operation on the first set of images respectively, and the second set of images reflecting (or illustrating) the position(s) of the contrast agent may be obtained. A maximum intensity projection operation may be performed on the first set of images and the second set of images, respectively, and initial thoracic contour image(s) may be obtained.

Figure 19:
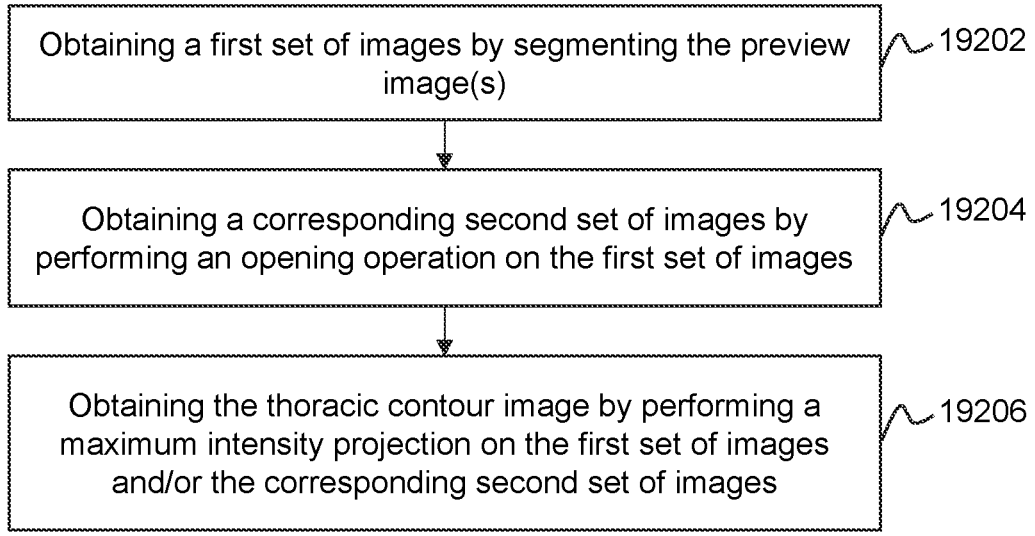
FIG. 19 is a flowchart illustrating an exemplary process for determining a thoracic contour image according to some embodiments of the present disclosure.

In some embodiments, a first initial thoracic contour image (e.g., a maximum intensity projection image of the first set of images illustrated in FIG. 19) may be obtained based on a maximum intensity projection of the first set of images, and a second initial thoracic contour image (e.g., a maximum intensity projection image of the second set of images illustrated in FIG. 19) may be obtained based on a maximum intensity projection of the second set of images. In some embodiments, a thoracic contour image may be determined based on the first initial thoracic contour image and the second initial thoracic contour image. For example, the thoracic contour image may be determined based on a difference between the first initial thoracic contour image and the second initial thoracic contour image. In some embodiments, the thoracic contour image include information relating to at least a portion of the bones in the thorax. An exemplary thoracic contour image may be seen in FIG. 24. In some embodiments, the opening operation may include an erosion operation followed by a dilation operation. More descriptions of the determination of the thoracic contour image may be found elsewhere in the present disclosure (e.g., FIGS. 19 and 21 and descriptions thereof).

In 18104, one or more positions of a thoracic contour boundary in the thoracic contour image may be determined based on the thoracic contour image.

In some embodiments, the processing device 140 (e.g., the boundary determination module 28200) may perform operation 18104. A position of the thoracic contour boundary may refer to a position of an element or an element cluster in the thoracic contour image. In some embodiments, the processing device 140 may segment the thoracic contour image for determining the position(s) of the thoracic contour boundary.

Specifically, in some embodiments, the position(s) of the thoracic contour boundary may include a first position of a leftmost boundary (of the thoracic contour boundary), a second position of a rightmost boundary (of the thoracic contour boundary), and/or a third position of an uppermost boundary (of the thoracic contour boundary). In some embodiments, the first position of the leftmost boundary may be a physical position of the leftmost boundary of the thoracic contour boundary; the second position of the rightmost boundary may be a physical position of the rightmost boundary of the thoracic contour boundary; the third position of the uppermost boundary may be a physical position of the uppermost boundary of the thoracic contour boundary. In some embodiments, the obtained thoracic contour image may be segmented, and a left thoracic contour image and a right thoracic contour image may be obtained. Accordingly, the first position of the leftmost boundary, the second position of the rightmost boundary, and/or the third position of the uppermost boundary may be determined based on the left thoracic contour image, the right thoracic contour image, and the thoracic contour image.

In some embodiments, the physical position may refer to a position in a coordinate system of the gantry. In some embodiments, a rotation center of the gantry may be designated as the coordinate origin. In some embodiments, a position in a coordinate system of the image domain (also referred to as image position) may be transformed to a physical position in the coordinate system of the gantry (e.g., according to a predetermined transformation matrix or an equation (e.g., Equation (37) or (39))). More descriptions of the determination of the position(s) of the thoracic contour boundary may be found elsewhere in the present disclosure (e.g., FIGS. 20-21 and descriptions thereof).

In 18106, a reconstruction center may be determined based on the one or more positions of the thoracic contour boundary.

In some embodiments, the processing device 140 (e.g., the center reconstruction module 28300) may perform operation 18106. In some embodiments, the processing device 140 may determine the reconstruction center based on the one or more positions of the thoracic contour boundary. In some embodiments, the reconstruction center may be a center of gravity, a geometrical center, or a center determined based on the position(s) of the thoracic contour boundary according to a rule (see Equations (56)-(57)).

Specifically, in some embodiments, a thoracic contour center may be determined based on the first position of the leftmost boundary, the second position of the rightmost boundary, and/or the third position of the uppermost boundary. In some embodiments, according to a position of the heart in the thoracic cavity, the reconstruction center may be determined as a position in an upper left region of the thoracic contour center.

In some embodiments, the upper left region of the thoracic contour center may refer to an upper left region in the image domain relative to the thoracic contour center. More descriptions of the determination of the reconstruction center may be found elsewhere in the present disclosure (e.g., FIG. 21 and descriptions thereof).

In 18108, one or more target cardiac images may be reconstructed, in a preset FOV and at the reconstruction center.

In some embodiments, the processing device 140 (e.g., the image reconstruction module 28400) may perform operation 18108. In some embodiments, the target cardiac image(s) may be reconstructed, in a preset FOV (also referred to as a preset reconstruction FOV) and at the reconstruction center, based on at least a portion of the plurality of sub-sets of projection data. In some embodiments, the preset FOV may be smaller than the initial FOV. For example, the diameter of the initial FOV may be 200 mm, while the diameter of the preset FOV may be 150 mm. In some embodiments, the preset FOV may be set according to a default setting of the imaging system 100 or preset by a user or operator via the terminal(s) 130. In some embodiments, the reconstruction of the target cardiac image(s) may refer to a multi-phase reconstruction. The multi-phase reconstruction may refer to the reconstruction of images of corresponding phases (e.g., the sampled cardiac motion phase illustrated in FIGS. 5, 6-7, and 11-12).

Specifically, in some embodiments, the multi-phase reconstruction may be performed according to the determined reconstruction center and the preset reconstruction FOV. In some embodiments, the coronary artery may have a curved shape in an axial direction of the thoracic cavity, and accordingly, position(s) of the coronary artery in the axial direction of the thoracic cavity may be inconstant. Therefore, in some embodiments, the preset reconstruction FOV may not be set too small. In some embodiments, an exemplary reconstruction FOV may have a diameter of 80 mm. The reconstruction FOV may be an FOV for multi-phase reconstruction.

According to the process for reconstructing cardiac image(s), the thoracic contour image may be obtained based on preview image(s) and a maximum intensity projection of the preview image(s); first position(s) of a leftmost boundary, second position(s) of a rightmost boundary, and/or third position(s) of an uppermost boundary may be determined according to the thoracic contour image; and a reconstruction center may be determined based on the first position(s), second position(s), and/or the third position(s). A multi-phase reconstruction may be performed on projection data of an object according to the reconstruction center and the preset reconstruction FOV to obtain cardiac image(s). Compared with a conventional reconstruction FOV with a diameter of 200 mm, cardiac image(s) reconstructed based on the preset reconstruction FOV illustrated above may have a relatively high resolution (e.g., the resolution may be tripled). Besides, the determination process based on global element operation or local element operation may be optimized using the process above, and the operation efficiency may be improved.

Figure 22:
FIG. 22 is an exemplary maximum intensity projection image relating to bone(s) and a contrast agent according to some embodiments of the present disclosure.
Figure 23:
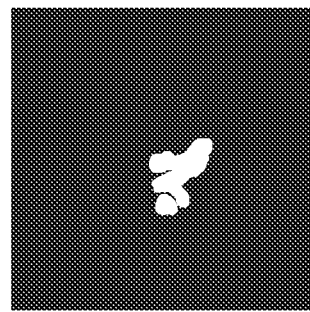
FIG. 23 is an exemplary maximum intensity projection image relating to a contrast agent according to some embodiments of the present disclosure.
Figure 24:
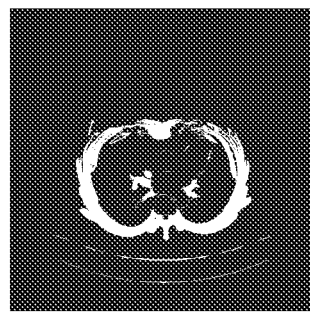
FIG. 24 is an exemplary thoracic contour image according to some embodiments of the present disclosure.

FIG. 19 is a flowchart illustrating an exemplary process for determining a thoracic contour image according to some embodiments of the present disclosure. FIG. 22 is an exemplary maximum intensity projection image relating to bone(s) and a contrast agent according to some embodiments of the present disclosure. FIG. 23 is an exemplary maximum intensity projection image relating to a contrast agent according to some embodiments of the present disclosure. FIG. 24 is an exemplary thoracic contour image according to some embodiments of the present disclosure. FIGS. 22-24 may be binary images. As shown in FIGS. 22-24, element(s) that represent bone(s) and/or the contrast agent may have a first value, while element(s) that do not represent bone(s) and/or the contrast agent may have a second value. The first value and the second value may be different. For example, in FIGS. 22-24, the first value may be 1, while the second value may be 0. As another example, the first value may be 0, while the second value may be 1. The values are merely provided for the purposes of illustration, and not intended to limit the scope of the present disclosure.

In some embodiments, as shown in FIGS. 19 and 22-24, an exemplary process for determining a thoracic contour image is provided. The process 1900 may include the following operations:

In 19202, a first set of images may be obtained by segmenting the preview image(s).

In some embodiments, the processing device 140 (e.g., the maximum intensity projection module 28100 (e.g., the first image segmenting unit 29110)) may perform operation 19202. In some embodiments, a first intermediate image may be obtained by segmenting a preview image, and accordingly, a first set of images (including a plurality of first intermediate images) may be obtained by segmenting a plurality of preview images.

Specifically, in some embodiments, the preview image(s) may be original image(s) obtained after preliminary processing of data received by a computing device (e.g., the computing device 200). The preview image(s) may be original image(s) reconstructed based on a relatively large FOV (e.g., an FOV with a diameter larger than 500 mm). In some embodiments, the preview image(s) can show the structure of at least a portion of (e.g., the entire) thoracic cavity of the target object. In medical imaging technology, in order to enhance the image effect of a target site of an object (e.g., a patient), a contrast agent may be injected or administered to a target site (e.g., the coronary artery, the ventricle). Data obtained after injection or administration of the contrast agent may be preliminarily processed, and original image(s) of the thoracic cavity may be obtained. The original image(s) may be regarded as the preview image(s). In some embodiments, multiple preview images may be selected, and the preview images may be segmented, respectively, to obtain a first set of images. The first set of images may reflect the position(s) of bone(s) of the thoracic cavity and the position(s) of the contrast agent.

In some embodiments, the first set of images may be obtained by segmenting a plurality of preview images according to the following equation:

$$IPB1z(i, j) = \begin{cases} 1, & \text{if } IPO_z(i, j) > TB1 \\ 0, & \text{if } IPO_z(i, j) \leq TB1 \end{cases}, \quad \text{Equation (30)}$$

where $IPO_z(i, j)$ denotes the element(s) of the zth preview image; TB1 denotes a threshold relating to a high density structure of the target object; IPB1 denotes image(s) that are related to bone(s) and the contrast agent and are obtained by segmenting preview image(s); $IPB1_z(i, j)$ denotes the element(s) of the zth image of the images relating to the bone(s) and the contrast agent.

In some embodiments, the first set of images may be binary images.

In 19204, a corresponding second set of images may be obtained by performing an opening operation on the first set of images.

In some embodiments, the processing device 140 (e.g., the maximum intensity projection module 28100 (e.g., the opening operation unit 29120)) may perform operation 19204. In some embodiments, a corresponding second intermediate image may be obtained by performing an opening operation on a first intermediate image, and accordingly, a second set of images (including a plurality of second intermediate images) may be obtained by performing an opening operation on the first set of images respectively. In some embodiments, the second set of images may be binary images.

Specifically, in some embodiments, according to the obtained first set of images, an opening operation may be performed on the first set of images to obtain a second set of images. The opening operation may be performed to smooth the contour(s) of the object or a portion thereof (e.g., a contour of an organ of the object), break narrow gap(s) (or discontinuities), and/or eliminate fine protrusion(s). Relatively thin edge(s) in the first set of images may be removed or reduced by performing an opening operation on the first set of images separately, and a second set of images reflecting position(s) of the contrast agent may be obtained.

In some embodiments, the second set of images may be obtained by performing the opening operation on the first set of images according to the following equation:

$$IPB2 = (IPB1 \ominus se\_b1) \oplus se\_b1, \quad \text{Equation (31)}$$

where IPB1 denotes image(s) that are related to bone(s) and the contrast agent (i.e., the first set of images) and are obtained by segmenting preview image(s); IPB2 denotes image(s) relating to the contrast agent (i.e., the second set of images) that are obtained by performing an opening operation on the image(s) relating to bone(s) and the contrast agent; se_b1 denotes a structure element in morphology operation(s); e denotes a corrosion operation; $\oplus$ denotes an expansion operation.

In 19206, the thoracic contour image may be obtained by performing a maximum intensity projection on the first set of images and/or the corresponding second set of images.

In some embodiments, the processing device 140 (e.g., the maximum intensity projection module 28100 (e.g., the maximum intensity projection unit 29130)) may perform operation 19206.

Specifically, in some embodiments, the obtained first set of images and the second set of images may be respectively subjected to the maximum intensity projection to obtain the thoracic contour image. The maximum intensity projection(s) may be generated based on element(s) having a maximum intensity (or density) along each projection ray directed to the patient's target site. That is, if the projection ray passes through original image(s) of the patient's target site, the element(s) with the highest intensity (or density) in the image(s) may be retained and projected onto a two-dimensional plane, thereby forming a maximum intensity projection image of the patient's target site.

More specifically, in some embodiments, the first set of images may be subjected to the maximum intensity projection in the axial direction of the thoracic cavity to obtain a maximum intensity projection image (see FIG. 22) of the first set of images. If the projection ray passes through the image(s) relating to the bone(s) and the contrast agent in the axial direction of the thoracic cavity, the element(s) with the highest intensity (or density) in the image(s) may be retained and projected onto a two-dimensional plane, thereby forming a maximum intensity projection image of the first set of images.

In some embodiments, the first maximum intensity projection sub-unit 30131 may perform a maximum intensity projection on the first set of images in the axial direction of the thoracic cavity to obtain the maximum intensity projection image of the first set of images. In some embodiments, the maximum intensity projection image of the first set of images may be a binary image.

In some embodiments, the maximum intensity projection image of the first set of images may be obtained by projection in the axial direction of the thoracic cavity, which can be represented as the following equation:

$$IM_{B1}(i,j) = \max(IPB1_z(i,j)), z=1,2,\ldots N, \quad \text{Equation (32)}$$

where $IPB1_z(i, j)$ denotes the element(s) of the zth image of the images relating to the bone(s) and the contrast agent (i.e., the first set of images); N denotes the number of images relating to the bone(s) and the contrast agent; $IM_{B1}$ denotes the maximum intensity projection image of the image(s) relating to the bone(s) and the contrast agent (see FIG. 22); $IM_{B1}(i, j)$ denotes the gray levels of the element(s) of the maximum intensity projection image of the image(s) relating to the bone(s) and the contrast agent.

A maximum intensity projection may be performed on the second set of image(s) in the axial direction of the thoracic cavity to obtain a maximum intensity projection image (see FIG. 23) of the second set of images. If the projection ray passes through the image(s) relating to the contrast agent in the axial direction of the thoracic cavity, the element(s) with the highest intensity (or density) in the image(s) may be retained and projected onto a two-dimensional plane, thereby forming a maximum intensity projection image of the second set of images.

In some embodiments, the second maximum intensity projection sub-unit 30132 may perform a maximum intensity projection on the second set of images in the axial direction of the thoracic cavity to obtain the maximum intensity projection image of the second set of images. In some embodiments, the maximum intensity projection image of the second set of images may be a binary image.

In some embodiments, the maximum intensity projection image of the second set of images may be obtained by projection in the axial direction of the thoracic cavity, which can be represented as the following equation:

$$IM_{B2}(i,j) = \max(IPB2_z(i,j)), z=1,2,\ldots N, \quad \text{Equation (33)}$$

where $IPB2_z(i, j)$ denotes the element(s) of the zth image of the images relating to the contrast agent (i.e., the second set of images); N denotes the number of the images relating to the contrast agent; $IM_{B2}$ denotes the maximum intensity projection image of the images relating to the contrast agent; $IM_{B2}(i, j)$ denotes the element(s) of the maximum intensity projection image of the images relating to the contrast agent.

In some embodiments, a difference between the maximum intensity projection image of the first set of images and the maximum intensity projection image of the second set of images may be determined as a thoracic contour image (see FIG. 24).

In some embodiments, the difference may be a subtraction between the maximum intensity projection image of the first set of images and the maximum intensity projection image of the second set of images. Specifically, the difference may be a subtraction between values of the elements of the maximum intensity projection image of the first set of images and values of corresponding elements of the maximum intensity projection image of the second set of images. In some embodiments, the difference determination sub-unit 30133 may determine the difference between the maximum intensity projection image of the first set of images and the maximum intensity projection image of the second set of images to obtain a thoracic contour image. In some embodiments, the thoracic contour image may be a binary image.

In some embodiments, the thoracic contour image may be determined based on the difference between the maximum intensity projection image of the first set of images and the maximum intensity projection image of the second set of images, which may be represented as the following equation:

$$IM_{st}(i, j) = \begin{cases} IM_{B1}(i, j), & \text{if } IM_{B2}(i, j) \leq 0 \\ 0, & \text{if } IM_{B2}(i, j) > 0 \end{cases} \quad \text{Equation (34)}$$

where $IM_{B1}$ denotes the maximum intensity projection image of the images relating to the bone(s) and the contrast agent; $M_{B1}(i, j)$ denotes the element(s) of the maximum intensity projection image of the images relating to the bone(s) and the contrast agent; $IM_{B2}$ denotes the maximum intensity projection image of the images relating to the contrast agent (see FIG. 23); $IM_{B2}(i, j)$ denotes the element(s) of the maximum intensity projection image of the images relating to the contrast agent; $IM_{st}$ denotes a thoracic contour image; $IM_{st}(i, j)$ denotes the element(s) of the thoracic contour image.

According to the process for determining a thoracic contour image, a plurality of preview images may be segmented to obtain a first set of images; an opening operation may be performed on the first set of images to obtain a second set of images; a maximum intensity projection may be performed respectively on the first set of images and the second set of images; and/or a subtraction between the maximum intensity projection image of the first set of images and the maximum intensity projection image of the second set of images may be determined to generate the thoracic contour image. The thoracic contour image can be obtained using the maximum intensity projection more accurately, which can remove the interferences of relatively thin edge(s) more effectively.

Figure 20:
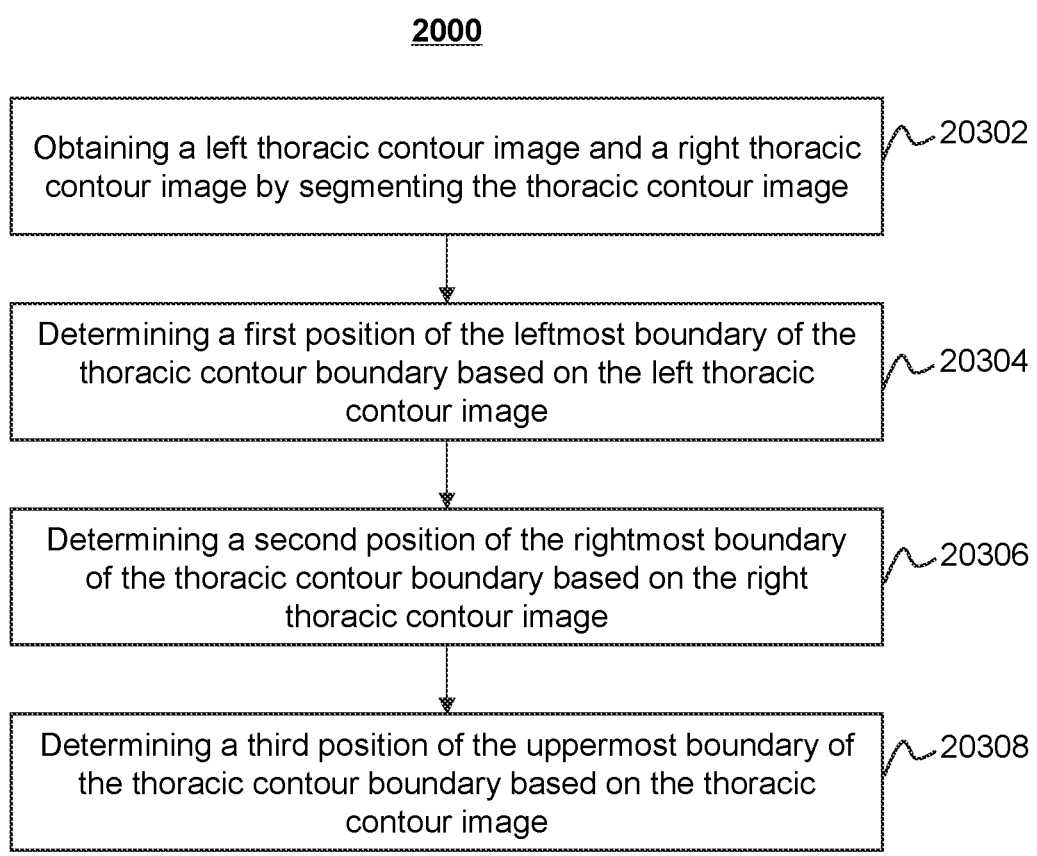
FIG. 20 is a flowchart illustrating an exemplary process for determining one or more positions of a thoracic contour boundary according to some embodiments of the present disclosure.
Figure 25:
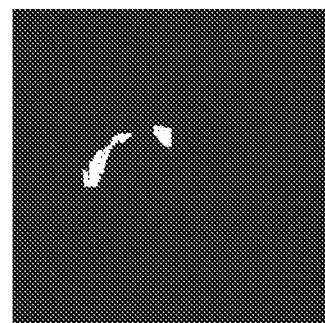
FIG. 25 is an exemplary left thoracic contour image according to some embodiments of the present disclosure.
Figure 26:
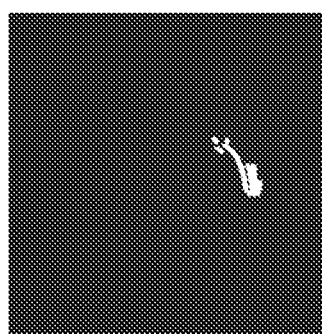
FIG. 26 is an exemplary right thoracic contour image according to some embodiments of the present disclosure.
Figure 27:
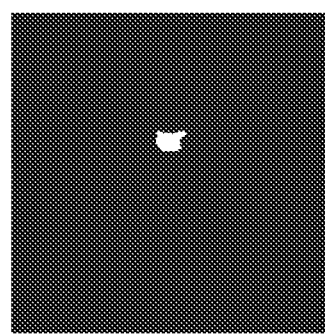
FIG. 27 is an image illustrating a region to be analyzed according to some embodiments of the present disclosure.

FIG. 20 is a flowchart illustrating an exemplary process for determining one or more positions of a thoracic contour boundary according to some embodiments of the present disclosure. FIG. 25 is an exemplary left thoracic contour image according to some embodiments of the present disclosure. FIG. 26 is an exemplary right thoracic contour image according to some embodiments of the present disclosure. FIG. 27 is an image illustrating a region to be analyzed according to some embodiments of the present disclosure.

In some embodiments, as shown in FIGS. 20 and 25-27, an exemplary process for determining one or more positions of a thoracic contour boundary in a thoracic contour image is provided. The process may include the following operations:

In 20302, a left thoracic contour image and/or a right thoracic contour image may be obtained by segmenting the at least one thoracic contour image.

In some embodiments, the processing device 140 (e.g., the boundary determination module 28200 (e.g., the second image segmentation unit 31210)) may perform operation 20302. In some embodiments, the positions of the thoracic contour boundary may refer to the boundary positions of the thoracic contour image. The position(s) (or physical position(s)) of thoracic contour boundary illustrated below may refer to relative position(s) in the thoracic contour image.

Specifically, in some embodiments, the boundary positions of the thoracic contour image may include a leftmost boundary position, a rightmost boundary position, and/or an uppermost boundary position. In some embodiments, the leftmost boundary position may be a physical position of the leftmost boundary of the thoracic contour image. The rightmost boundary position may be a physical position of the rightmost boundary of the thoracic contour image. The uppermost boundary position may be a physical position of the uppermost boundary of the thoracic contour image. In some embodiments, according to the obtained thoracic contour image, segmentation may be performed on the thoracic contour image, and a left thoracic contour image (see FIG. 25) and/or a right thoracic contour image (see FIG. 26) may be obtained.

In some embodiments, the segmentation of the thoracic contour image may be performed based on the positions of the elements of the thoracic contour image. An exemplary segmentation of the thoracic contour image may be performed according to Equations (35)-(36).

In some embodiments, the segmentation of the thoracic contour image to obtain the left thoracic contour image and the right thoracic contour image may be represented as the following equation:

$$IM_l(i, j) = \begin{cases} IM_{st}(i, j), & \text{if } j \leq M/2 \\ 0, & \text{else} \end{cases}, \quad \text{Equation (35)}$$

$$IM_r(i, j) = \begin{cases} IM_{st}(i, j), & \text{if } j \geq M/2 \\ 0, & \text{else} \end{cases}, \quad \text{Equation (36)}$$

where $IM_{st}$ denotes a thoracic contour image; $IM_{st}(i, j)$ denotes the element(s) of the thoracic contour image; $IM_l$ denotes the left thoracic contour image; $IM_l(i, j)$ denotes the element(s) of the left thoracic contour image; $IM_r$ denotes the right thoracic contour image; $IM_r(i, j)$ denotes the element(s) of the right thoracic contour image; M denotes the matrix size of the thoracic contour image.

In 20304, a first position of the leftmost boundary of the thoracic contour boundary may be determined based on the left thoracic contour image.

In some embodiments, the processing device 140 (e.g., the boundary determination module 28200 (e.g., the left boundary determination unit 31220)) may perform operation 20304.

Specifically, in some embodiments, a largest connected domain (also referred as a first maximum connected domain)

may be determined according to the left thoracic contour image, and elements in the largest connected domain of the left thoracic contour image may be selected. The connected domain may correspond to a region in a complex plane. If a simple closed curve is used in the complex plane, and the internal of the closed curve always belongs to the region, then the region is a connected domain. The upper part of the right coronary in the largest connected domain of the left thoracic contour image may be selected, and the leftmost boundary position may be determined.

In some embodiments, the processing device 140 may determine a first maximum connected domain in the left thoracic contour image, and select a first target region including at least a portion of a left thoracic contour in the first maximum connected domain. In some embodiments, the first target region may include elements in the first maximum connected domain of the left thoracic contour image. In some embodiments, the at least a portion of the left thoracic contour may include a right coronary. In some embodiments, the processing device 140 may select a first region of interest including the right coronary in the first target region, and determine the first position of the leftmost boundary of the thoracic contour boundary based on the first region of interest. In some embodiments, the first region of interest may include the upper part of the right coronary in the first maximum connected domain of the left thoracic contour image.

In some embodiments, the first connected domain determination sub-unit 32221 may determine the maximum connected domain according to the left thoracic contour image, and select elements in the first maximum connected domain of the left thoracic contour image. In some embodiments, the left boundary determination sub-unit 32222 may select elements in an upper part of the right coronary in the first maximum connected domain of the left thoracic contour image, and determine (the first position of) the leftmost boundary.

In some embodiments, the leftmost boundary position may be determined according to the following equations:

$$Pos_l = -\left(Pix_l - \left(\frac{M-1}{2}\right)\right) \times Spacing_{pre}, \quad \text{Equation (37)}$$

$$Pix_l = \min(j|(i, j) \in IM_l(i, j)), \quad \text{Equation (38)}$$

where $Pix_l$ denotes the leftmost element position of the left thoracic contour image (i.e., the image position of the leftmost element); $Spacing_{pre}$ denotes the resolution of the elements (of the left thoracic contour image); $Pos_l$ denotes the leftmost boundary position of the thoracic contour image (i.e., the physical position of the leftmost boundary); M denotes the matrix size of the thoracic contour image; $IM_l$ denotes the left thoracic contour image.

In some embodiments, the resolution of the left thoracic contour image may be the same as the resolution of the right thoracic contour image, the resolution of the thoracic contour image, and/or the resolution of the preview image(s). In some embodiments, matrix size of the left thoracic contour image may be the same as the matrix size of the right thoracic contour image, the matrix size of the thoracic contour image, and/or the matrix size of the preview image(s).

In 20306, a second position of the rightmost boundary of the thoracic contour boundary may be determined based on the right thoracic contour image.

In some embodiments, the processing device 140 (e.g., the boundary determination module 28200 (e.g., the right boundary determination unit 31230)) may perform operation 20306.

Specifically, in some embodiments, a largest connected domain (also referred as a second maximum connected domain) may be determined according to the right thoracic contour image, and elements in the largest connected domain of the right thoracic contour image may be selected. The connected domain may correspond to a region in a complex plane. If a simple closed curve, which may form a region surrounded by the curve, is used in the complex plane, and the internal of the closed curve always belongs to the region, then the region is a connected domain. The upper part of the right coronary in the largest connected domain of the right thoracic contour image may be selected, and the rightmost boundary position may be determined.

In some embodiments, the processing device 140 may determine a second maximum connected domain in the right thoracic contour image, and select a second target region including at least a portion of a right thoracic contour in the second maximum connected domain. In some embodiments, the second target region may include elements in the second maximum connected domain of the right thoracic contour image. In some embodiments, the at least a portion of the right thoracic contour may include a right coronary. In some embodiments, the processing device 140 may select a second region of interest including the right coronary in the second target region, and determine the second position of the rightmost boundary of the thoracic contour boundary based on the second region of interest. In some embodiments, the second region of interest may include the upper part of the right coronary in the second maximum connected domain of the right thoracic contour image.

In some embodiments, the second connected domain determination sub-unit 33231 may determine the maximum connected domain according to the right thoracic contour image, and select elements within the second maximum connected domain of the right thoracic contour image. In some embodiments, the right boundary determination sub-unit 33232 may select elements in an upper part of the right coronary in the second maximum connected domain of the right thoracic contour image, and determine the rightmost boundary position.

In some embodiments, the rightmost boundary position may be determined according to the following equations:

$$Pos_r = -\left(Pix_r - \left(\frac{M-1}{2}\right)\right) \times Spacing_{pre}, \quad \text{Equation (39)}$$

$$Pix_r = \max(j|(i, j) \in IM_r(i, j)), \quad \text{Equation (40)}$$

where $Pix_r$ denotes the rightmost element position of the right thoracic contour image (i.e., the image position of the rightmost element); $Spacing_{pre}$ denotes the resolution of the elements (of the right thoracic contour image); $Pos_r$ denotes the rightmost boundary position of the thoracic contour image (i.e., the physical position of the rightmost boundary); M denotes the matrix size of the thoracic contour image; $IM_r$ denotes the right thoracic contour image.

In 20308, a third position of the uppermost boundary of the thoracic contour boundary may be determined based on the at least one thoracic contour image.

In some embodiments, the processing device 140 (e.g., the boundary determination module 28200 (e.g., the upper boundary determination unit 31240)) may perform operation 20308.

Specifically, in some embodiments, a region to be analyzed (e.g., the region to be analyzed in FIG. 27) may be determined in the thoracic contour image according to the rightmost position of the left thoracic contour image, the leftmost position of the right thoracic contour image, and the lowest position of the second set of images. The second set of images may include image(s) reflecting the location(s) of the elements representing the contrast agent. The largest connected domain may be determined according to the region to be analyzed, and elements in the largest connected domain may be selected. According to the elements in the largest connected domain of the region to be analyzed, the uppermost boundary position may be determined.

In some embodiments, the regions to be analyzed may also be referred to as a candidate region of interest. In some embodiments, the candidate region of interest determination sub-unit 34241 may determine the region to be analyzed in the thoracic contour image according to the rightmost position of the left thoracic contour image, the leftmost position of the right thoracic contour image, and the lowest position of the second set of images. In some embodiments, the third connected domain determination sub-unit 34242 may determine a third maximum connected domain according to the region to be analyzed, and select elements within the third maximum connected domain. In some embodiments, the upper boundary determination sub-unit 34243 may determine the uppermost boundary position according to the elements of the thoracic contour image in the third maximum connected domain of the candidate region of interest. In some embodiments, the processing device 140 may determine the third maximum connected domain in the candidate region of interest, and select a third target region of the thoracic contour image in the third maximum connected domain. The third target region may include at least a portion of a thoracic contour. In some embodiments, the third target region may include elements of the thoracic contour image in the third maximum connected domain of the candidate region of interest. In some embodiments, the region to be analyzed (also referred to as the candidate region of interest) may include one or more sternums. In some embodiments, the determination of the uppermost boundary position based on the region to be analyzed may eliminate or reduce the effect of one or more regions above the sternum(s) on the further segmentation (or extraction) of the right coronary.

In some embodiments, the region to be analyzed may be determined in the thoracic contour image based on the rightmost position of the left thoracic contour image, the leftmost position of the right thoracic contour image, and the lowest position of the second set of images according to the following equation:

$$\text{Irib} = \text{IM}_{st}(1:id, id1:id2), \quad \text{Equation (41)}$$

where id denotes the lowest y position of the set of images relating to the contrast agent; id1 denotes the rightmost x position of the left thoracic contour image; id2 denotes the leftmost x position of the right thoracic contour image; Irib denotes the region to be analyzed; $\text{IM}_{st}$ denotes the thoracic contour image.

In some embodiments, the uppermost boundary position may be determined based on the thoracic contour image within the largest connected domain according to the following equation:

$$Pos_{up} = \left(Pix_{up} - \left(\frac{M-1}{2}\right)\right) \times Spacing_{pre}, \quad \text{Equation (42)}$$

where $Pix_{up}$ denotes the uppermost element position of the thoracic contour image (i.e., the image position of the uppermost element); $Spacing_{pre}$ denotes the resolution of the elements (in the thoracic contour image); $Pos_{up}$ denotes the uppermost boundary position of the thoracic contour image (i.e., the physical position of the uppermost boundary); M denotes the matrix size of the thoracic contour image.

According to the process for determining the boundary position(s) of the thoracic contour image, the thoracic contour image may be segmented, and a left thoracic contour image and a right thoracic contour image may be obtained; the leftmost boundary position, the rightmost boundary position, and the uppermost boundary position may be determined according to the left thoracic contour image, the right thoracic contour image, and the thoracic contour image. Through the determination of the boundary position(s) of the thoracic cavity boundary, the center position of the thoracic contour can be determined more accurately, and accordingly, the position of the heart in the thoracic cavity can be determined more accurately, so that the determination of the heart position may be more accurate.

Figure 21:
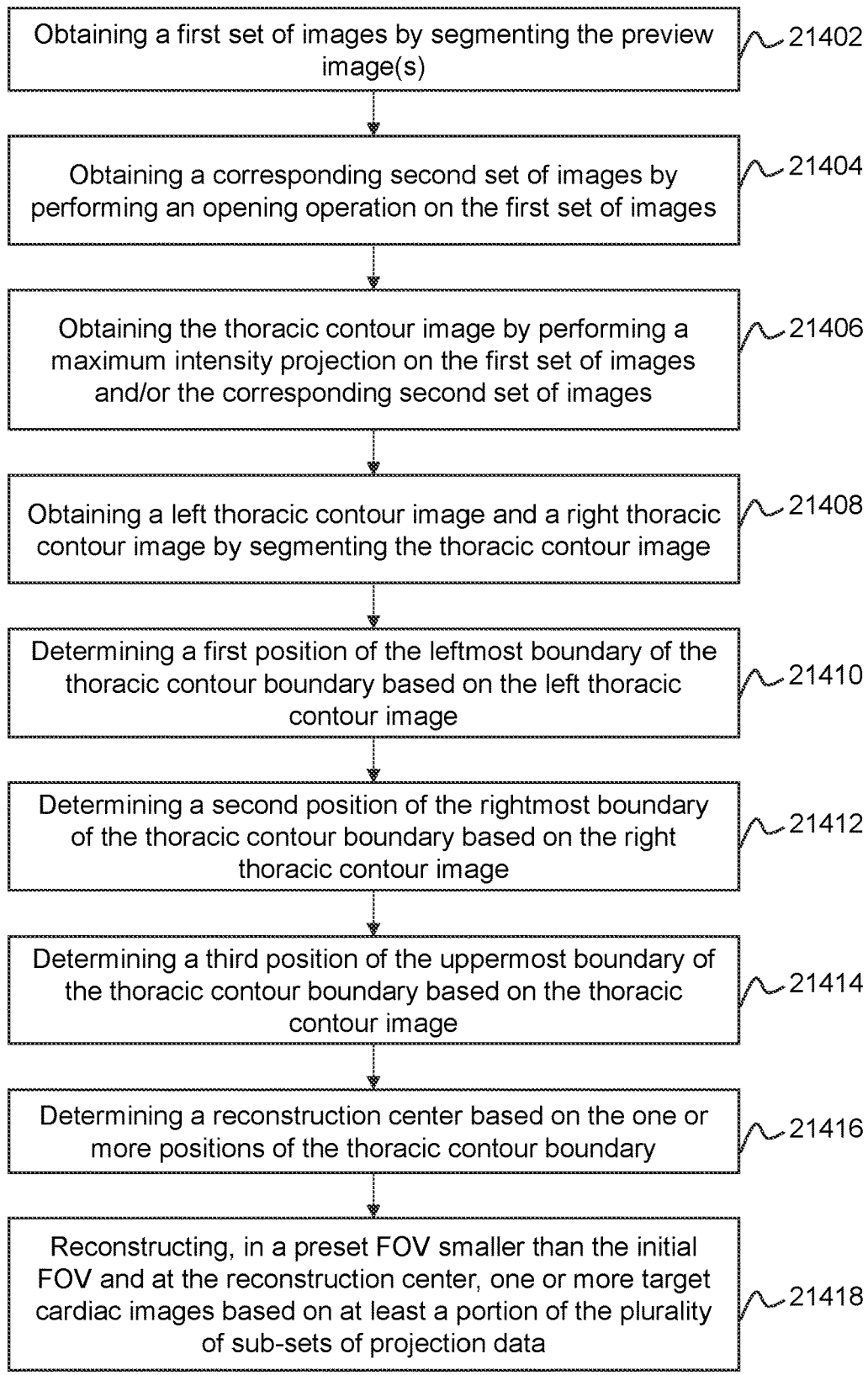
FIG. 21 is a flowchart illustrating an exemplary process for reconstructing cardiac image(s) according to some embodiments of the present disclosure.

FIG. 21 is a flowchart illustrating an exemplary process for reconstructing cardiac image(s) according to some embodiments of the present disclosure.

In some embodiments, as shown in FIG. 21, an exemplary process for cardiac image reconstruction is provided. The process 2100 may include the following operations:

In 21402, a first set of images may be obtained by segmenting the preview image(s).

In some embodiments, the processing device 140 (e.g., the maximum intensity projection module 28100 (e.g., the first image segmenting unit 29110)) may perform operation 21402. In some embodiments, a first intermediate image may be obtained by segmenting a preview image, and accordingly, a first set of images (including a plurality of first intermediate images) may be obtained by segmenting a plurality of preview images.

Specifically, in some embodiments, the preview image(s) may be original image(s) obtained after preliminary processing of data received by a computing device (e.g., the computing device 200). The preview image(s) may be original image(s) reconstructed based on a relatively large FOV (e.g., an FOV with a diameter larger than 500 mm). In some embodiments, the preview image(s) can show the structure of at least a portion of (e.g., the entire) thoracic cavity of the target object. In medical imaging technology, in order to enhance the imaging effect of a target site of an object (e.g., a patient), a contrast agent may be injected or administered to a target site (e.g., the coronary artery, the ventricle). Data obtained after injection or administration of the contrast agent may be preliminarily processed, and original image(s) of the thoracic cavity may be obtained. The original image(s) may be regarded as the preview image(s). In some embodiments, multiple preview images may be selected, and the preview images may be segmented, respectively, to obtain a first set of images. The first set of images may reflect the position(s) of bone(s) of the thoracic cavity and the position(s) of the contrast agent.

In some embodiments, the first set of images may be obtained by segmenting a plurality of preview images according to the following equation:

$$IPB1z(i, j) = \begin{cases} 1, & \text{if } IPO_z(i, j) > TB1 \\ 0, & \text{if } IPO_z(i, j) \le TB1 \end{cases}, \quad \text{Equation (43)}$$

where $IPO_z(i, j)$ denotes the element(s) of the zth preview image; TB1 denotes a threshold relating to a high density structure of the target object; IPB1 denotes image(s) that are related to bone(s) and the contrast agent and are obtained by segmenting preview image(s); $IPB1_z(i, j)$ denotes the element(s) of the zth image of the images relating to the bone(s) and the contrast agent.

In some embodiments, the first set of images may be binary images.

In 21404, a corresponding second set of images may be obtained by performing an opening operation on the first set of images.

In some embodiments, the processing device 140 (e.g., the maximum intensity projection module 28100 (e.g., the opening operation unit 29120)) may perform operation 21404. In some embodiments, a corresponding second intermediate image may be obtained by performing an opening operation on a first intermediate image, and accordingly, a second set of images (including a plurality of second intermediate images) may be obtained by performing an opening operation on the first set of images respectively. In some embodiments, the second set of images may be binary images.

Specifically, in some embodiments, according to the obtained first set of images, an opening operation may be performed on the first set of images to obtain a second set of images. The opening operation may be performed to smooth the contour(s) of the object or a portion thereof (e.g., a contour of an organ of the object), break narrow gap(s) (or discontinuities), and/or eliminate fine protrusion(s). Relatively thin edge(s) in the first set of images may be removed or reduced by performing an opening operation on the first set of images separately, and a second set of images reflecting position(s) of the contrast agent may be obtained.

In some embodiments, the second set of images may be obtained by performing the opening operation on the first set of images according to the following equation:

$$IPB2=(IPB1 \ominus se\_b1) \oplus se\_b1, \qquad \text{Equation (44)}$$

where IPB1 denotes image(s) that are related to bone(s) and the contrast agent (i.e., the first set of images) and are obtained by segmenting preview image(s); IPB2 denotes image(s) relating to the contrast agent (i.e., the second set of images) that are obtained by performing an opening operation on the image(s) relating to bone(s) and the contrast agent; se_b1 denotes a structure element in morphology operation(s); $\ominus$ denotes a corrosion operation; $\oplus$ denotes an expansion operation.

In 21406, the thoracic contour image may be obtained by performing a maximum intensity projection on the first set of images and/or the corresponding second set of images.

In some embodiments, the processing device 140 (e.g., the maximum intensity projection module 28100 (e.g., the maximum intensity projection unit 29130)) may perform operation 21406.

Specifically, in some embodiments, the obtained first set of images and the second set of images may be respectively subjected to the maximum intensity projection to obtain the thoracic contour image. The maximum intensity projection(s) may be generated based on element(s) having a maximum intensity (or density) along each projection ray directed to the patient's target site. That is, if the projection ray passes through original image(s) of the patient's target site, the element(s) with the highest intensity (or density) in the image(s) may be retained and projected onto a two-dimensional plane, thereby forming a maximum intensity projection image of the patient's target site.

More specifically, in some embodiments, the first set of images may be subjected to the maximum intensity projection in the axial direction of the thoracic cavity to obtain a maximum intensity projection image (see FIG. 22) of the first set of images. If the projection ray passes through the image(s) relating to the bone(s) and the contrast agent in the axial direction of the thoracic cavity, the element(s) with the highest intensity (or density) in the image(s) may be retained and projected onto a two-dimensional plane, thereby forming a maximum intensity projection image of the first set of images.

In some embodiments, the maximum intensity projection image of the first set of images may be obtained by projection in the axial direction of the thoracic cavity, which can be represented as the following equation:

$$IM_{B1}(i,j)=\max(IPB1_z(i,j)), z=1,2,\ldots N, \qquad \text{Equation (45)}$$

where $IPB1_z(i, j)$ denotes the element(s) of the zth image of the images relating to the bone(s) and the contrast agent (i.e., the first set of images); N denotes the number of images relating to the bone(s) and the contrast agent; $IM_{B1}$ denotes the maximum intensity projection image of the image(s) relating to the bone(s) and the contrast agent (see FIG. 22); $IM_{B1}(i, j)$ denotes the gray levels of the element(s) of the maximum intensity projection image of the image(s) relating to the bone(s) and the contrast agent.

A maximum intensity projection may be performed on the second set of image(s) in the axial direction of the thoracic cavity to obtain a maximum intensity projection image (see FIG. 23) of the second set of images. If the projection ray passes through the image(s) relating to the contrast agent in the axial direction of the thoracic cavity, the element(s) with the highest intensity (or density) in the image(s) may be retained and projected onto a two-dimensional plane, thereby forming a maximum intensity projection image of the second set of images.

In some embodiments, the maximum intensity projection image of the second set of images may be obtained by projection in the axial direction of the thoracic cavity, which can be represented as the following equation:

$$IM_{B2}(i,j)=\max(IPB2_z(i,j)), z=1,2,\ldots N, \qquad \text{Equation (46)}$$

where $IPB2_z(i, j)$ denotes the element(s) of the zth image of the images relating to the contrast agent (i.e., the second set of images); N denotes the number of the images relating to the contrast agent; $IM_{B2}$ denotes the maximum intensity projection image of the images relating to the contrast agent; $IM_{B2}(i, j)$ denotes the element(s) of the maximum intensity projection image of the images relating to the contrast agent.

In some embodiments, a difference between the maximum intensity projection image of the first set of images and the maximum intensity projection image of the second set of images may be determined as a thoracic contour image (see FIG. 24).

In some embodiments, the difference may be a subtraction between the maximum intensity projection image of the first set of images and the maximum intensity projection image of the second set of images.

In some embodiments, the thoracic contour image may be determined based on the difference between the maximum intensity projection image of the first set of images and the maximum intensity projection image of the second set of images, which may be represented as the following equation:

$$IM_{st}(i, j) = \begin{cases} IM_{B1}(i, j), & \text{if } IM_{B2}(i, j) \le 0 \\ 0, & \text{if } IM_{B2}(i, j) > 0 \end{cases}, \quad \text{Equation (47)}$$

where $IM_{B1}$ denotes the maximum intensity projection image of the images relating to the bone(s) and the contrast agent; $IM_{B1}(i, j)$ denotes the element(s) of the maximum intensity projection image of the images relating to the bone(s) and the contrast agent; $IM_{B2}$ denotes the maximum intensity projection image of the images relating to the contrast agent (see FIG. 23); $IM_2(i, j)$ denotes the element(s) of the maximum intensity projection image of the images relating to the contrast agent; $IM_{st}$ denotes a thoracic contour image; $IM_{st}(i, j)$ denotes the element(s) of the thoracic contour image.

In 21408, a left thoracic contour image and/or a right thoracic contour image may be obtained by segmenting the at least one thoracic contour image.

In some embodiments, the processing device 140 (e.g., the boundary determination module 28200 (e.g., the second image segmentation unit 31210)) may perform operation 21408. In some embodiments, the positions of the thoracic contour boundary may refer to the boundary positions of the thoracic contour image. The position(s) (or physical position(s)) of thoracic contour boundary illustrated below may refer to relative position(s) in the thoracic contour image.

Specifically, in some embodiments, the boundary positions of the thoracic contour image may include a leftmost boundary position, a rightmost boundary position, and/or an uppermost boundary position. In some embodiments, the leftmost boundary position may be a physical position of the leftmost boundary of the thoracic contour image. The rightmost boundary position may be a physical position of the rightmost boundary of the thoracic contour image. The uppermost boundary position may be a physical position of the uppermost boundary of the thoracic contour image. In some embodiments, according to the obtained thoracic contour image, segmentation may be performed on the thoracic contour image, and a left thoracic contour image and/or a right thoracic contour image may be obtained.

In some embodiments, the segmentation of the thoracic contour image to obtain the left thoracic contour image and the right thoracic contour image may be represented as the following equation:

$$IM_l(i, j) = \begin{cases} IM_{st}(i, j), & \text{if } j \le M/2 \\ 0, & \text{else} \end{cases}, \quad \text{Equation (48)}$$

$$IM_r(i, j) = \begin{cases} IM_{st}(i, j), & \text{if } j \ge M/2 \\ 0, & \text{else} \end{cases}, \quad \text{Equation (49)}$$

where $IM_{st}$ denotes a thoracic contour image; $IM_{st}(i, j)$ denotes the element(s) of the thoracic contour image; $IM_l$ denotes the left thoracic contour image; $IM_l(i, j)$ denotes the element(s) of the left thoracic contour image; $IM_r$ denotes the right thoracic contour image; $IM_r(i, j)$ denotes the element(s) of the right thoracic contour image; M denotes the matrix size of the thoracic contour image.

In 21410, a first position of the leftmost boundary of the thoracic contour boundary may be determined based on the left thoracic contour image.

In some embodiments, the processing device 140 (e.g., the boundary determination module 28200 (e.g., the left boundary determination unit 31220)) may perform operation 21410.

Specifically, in some embodiments, a largest connected domain may be determined according to the left thoracic contour image, and elements in the largest connected domain of the left thoracic contour image may be selected. The connected domain may correspond to a region in a complex plane. If a simple closed curve is used in the complex plane, and the internal of the closed curve always belongs to the region, then the region is a connected domain. The upper part of the right coronary in the largest connected domain of the left thoracic contour image may be selected, and the leftmost boundary position may be determined.

In some embodiments, the leftmost boundary position may be determined according to the following equations:

$$Pos_l = -\left(Pix_l - \left(\frac{M-1}{2}\right)\right) \times Spacing_{pre}, \quad \text{Equation (50)}$$

$$Pix_l = \min(j|(i, j) \in IM_l(i, j)), \quad \text{Equation (51)}$$

where $Pix_l$ denotes the leftmost element position of the left thoracic contour image (i.e., the image position of the leftmost element); $Spacing_{pre}$ denotes the resolution of the elements (of the left thoracic contour image); $Pos_l$ denotes the leftmost boundary position of the thoracic contour image (i.e., the physical position of the leftmost boundary); M denotes the matrix size of the thoracic contour image; $IM_l$ denotes the left thoracic contour image.

In 21412, a second position of the rightmost boundary of the thoracic contour boundary may be determined based on the right thoracic contour image.

In some embodiments, the processing device 140 (e.g., the center reconstruction module 28300 (e.g., the right boundary determination unit 31230)) may perform operation 21412.

Specifically, in some embodiments, a largest connected domain may be determined according to the left thoracic contour image, and elements in the largest connected domain of the right thoracic contour image may be selected. The connected domain may correspond to a region in a complex plane. If a simple closed curve is used in the complex plane, and the internal of the closed curve always belongs to the region, then the region is a connected domain. The upper part of the right coronary in the largest connected domain of the right thoracic contour image may be selected, and the rightmost boundary position may be determined.

In some embodiments, the rightmost boundary position may be determined according to the following equations:

$$Pos_r = -\left(Pix_r - \left(\frac{M-1}{2}\right)\right) \times Spacing_{pre}, \quad \text{Equation (52)}$$

$$Pix_r = \max(j|(i, j) \in IM_r(i, j)), \quad \text{Equation (53)}$$

where $Pix_r$ denotes the rightmost element position of the right thoracic contour image (i.e., the image position of the rightmost element); $Spacing_{pre}$ denotes the resolution of the elements (of the right thoracic contour image); $Pos_r$ denotes the rightmost boundary position of the thoracic contour image (i.e., the physical position of the rightmost boundary); M denotes the matrix size of the thoracic contour image; $IM_r$ denotes the right thoracic contour image.

In 21414, a third position of the uppermost boundary of the thoracic contour boundary may be determined based on the at least one thoracic contour image.

In some embodiments, the processing device 140 (e.g., the center reconstruction module 28300 (e.g., the upper boundary determination unit 31240)) may perform operation 21414.

Specifically, in some embodiments, a region to be analyzed may be determined in the thoracic contour image according to the rightmost position of the left thoracic contour image, the leftmost position of the right thoracic contour image, and the lowest position of the second set of images. The second set of images may include image(s) reflecting the location(s) of the elements representing the contrast agent. The largest connected domain may be determined according to the region to be analyzed, and elements in the largest connected domain of the thoracic contour image may be selected. According to the elements in the largest connected domain of the thoracic contour image, the uppermost boundary position may be determined.

In some embodiments, the region to be analyzed may be determined in the thoracic contour image based on the rightmost position of the left thoracic contour image, the leftmost position of the right thoracic contour image, and the lowest position of the second set of images according to the following equation:

$$Irib = IM_{st}(1:id, id1:id2), \quad \text{Equation (54)}$$

where id denotes the lowest y position of the set of images relating to the contrast agent; id1 denotes the rightmost x position of the left thoracic contour image; id2 denotes the leftmost x position of the right thoracic contour image; Irib denotes the region to be analyzed; $IM_{st}$ denotes the thoracic contour image.

In some embodiments, the uppermost boundary position may be determined based on the thoracic contour image within the largest connected domain according to the following equation:

$$Pos_{up} = \left(Pix_{up} - \left(\frac{M-1}{2}\right)\right) \times Spacing_{pre}, \quad \text{Equation (55)}$$

where $Pix_{up}$ denotes the uppermost element position of the thoracic contour image (i.e., the image position of the uppermost element); $Spacing_{pre}$ denotes the resolution of the elements (in the thoracic contour image); $Pos_{up}$ denotes the uppermost boundary position of the thoracic contour image (i.e., the physical position of the uppermost boundary); M denotes the matrix size of the thoracic contour image.

In 21416, a reconstruction center may be determined based on the one or more positions of the thoracic contour boundary.

In some embodiments, the processing device 140 (e.g., the center reconstruction module 28300) may perform operation 21416. In some embodiments, the processing device 140 may determine the reconstruction center based on the one or more positions of the thoracic contour boundary. In some embodiments, the reconstruction center may be a center of gravity, a geometrical center, or a center determined based on the position(s) of the thoracic contour boundary according to a rule (see Equations (56)-(57)).

Specifically, in some embodiments, a thoracic contour center may be determined based on the first position of the leftmost boundary, the second position of the rightmost boundary, and/or the third position of the uppermost boundary. In some embodiments, according to a position of the heart in the thoracic cavity, the reconstruction center may be determined as a position in an upper left region of the thoracic contour center.

In some embodiments, the reconstruction center may be determined based on the boundary position(s) of the thoracic contour image according to the following equations:

$$CenX = \text{round}\left(Pos_l + \left(\frac{Pos_r - Pos_l}{2}\right) + OffsetX\right), \quad \text{Equation (56)}$$

$$CenY = \text{round}\left(Pos_{up} + \frac{FoV}{2} + OffsetY\right), \quad \text{Equation (57)}$$

where OffsetX is a factor used to adjust the distance of the reconstruction center to the left of the contour center (of the thoracic contour); OffsetY is a factor used to adjust the distance of the reconstruction center upward from the contour center (of the thoracic contour); $Pos_l$ denotes the leftmost boundary position of the thoracic contour image; $Pos_r$ denotes the rightmost boundary position of the thoracic contour image; $Pos_{up}$ denotes the uppermost position of the thoracic contour image.

In 21418, one or more target cardiac images may be reconstructed, in a preset FOV and at the reconstruction center.

In some embodiments, the processing device 140 (e.g., the image reconstruction module 28400) may perform operation 21418.

Specifically, in some embodiments, the multi-phase reconstruction may be performed according to the determined reconstruction center and the preset reconstruction FOV. In some embodiments, the coronary artery may have a curved shape in an axial direction of the thoracic cavity, and accordingly, position(s) of the coronary artery in the axial direction of the thoracic cavity may be inconstant. Therefore, in some embodiments, the preset reconstruction FOV may not be set too small. In some embodiments, an exemplary reconstruction FOV may have a diameter of 80 mm. The reconstruction FOV may be an FOV for multi-phase reconstruction.

According to the cardiac image reconstruction method(s), apparatus(es), computing device(s) and computer readable storage medium(s), a plurality of preview images may be obtained; a thoracic contour image may be obtained according to the plurality of preview images and a maximum intensity projection algorithm; the leftmost boundary position, the rightmost boundary position, and/or the uppermost boundary position may be determined according to the thoracic contour image, and accordingly, the reconstruction center may be determined. A multi-phase reconstruction may be performed according to the reconstruction center and the preset reconstruction FOV to obtain the cardiac image(s). In some embodiments, the heart position may be determined first, and then multi-phase image reconstruction may be performed according to the heart position. Therefore, the amount of data input for the reconstruction may be reduced, the time of data input may be further reduced, and the operation efficiency may be improved.

It should be understood that although the various operations in the flowcharts of FIGS. 18-21 are displayed successfully as indicated by the arrows, these operations are not necessarily performed in the order indicated by the arrows. Except as explicitly stated herein, there is no strict ordering of the execution of these operations, and these operations may be performed in other orders. Moreover, at least a part of the operations in FIGS. 18-21 may include a plurality of sub-operations or a plurality of stages, these sub-operations or stages are not necessarily performed at the same time, but may be executed at different times. The execution order of the sub-operations or stages is also not necessarily successful, but may be performed alternately or alternately with other operations or at least a portion of sub-operations or stages of other operations.

Figure 28:
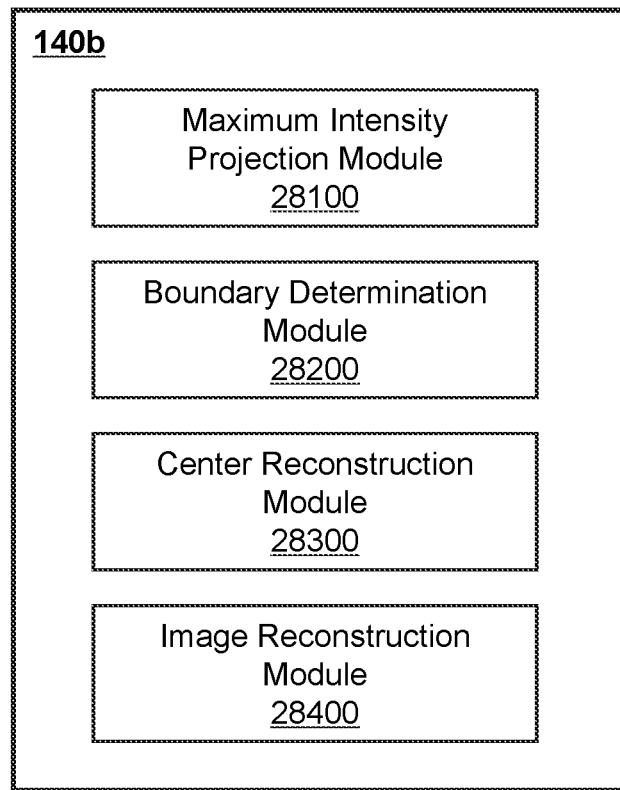
FIG. 28 is a block diagram illustrating an exemplary processing device for cardiac image reconstruction according to some embodiments of the present disclosure.

FIG. 28 is a block diagram illustrating an exemplary processing device for cardiac image reconstruction according to some embodiments of the present disclosure.

As shown in FIG. 28, a processing device 140b is provided. The processing device 140b may include: a maximum intensity projection module 28100, a boundary determination module 28200, a center reconstruction module 28300, and an image reconstruction module 28400.

The maximum intensity projection module 28100 may be configured to obtain a plurality of preview images, and/or generate a thoracic contour image according to the plurality of preview images and a maximum intensity projection algorithm.

More descriptions of the maximum intensity projection module 28100 may be found elsewhere in the present disclosure (e.g., FIGS. 18, 19, and 21 and descriptions thereof).

The boundary determination module 28200 may be configured to determine boundary position(s) of the thoracic contour image according to the thoracic contour image.

More descriptions of the boundary determination module 28200 may be found elsewhere in the present disclosure (e.g., FIGS. 18, 20, and 21 and descriptions thereof).

The center reconstruction module 28300 may be configured to determine a reconstruction center according to one or more boundary positions of the thoracic contour image.

More descriptions of the center reconstruction module 28300 may be found elsewhere in the present disclosure (e.g., FIGS. 18 and 21 and descriptions thereof).

The image reconstruction module 28400 may be configured to perform image reconstruction (e.g., multi-phase reconstruction) according to the reconstruction center and the preset FOV to obtain cardiac image(s).

More descriptions of the image reconstruction module 28400 may be found elsewhere in the present disclosure (e.g., FIGS. 18 and 21 and descriptions thereof).

Figure 29:
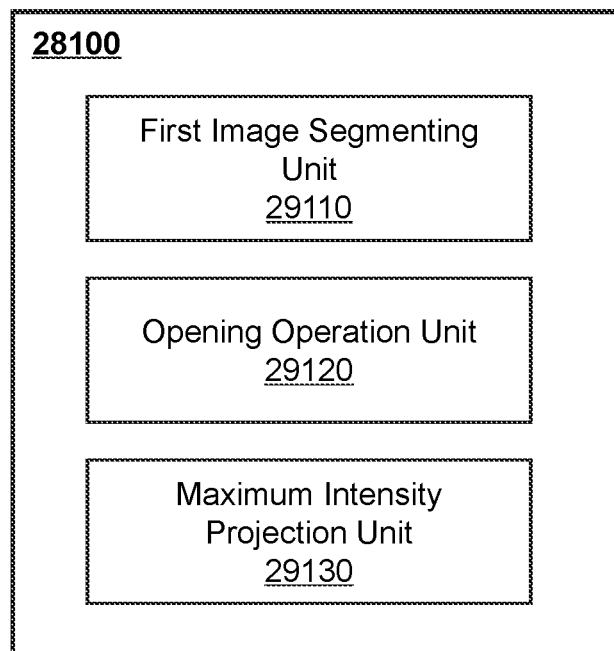
FIG. 29 is a block diagram illustrating an exemplary maximum intensity projection module according to some embodiments of the present disclosure.

FIG. 29 is a block diagram illustrating an exemplary maximum intensity projection module according to some embodiments of the present disclosure.

As shown in FIG. 29, a maximum intensity projection module 28100 is provided. The maximum intensity projection module 28100 may include a first image segmenting unit 29110, an opening operation unit 29120, and a maximum intensity projection unit 29130.

The first image segmenting unit 29110 may be configured to obtain one or more preview images, and perform segmentation of the preview image(s) to obtain a first set of images.

The opening operation unit 29120 may be configured to perform an opening operation on the first set of images to obtain a second set of images.

The maximum intensity projection unit 29130 may be configured to perform a maximum intensity projection on the first set of images and/or the second set of images respectively to obtain a thoracic contour image.

FIG. 30 is a block diagram illustrating an exemplary maximum intensity projection unit according to some embodiments of the present disclosure.

As shown in FIG. 30, a maximum intensity projection unit 29130 is provided. The maximum intensity projection unit 29130 may include a first maximum intensity projection sub-unit 30131, a second maximum intensity projection sub-unit 30132, and a difference determination sub-unit 30133.

The first maximum intensity projection sub-unit 30131 may be configured to perform a maximum intensity projection on the first set of images in the axial direction of the thoracic cavity to obtain a maximum intensity projection image of the first set of images.

The second maximum intensity projection sub-unit 30132 may be configured to perform a maximum intensity projection on the second set of images in the axial direction of the thoracic cavity to obtain a maximum intensity projection image of the second set of images.

The difference determination sub-unit 30133 may be configured to determine a difference between the maximum intensity projection image of the first set of images and the maximum intensity projection image of the second set of images to obtain a thoracic contour image.

FIG. 31 is a block diagram illustrating an exemplary boundary determination module according to some embodiments of the present disclosure.

As shown in FIG. 31, a boundary determination module 28200 is provided. The boundary determination module 28200 may include a second image segmentation unit 31210, a left boundary determination unit 31220, a right boundary determination unit 31230, and an upper boundary determination unit 31240.

The second image segmentation unit 31210 may be configured to perform one or more segmentation operations on the thoracic contour image to obtain a left thoracic contour image and a right thoracic contour image.

The left boundary determination unit 31220 may be configured to determine the leftmost boundary position according to the left thoracic contour image.

The right boundary determination unit 31230 may be configured to determine the rightmost boundary position according to the right thoracic contour image.

The upper boundary determination unit 31240 may be configured to determine the uppermost boundary position according to the thoracic contour image.

Figure 32:
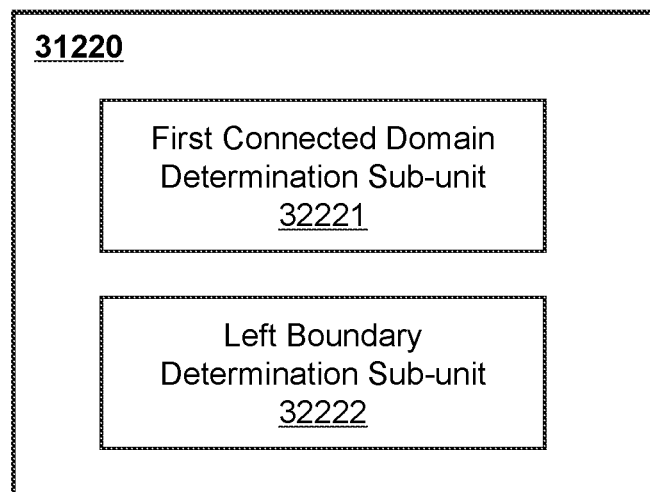
FIG. 32 is a block diagram illustrating an exemplary left boundary determination unit according to some embodiments of the present disclosure.

FIG. 32 is a block diagram illustrating an exemplary left boundary determination unit according to some embodiments of the present disclosure.

As shown in FIG. 32, a left boundary determination unit 31220 is provided. The left boundary determination unit 31220 may include a first connected domain determination sub-unit 32221 and a left boundary determination sub-unit 32222.

The first connected domain determination sub-unit 32221 may be configured to determine a maximum connected domain according to the left thoracic contour image, and select elements in the largest connected domain of the left thoracic contour image.

The left boundary determination sub-unit 32222 may be configured to select elements in an upper part of the right coronary in the largest connected domain of the left thoracic contour image, and determine the leftmost boundary position.

Figure 33:
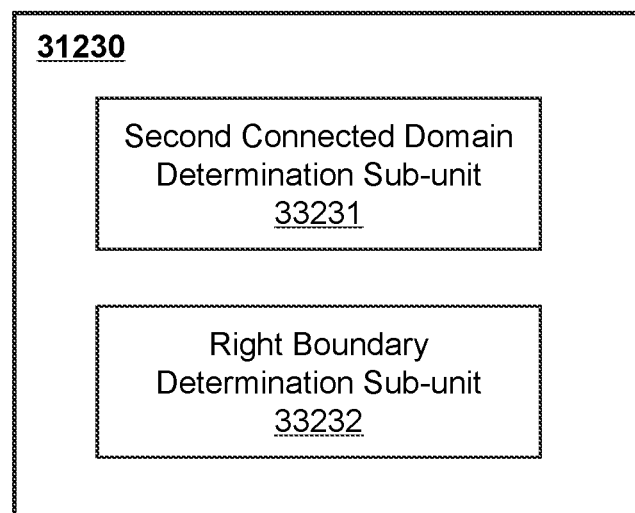
FIG. 33 is a block diagram illustrating an exemplary right boundary determination unit according to some embodiments of the present disclosure.

FIG. 33 is a block diagram illustrating an exemplary right boundary determination unit according to some embodiments of the present disclosure.

As shown in FIG. 33, a right boundary determination unit 31230 is provided. The right boundary determination unit 31230 may include a second connected domain determination sub-unit 33231 and a right boundary determination sub-unit 33232.

The second connected domain determination sub-unit 33231 may be configured to determine a maximum connected domain according to the right thoracic contour image, and select elements within the largest connected domain of the right thoracic contour image.

The right boundary determination sub-unit 33232 may be configured to select elements in an upper part of the right coronary in the largest connected domain of the right thoracic contour image, and determine the rightmost boundary position.

Figure 34:
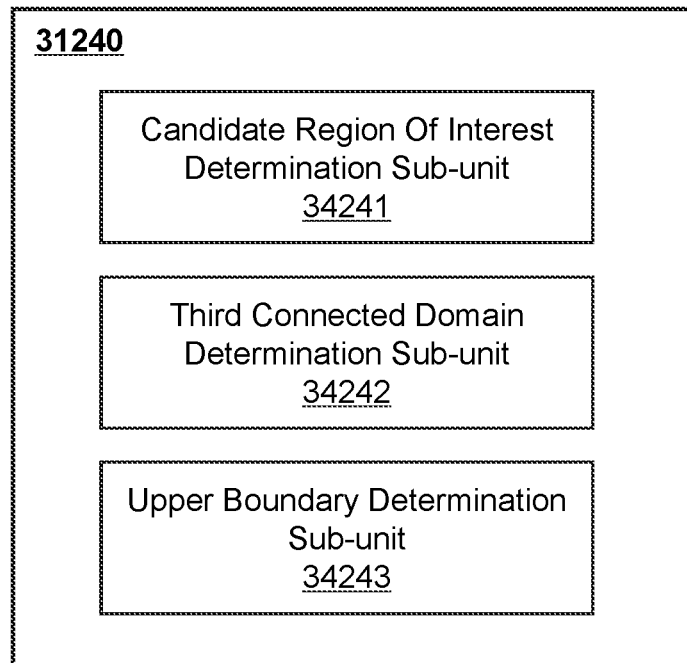
FIG. 34 is a block diagram illustrating an exemplary upper boundary determination unit according to some embodiments of the present disclosure.

FIG. 34 is a block diagram illustrating an exemplary upper boundary determination unit according to some embodiments of the present disclosure.

As shown in FIG. 34, an upper boundary determination unit 31240 is provided. The upper boundary determination unit 31240 may include a candidate region of interest determination sub-unit 34241, a third connected domain determination sub-unit 34242, and an upper boundary determination sub-unit 34243.

The candidate region of interest determination sub-unit 34241 may be configured to determine a region to be analyzed in the thoracic contour image according to the rightmost position of the left thoracic contour image, the leftmost position of the right thoracic contour image, and the lowest position of the second set of images.

The third connected domain determination sub-unit 34242 may be configured to determine a maximum connected domain according to the region to be analyzed, and select elements within the largest connected domain of the thoracic contour image.

The upper boundary determination sub-unit 34243 may be configured to determine the uppermost boundary position according to the elements in the largest connected domain of the thoracic contour image.

For specific definitions of the card image reconstruction device, refer to the above definition of the cardiac image reconstruction method, and details are not repeated herein. The various modules in the cardiac image reconstruction apparatus can be implemented in whole or in part of software, hardware, and combinations thereof. The modules may be embedded in or independent of the processing device 140 in the computing device, or may be stored in the memory of the computing device in the form of software, so that the processing device 140 may call to perform the operations corresponding to the above modules.

Figure 35:
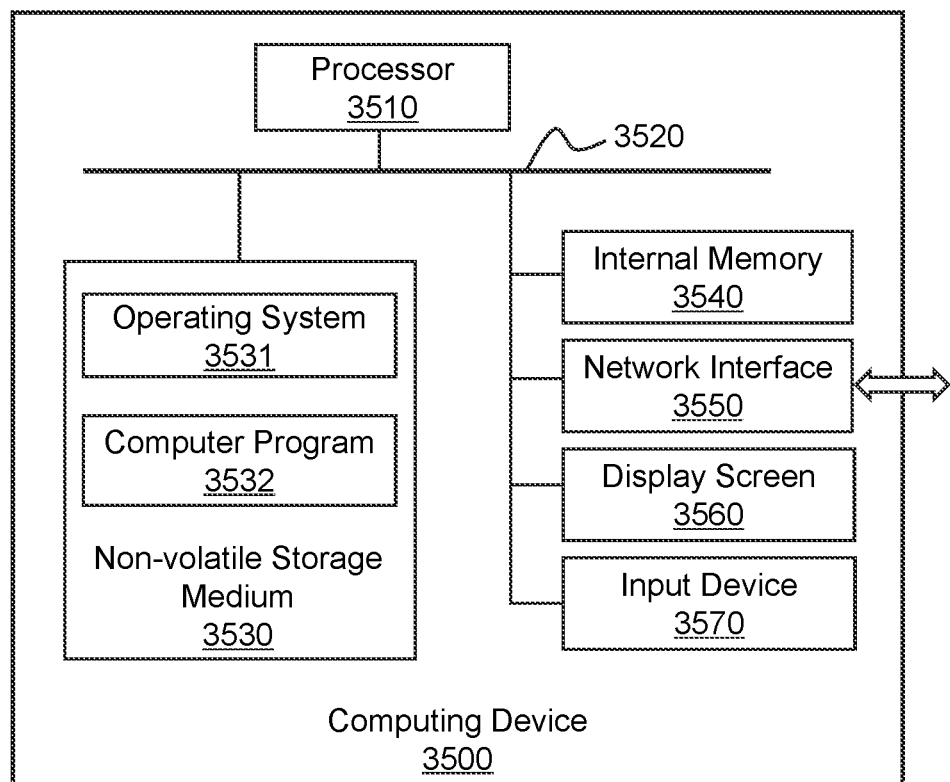
FIG. 35 is a schematic diagram illustrating an exemplary computing device according to some embodiments of the present disclosure.

FIG. 35 is a schematic diagram illustrating an exemplary computing device according to some embodiments of the present disclosure.

As shown in FIG. 35, a computing device 3500 is provided. The computing device 3500 may be a terminal. The internal components of the computing device 3500 may be shown in FIG. 35. The computing device 3500 may include a processor 3510, a memory, a network interface 3550, a display screen 3560, and an input device 3570 connected by a system bus 3520. The processor 3510 of the computing device 3500 may provide computing and/or control capabilities. The memory of the computing device 3500 may include a non-volatile storage medium 3530, an internal memory 3540. The non-volatile storage medium 3530 may store an operating system 3531 and computer program(s) 3532. The internal memory 3540 may provide an environment for operation of the operating system 3531 and the computer program(s) 3532 in the non-volatile storage medium 3530. The network interface 3550 of the computing device 3500 may communicate with an external terminal via a network connection. The computer program(s) 3532 may be executed by the processor 3510 to implement a cardiac image reconstruction process. The display screen 3560 of the computing device 3500 may include a liquid crystal display or an electronic ink display screen, and the input device 3570 of the computing device 3500 may include a touch layer covered on the display screen, or may include a button, a trajectory ball or a touchpad provided on the casing of the computing device. It may also be an external keyboard, trackpad, or mouse, or the like.

It will be understood by those skilled in the art that the structure shown in FIG. 35 is only a block diagram of a part of the structure related to the present disclosure, and does not constitute a limitation on the computing device on which the present disclosure scheme is applied. The computing device may include more or fewer components than those shown in the figures, or some components may be combined, or have different component arrangements.

In some embodiments, a computer apparatus is provided comprising a memory and a processor having computer program(s) stored therein. The processor may implement one or more of the following operations when executing the computer program(s).

A plurality of preview images may be obtained as input, and a thoracic contour image may be obtained according to the preview image(s) and a maximum intensity projection algorithm; the boundary position(s) of the thoracic contour image may be determined according to the thoracic contour image; a reconstruction center may be determined according to the boundary position(s) of the thoracic contour image; and multi-phase reconstruction may be performed according to the reconstruction center and the preset reconstruction FOV to obtain the cardiac image(s).

In some embodiments, the processing device 140 may implement one or more of the following operations when executing the computer program(s).

A plurality of preview images may be obtained as input; the preview image(s) may be segmented to obtain a first set of images; an opening operation may be performed on the first set of images to obtain a second set of images; and a maximum intensity projection may be performed on the first set of images and the second set of images, respectively, to obtain a thoracic contour image.

In some embodiments, the processing device 140 may implement one or more of the following operations when executing the computer program(s).

The thoracic contour image may be segmented to obtain a left thoracic contour image and a right thoracic contour image; the leftmost boundary position may be determined according to the left thoracic contour image; the rightmost boundary position may be determined according to the right thoracic contour image; and the uppermost boundary position may be determined based on the thoracic contour image.

In some embodiments, the processing device 140 may implement one or more of the following operations when executing the computer program(s).

A plurality of preview images may be obtained as input; the preview image(s) may be segmented to obtain a first set of images; an opening operation may be performed on the first set of images to obtain a second set of images; a maximum intensity projection may be performed on the first set of images and the second set of images respectively to obtain a thoracic contour image; the thoracic contour image may be segmented to obtain a left thoracic contour image and a right thoracic contour image; the leftmost boundary position may be determined according to the left thoracic contour image; the rightmost boundary position may be determined according to the right thoracic contour image; the uppermost boundary position may be determined according to the thoracic contour image; a reconstruction center may be determined according to the boundary position(s) of the thoracic contour image; the multi-phase reconstruction may be performed according to the reconstruction center and the preset reconstruction FOV to obtain the cardiac image(s).

In some embodiments, a non-transitory computer readable medium storing instructions is provided. The instructions, when executed by the processing device, may cause the processing device to implement one or more operations illustrated above.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one machine each of which has at least one processor and at least one storage device for reconstructing one or more target cardiac images, the method comprising:
   obtaining a plurality of projection data corresponding to a plurality of cardiac motion phases;
   determining a plurality of cardiac motion parameters corresponding to at least a portion of the plurality of cardiac motion phases based on the plurality of projection data wherein the plurality of cardiac motion parameters are associated with coronary artery motion;
   determining a phase of interest based on the plurality of cardiac motion parameters; and
   reconstructing the one or more target cardiac images of the phase of interest.

2. The method of claim 1, wherein the determining a plurality of cardiac motion parameters corresponding to at least a portion of the plurality of cardiac motion phases based on the plurality of projection data includes:
   reconstructing a plurality of cardiac images of the at least a portion of the plurality of cardiac motion phases based on the plurality of projection data;
   obtaining a plurality of mean absolute differences (MADs) by determining an MAD between two cardiac images of each two adjacent cardiac motion phases in the at least a portion of the plurality of cardiac motion phases; and
   determining the plurality of cardiac motion parameters corresponding to the at least a portion of the plurality of cardiac motion phases based on the plurality of mean absolute differences.

3. The method of claim 2, further comprising:
   preprocessing the plurality of cardiac images, including:
      extracting one or more regions relating to cardiac motion by segmenting the plurality of cardiac images; and
      designating the one or more regions relating to cardiac motion as the plurality of cardiac images.

4. The method of claim 1, wherein the determining a plurality of cardiac motion parameters corresponding to at least a portion of the plurality of cardiac motion phases based on the plurality of projection data includes:
   for each cardiac motion phase of the at least a portion of the plurality of cardiac motion phases,
      determining a first mean absolute difference (MAD) between a first cardiac image of a first cardiac motion phase that occurs before the each cardiac motion phase and a cardiac image of the each cardiac motion phase;
      determining a second mean absolute difference (MAD) between a second cardiac image of a second cardiac motion phase that occurs after the each cardiac motion phase and the cardiac image of the each cardiac motion phase; and
      designating a sum of the first mean absolute difference (MAD) and the second mean absolute difference (MAD) as the cardiac motion parameter corresponding to the each cardiac motion phase.

5. The method of claim 4, wherein the first cardiac motion phase is adjacent to the each cardiac motion phase, and the second cardiac motion phase is adjacent to the each cardiac motion phase.

6. The method of claim 1, wherein the determining a plurality of cardiac motion parameters corresponding to at least a portion of the plurality of cardiac motion phases based on the plurality of projection data includes:
   for each cardiac motion phase of the at least a portion of the plurality of cardiac motion phases,
      determining a set of initial cardiac images of interest based on the one or more cardiac images of the each cardiac motion phase, an average cardiac rate, and a standard deviation of cardiac rates;
      extracting one or more vascular images of interest of the at least a portion of the plurality of cardiac motion phases from the set of initial cardiac images of interest; and
      determining the cardiac motion parameter corresponding to the each cardiac motion phase based on the one or more vascular images of interest.

7. The method of claim 6, wherein the determining the cardiac motion parameter corresponding to the each cardiac motion phase based on the one or more vascular images of interest includes:
   determining a first vascular center in each vascular image of interest of the each cardiac motion phase;
   determining a displacement of the first vascular center based on a first position of the first vascular center in the each vascular image of interest and a second position of a second vascular center in a vascular image of interest of another cardiac motion phase adjacent to the each cardiac motion phase;
   determining an interval between the each cardiac motion phase and the another cardiac motion phase adjacent to the each cardiac motion phase; and
   determining, based on the displacement and the interval, a motion rate of the first vascular center; and
   designating the motion rate of the first vascular center as the cardiac motion parameter.

8. The method of claim 1, wherein the plurality of projection data are generated in a plurality of cardiac cycles, and the determining a phase of interest based on the plurality of cardiac motion parameters includes:
   determining a mean phase based on the plurality of cardiac motion parameters corresponding to the at least a portion of the plurality of cardiac motion phases;
   for each of the plurality of cardiac cycles, selecting one or more cardiac motion phases in a preset phase range in the each cardiac cycle of the plurality of cardiac cycles, the preset range including the mean phase;

reconstructing one or more cardiac images of the one or more cardiac motion phases based on one or more sub-sets of projection data of the plurality of projection data corresponding to the one or more cardiac motion phases in the each cardiac cycle;

determining the phase of interest in the each cardiac cycle based on the one or more cardiac images of the each cardiac cycle.

9. The method of claim 1, wherein the plurality of cardiac motion parameters corresponding to at least a portion of the plurality of cardiac motion phases further includes motion rates of vascular centers.

10. A method implemented on at least one machine each of which has at least one processor and at least one storage device for reconstructing one or more target cardiac images, the method comprising:

obtaining a plurality of projection data corresponding to a plurality of cardiac motion phases;

determining a phase of interest by inputting the plurality of projection data into one or more deep neural networks; and reconstructing the one or more target cardiac images of the phase of interest.

11. The method of claim 10, wherein the determining a phase of interest based on the plurality of projection data using one or more deep neural networks includes:

extracting, based on the plurality of projection data, one or more images of a region of interest (ROI) using a first deep neural network of the one or more deep neural networks; and selecting, based on projection data associated with the one or more images of the ROI, the phase of interest using a second deep neural network of the one or more deep neural networks.

12. The method of claim 11, wherein the first deep neural network is trained using sample images of the ROI and one of sample projection data and sample raw data, the sample images of the ROI being obtained by:

reconstructing sample images based on the sample projection data or the sample raw data; and extracting the sample images of the ROI from the reconstructed sample images.

13. The method of claim 12, wherein the first deep neural network is trained by:

inputting the sample projection data or the sample raw data into the first deep neural network;

outputting sample projection data associated with the sample images of the ROI using the first deep neural network; and adjusting parameters of the first deep neural network based on the sample projection data associated with the sample images of the ROI, and the sample images of the ROI.

14. The method of claim 11, wherein the second deep neural network is trained using sample projection data associated with sample images of the ROI corresponding to the plurality of cardiac motion phases, the sample projection data associated with the sample images of the ROI being generated by performing a forward projection on the sample images of the ROI.

15. The method of claim 14, wherein the second deep neural network is trained by:

inputting the sample projection data associated with sample images of the ROI corresponding to the plurality of cardiac motion phases into the second deep neural network to obtain an output of the second deep neural network; and adjusting parameters of the second deep neural network based on the output of the second deep neural network, and labels associated with the phase of interest.

16. A method implemented on at least one machine each of which has at least one processor and at least one storage device for reconstructing one or more target cardiac images, the method comprising:

obtaining a plurality of projection data;

determining a reconstruction center based on at least one preview image associated with at least a portion of the plurality of projection data, wherein the at least one preview image reflects a structure of at least a portion of thoracic cavity of a target object; and reconstructing, according to the reconstruction center, the one or more target cardiac images based on at least a portion of the plurality of projection data.

17. The method of claim 16, wherein the at least one preview image is reconstructed in an initial field of view (FOV) based on the at least a portion of the plurality of projection data, and the one or more target cardiac images are reconstructed in a preset FOV smaller than the initial FOV.

18. The method of claim 16, wherein the determining a reconstruction center based on at least one preview image associated with at least a portion of the plurality of projection data includes:

obtaining a thoracic contour image by performing a maximum intensity projection on the at least one preview image; and determining the reconstruction center based on the thoracic contour image.

19. The method of claim 18, wherein the determining the reconstruction center based on the thoracic contour image includes:

determining one or more positions of a thoracic contour boundary in the thoracic contour image; and determining the reconstruction center based on the one or more positions of the thoracic contour boundary.

20. The method of claim 18, wherein the obtaining a thoracic contour image by performing a maximum intensity projection on the at least one preview image includes:

obtaining a first set of images by generating a first intermediate image through segmenting each preview image of the at least one preview image;

obtaining a corresponding second set of images by generating a second intermediate image through performing an opening operation on the first intermediate image; and obtaining the thoracic contour image by performing a maximum intensity projection on the first set of images and the second set of images.

* * * * *